US007078484B2

(12) United States Patent
Kinrade et al.

(10) Patent No.: US 7,078,484 B2
(45) Date of Patent: Jul. 18, 2006

(54) MELANIN CONCENTRATING HORMONE RECEPTORS

(75) Inventors: Michele Bennet Kinrade, Northford, CT (US); Robbin M. Brodbeck, Madison, CT (US); Stephen M. Waters, Branford, CT (US); James E. Krause, Madison, CT (US)

(73) Assignee: Neurogen Corporation, Branford, CT (US)

( * ) Notice: Subject to any disclaimer, the term of this patent is extended or adjusted under 35 U.S.C. 154(b) by 545 days.

(21) Appl. No.: 10/309,515

(22) Filed: Dec. 4, 2002

(65) Prior Publication Data

US 2003/0114644 A1 Jun. 19, 2003

Related U.S. Application Data

(63) Continuation-in-part of application No. 10/126,764, filed on Apr. 18, 2002.

(60) Provisional application No. 60/284,835, filed on Apr. 19, 2001.

(51) Int. Cl.
*C07K 14/46* (2006.01)
*C07K 14/575* (2006.01)

(52) U.S. Cl. ...................................... 530/350; 530/399

(58) Field of Classification Search ..................... None
See application file for complete search history.

(56) References Cited

U.S. PATENT DOCUMENTS

| | | | |
|---|---|---|---|
| 6,008,012 | A | 12/1999 | Bergsma et al. |
| 6,033,872 | A | 3/2000 | Bergsma et al. |
| 6,221,613 | B1 | 4/2001 | Salon et al. |
| 6,221,616 | B1 | 4/2001 | Salon et al. |
| 6,291,195 | B1 | 9/2001 | Salon et al. |
| 6,362,326 | B1 | 3/2002 | Sathe et al. |
| 6,723,552 | B1 | 4/2004 | Salon et al. |
| 2002/0038007 | A1 | 3/2002 | Ames et al. |
| 2003/0082623 | A1 | 5/2003 | Borowsky et al. |
| 2004/0038855 | A1 | 2/2004 | Salon et al. |
| 2004/0248129 | A1 | 12/2004 | Tan et al. |

FOREIGN PATENT DOCUMENTS

| | | |
|---|---|---|
| EP | 848060 A2 | 6/1998 |
| WO | WO 96/18651 | 6/1996 |
| WO | WO 99/28492 | 6/1999 |
| WO | WO 00/39279 | 7/2000 |
| WO | WO 00/40725 | 7/2000 |
| WO | WO 00/49170 | 8/2000 |
| WO | WO 00/70347 | 11/2000 |
| WO | WO 00/75166 | 12/2000 |
| WO | WO 01/05947 | 1/2001 |
| WO | WO 01/07606 | 2/2001 |
| WO | WO 01/43759 | 6/2001 |
| WO | WO 01/68706 | 9/2001 |
| WO | WO 02/02744 | 1/2002 |
| WO | WO 02/03070 | 1/2002 |
| WO | WO 02/08290 | 1/2002 |
| WO | WO 02/36076 | 5/2002 |
| WO | WO 03/027239 | 4/2003 |
| WO | WO 03/027240 | 4/2003 |

OTHER PUBLICATIONS

Kolakowski et al., "Characterization of a human gene related to genes encoding somatostatin receptors," FEBS Letters 398 (1996) 253-258.

Lakaye et al., "Cloning of the rat brain cDNA encoding for the SLC-1 G protein-coupled receptor reveals the presence of an intron in the gene," Biochimica et Biophysica Acta 1401 (1998) 216-220.

Chambers et al., "Melanin-concentrating hormone is the cognate ligand for the orphan G-protein-coupled receptor SLC-1," Nature 400 (1999) 261-265.

Saito et al., "Molecular characterization of the melanin-concentrating-hormone receptor," Nature 400 (1999) 265-269.

*Primary Examiner*—Ruixiang Li
(74) *Attorney, Agent, or Firm*—Ann T. Kadlecek; Seth A. Fidel

(57) ABSTRACT

Isolated polynucleotides encoding monkey Melanin Concentrating Hormone (MCH) Type 1 receptors and chimeric polypeptides are provided. Vectors and cells for recombinant expression of such MCH1R polypeptides, and isolated MCH1R polypeptides are also provided. MCH1R polynucleotides and polypeptides may be used, for example, to identify compounds that specifically interact with MCH receptor. Such compounds find use within therapies for humans and animals afflicted with conditions associated with MCH receptor activation.

8 Claims, 4 Drawing Sheets

```
                        1........10 .........20 .........30 .........40
c.mac MCH1R ext         MSVRAAKEGV  GRAVGLGGGS  GCQAAKEDPL  PDCGACAPGQ
c.mac MCH1R             ----------  ----------  ----------  ----------
seq ID 2 6,008,012      MLCPSKTDGS  GHSGRIHQET  HGEG-KRDKI  SNSEGRE--N
human MCH1R             ----------  ----------  ----------  ----------
rat MCH1R               ----------  ----------  ----------  ----------

                        .........50 .........60 .........70 .........80
c.mac MCH1R ext         GGRRWRLPQP  AWVEGSSAWL  WEPATGTGWM  DLEASLLPTG
c.mac MCH1R             ----------  ----------  ---------M  DLEASLLPTG
seq ID 2 6,008,012      GGRGFQMN--  ---GGS----  --------LE  AEHASRMSVL
human MCH1R             ----------  ----------  ---------M  DLEASLLPTG
rat MCH1R               ----------  ----------  ---------M  DLQTSLLSTG

                        .........90 ........100 ........110 ........120
c.mac MCH1R ext         PNTSNTSDGP  DNLTSAGSPP  RSGSVSYINI  IMPSVFGTIC
c.mac MCH1R             PNTSNTSDGP  DNLTSAGSPP  RSGSVSYINI  IMPSVFGTIC
seq ID 2 6,008,012      RAKPMSNSQR  LLLLSPGSPP  RTGSISYINI  IMPSVFGTIC
human MCH1R             PNASNTSDGP  DNLTSAGSPP  RTGSISYINI  IMPSVFGTIC
rat MCH1R               PNASNISDGQ  DNLTLPGSPP  RTGSVSYINI  IMPSVFGTIC

                        ........130 ........140 ........150 ........160
c.mac MCH1R ext         LLGIIGNSMV  IFAVVKKSKL  HWCNNVPDIF  IINLSVVDLL
c.mac MCH1R             LLGIIGNSMV  IFAVVKKSKL  HWCNNVPDIF  IINLSVVDLL
seq ID 2 6,008,012      LLGIIGNSTV  IFAVVKKSKL  HWCNNVPDIF  IINLSVVDLL
human MCH1R             LLGIIGNSTV  IFAVVKKSKL  HWCNNVPDIF  IINLSVVDLL
rat MCH1R               LLGIVGNSTV  IFAVVKKSKL  HWCSNVPDIF  IINLSVVDLL

                        ........170 ........180 ........190 ........200
c.mac MCH1R ext         FLLGMPFMIH  QLMGNGVWHF  GETMCTLITA  MDANSQFTST
c.mac MCH1R             FLLGMPFMIH  QLMGNGVWHF  GETMCTLITA  MDANSQFTST
seq ID 2 6,008,012      FLLGMPFMIH  QLMGNGVWHF  GETMCTLITA  MDANSQFTST
human MCH1R             FLLGMPFMIH  QLMGNGVWHF  GETMCTLITA  MDANSQFTST
rat MCH1R               FLLGMPFMIH  QLMGNGVWHF  GETMCTLITA  MDANSQFTST

                        ........210 ........220 ........230 ........240
c.mac MCH1R ext         YILTAMAIDR  YLATVHPISS  TKFRKPSVAT  LVICLLWALS
c.mac MCH1R             YILTAMAIDR  YLATVHPISS  TKFRKPSVAT  LVICLLWALS
seq ID 2 6,008,012      YILTAMAIDR  YLATVHPISS  TKFRKPSVAT  LVICLLWALS
human MCH1R             YILTAMAIDR  YLATVHPISS  TKFRKPSVAT  LVICLLWALS
rat MCH1R               YILTAMTIDR  YLATVHPISS  TKFRKPSMAT  LVICLLWALS
```

Figure 1A

| | ........250 | ........260 | ........270 | ........280 |
|---|---|---|---|---|
| c.mac MCH1R ext | FISITPVWLY | ARLIPFPGGA | VGCGIRLPNP | DTDLYWFTLY |
| c.mac MCH1R | FISITPVWLY | ARLIPFPGGA | VGCGIRLPNP | DTDLYWFTLY |
| seq ID 2 6,008,012 | FISITPVWLY | ARLIPFPGGA | VGCGIRLPNP | DTDLYWFTLY |
| human MCH1R | FISITPVWLY | ARLIPFPGGA | VGCGIRLPNP | DTDLYWFTLY |
| rat MCH1R | FISITPVWLY | ARLIPFPGGA | VGCGIRLPNP | DTDLYWFTLY |

| | ........290 | ........300 | ........310 | ........320 |
|---|---|---|---|---|
| c.mac MCH1R ext | QFFLAFALPF | VVITAAYVRI | LQRMTSSVAP | ASQRSIRLRT |
| c.mac MCH1R | QFFLAFALPF | VVITAAYVRI | LQRMTSSVAP | ASQRSIRLRT |
| seq ID 2 6,008,012 | QFFLAFALPF | VVITAAYVRI | LQRMTSSVAP | ASQRSIRLRT |
| human MCH1R | QFFLAFALPF | VVITAAYVRI | LQRMTSSVAP | ASQRSIRLRT |
| rat MCH1R | QFFLAFALPF | VVITAAYVKI | LQRMTSSVAP | ASQRSIRLRT |

| | ........330 | ........340 | ........350 | ........360 |
|---|---|---|---|---|
| c.mac MCH1R ext | KRVTRTAIAI | CLVFFVCWAP | YYVLQLTQLS | ISRPTLTFVY |
| c.mac MCH1R | KRVTRTAIAI | CLVFFVCWAP | YYVLQLTQLS | ISRPTLTFVY |
| seq ID 2 6,008,012 | KRVTRTAIAI | CLVFFVCWAP | YYVLQLTQLS | ISRPTLTFVY |
| human MCH1R | KRVTRTAIAI | CLVFFVCWAP | YYVLQLTQLS | ISRPTLTFVY |
| rat MCH1R | KRVTRTAIAI | CLVFFVCWAP | YYVLQLTQLS | ISRPTLTFVY |

| | ........370 | ........380 | ........390 | ........400 |
|---|---|---|---|---|
| c.mac MCH1R ext | LYNAAISLGY | ANSCLNPFVY | IVLCETFRKR | LVLSVKPAAQ |
| c.mac MCH1R | LYNAAISLGY | ANSCLNPFVY | IVLCETFRKR | LVLSVKPAAQ |
| seq ID 2 6,008,012 | LYNAAISLGY | ANSCLNPFVY | IVLCETFRKR | LVLSVKPAAQ |
| human MCH1R | LYNAAISLGY | ANSCLNPFVY | IVLCETFRKR | LVLSVKPAAQ |
| rat MCH1R | LYNAAISLGY | ANSCLNPFVY | IVLCETFRKR | LVLSVKPAAQ |

| | ........410 | ........420 | ........430 | ........440 |
|---|---|---|---|---|
| c.mac MCH1R ext | GQLRAVSNAQ | TADEERTESK | GT | |
| c.mac MCH1R | GQLRAVSNAQ | TADEERTESK | GT | |
| seq ID 2 6,008,012 | GQLRAVSNAQ | TADEERTESK | GT | |
| human MCH1R | GQLRAVSNAQ | TADEERTESK | GT | |
| rat MCH1R | GQLRTVSNAQ | TADEERTESK | GT | |

Figure 1B

```
                   1........10 .........20 .........30 .........40
c.mac MCH1R        ---------- ---------- ---------- ----------
c.mac MCH1R ext    MSVRAAKEGV GRAVGLGGGS GCQAAKEDPL PDCGACAPGQ
AR169785 hMCH1     MSVGAMKKGV GRAVGLGGGS GCQATEEDPL PDCGACAPGQ

                   .........50 .........60 .........70 .........80
c.mac MCH1R        ---------- ---------- ---------M DLEASLLPTG
c.mac MCH1R ext    GGRRWRLPQP AWVEGSSAWL WEPATGTGWM DLEASLLPTG
AR169785 hMCH1     GGRRWRLPQP AWVEGSSAWL WEQATGTGWM DLEASLLPTG

                   .........90 ........100 ........110 ........120
c.mac MCH1R        PNTSNTSDGP DNLTSAGSPP RSGSVSYINI IMPSVFGTIC
c.mac MCH1R ext    PNTSNTSDGP DNLTSAGSPP RSGSVSYINI IMPSVFGTIC
AR169785 hMCH1     PNASNTSDGP DNLTSAGSPP RTGSISYINI IMPSVFGTIC

                   ........130 ........140 ........150 ........160
c.mac MCH1R        LLGIIGNSMV IFAVVKKSKL HWCNNVPDIF IINLSVVDLL
c.mac MCH1R ext    LLGIIGNSMV IFAVVKKSKL HWCNNVPDIF IINLSVVDLL
AR169785 hMCH1     LLGIIGNSTV IFAVVKKSKL HWCNNVPDIF IINLSVVDLL

                   ........170 ........180 ........190 ........200
c.mac MCH1R ext    FLLGMPFMIH QLMGNGVWHF GETMCTLITA MDANSQFTST
c.mac MCH1R ext    FLLGMPFMIH QLMGNGVWHF GETMCTLITA MDANSQFTST
AR169785 hMCH1     FLLGMPFMIH QLMGNGVWHF GETMCTLITA MDANSQFTST

                   ........210 ........220 ........230 ........240
c.mac MCH1R        YILTAMAIDR YLATVHPISS TKFRKPSVAT LVICLLWALS
c.mac MCH1R ext    YILTAMAIDR YLATVHPISS TKFRKPSVAT LVICLLWALS
AR169785 hMCH1     YILTAMAIDR YLATVHPISS TKFRKPSVAT LVICLLWALS
```

Figure 2A

| | .........250 | .........260 | .........270 | .........280 |
|---|---|---|---|---|
| c.mac MCH1R | FISITPVWLY | ARLIPFPGGA | VGCGIRLPNP | DTDLYWFTLY |
| c.mac MCH1R ext | FISITPVWLY | ARLIPFPGGA | VGCGIRLPNP | DTDLYWFTLY |
| AR169785 hMCH1 | FISITPVWLY | ARLIPFPGGA | VGCGIRLPNP | DTDLYWFTLY |

| | .........290 | .........300 | .........310 | .........320 |
|---|---|---|---|---|
| c.mac MCH1R | QFFLAFALPF | VVITAAYVRI | LQRMTSSVAP | ASQRSIRLRT |
| c.mac MCH1R ext | QFFLAFALPF | VVITAAYVRI | LQRMTSSVAP | ASQRSIRLRT |
| AR169785 hMCH1 | QFFLAFALPF | VVITAAYVRI | LQRMTSSVAP | ASQRSIRLRT |

| | .........330 | .........340 | .........350 | .........360 |
|---|---|---|---|---|
| c.mac MCH1R | KRVTRTAIAI | CLVFFVCWAP | YYVLQLTQLS | ISRPTLTFVY |
| c.mac MCH1R ext | KRVTRTAIAI | CLVFFVCWAP | YYVLQLTQLS | ISRPTLTFVY |
| AR169785 hMCH1 | KRVTRTAIAI | CLVFFVCWAP | YYVLQLTQLS | ISRPTLTFVY |

| | .........370 | .........380 | .........390 | .........400 |
|---|---|---|---|---|
| c.mac MCH1R | LYNAAISLGY | ANSCLNPFVY | IVLCETFRKR | LVLSVKPAAQ |
| c.mac MCH1R ext | LYNAAISLGY | ANSCLNPFVY | IVLCETFRKR | LVLSVKPAAQ |
| AR169785 hMCH1 | LYNAAISLGY | ANSCLNPFVY | IVLCETFRKR | LVLSVKPAAQ |

| | .........410 | .........420 | .........430 | .........440 |
|---|---|---|---|---|
| c.mac MCH1R | GQLRAVSNAQ | TADEERTESK | GT | |
| c.mac MCH1R ext | GQLRAVSNAQ | TADEERTESK | GT | |
| AR169785 hMCH1 | GQLRAVSNAQ | TADEERTESK | GT | |

Figure 2B

SEQUENCE LISTING

```
<160> NUMBER OF SEQ ID NOS: 60

<210> SEQ ID NO 1
<211> LENGTH: 1062
<212> TYPE: DNA
<213> ORGANISM: Macaca fascicularis

<400> SEQUENCE: 1

atggacctgg aagcctcgct gctgcccact ggtcccaaca ccagcaacac ctctgatggc     60

cccgataacc tcacctcggc aggatcacct cctcgctcag ggagcgtctc ctacatcaac    120

atcatcatgc cttcggtgtt cggcaccatc tgcctcctgg gcatcatcgg gaactccatg    180

gtcatcttcg cggtcgtgaa gaagtccaag ctgcactggt gcaacaatgt ccccgacatc    240

ttcatcatca acctctcggt ggtggatctc ctctttctcc tgggcatgcc cttcatgatc    300

caccagctca tgggcaatgg ggtgtggcac tttggggaga ccatgtgcac cctcatcacg    360

gccatggatg ccaatagtca gttcaccagc acctacatcc tgaccgccat ggccattgac    420

cgctacctgg ccaccgtcca ccccatctct tccacaaagt tccggaagcc ctctgtggcc    480

accctggtga tctgcctcct gtgggccctc tccttcatca gcatcacccc cgtgtggttg    540

tatgccagac tcatcccctt cccaggaggt gcagtgggct gcggcatccg cttgcccaac    600

ccggacactg acctttactg gttcaccctg taccagtttt tcctggcctt tgccctgccc    660

ttcgtggtca tcacggccgc atacgtgagg atcctgcagc gcatgacgtc ctcagtggcc    720

cccgcctccc agcgcagcat ccggctgcgg acaaagaggg tgacccgcac agccatcgcc    780

atctgcctgg tcttctttgt gtgctgggca ccctactatg tgctacagct gacccagttg    840

tccatcagcc gcccgaccct caccttttgtc tacctgtaca atgcggccat cagcttgggc    900

tacgccaaca gctgcctcaa cccctttgtg tacattgtgc tctgcgagac gttccgcaaa    960

cgcttggtcc tttcggtgaa gcctgcagcc caggggcagc ttcgcgctgt cagcaacgct   1020

cagacggctg acgaggagag gacagaaagc aaaggtacct ga                      1062

<210> SEQ ID NO 2
<211> LENGTH: 353
<212> TYPE: PRT
<213> ORGANISM: Macaca fascicularis

<400> SEQUENCE: 2

Met Asp Leu Glu Ala Ser Leu Leu Pro Thr Gly Pro Asn Thr Ser Asn
1               5                   10                  15
```

-continued

```
Thr Ser Asp Gly Pro Asp Asn Leu Thr Ser Ala Gly Ser Pro Pro Arg
            20                  25                  30

Ser Gly Ser Val Ser Tyr Ile Asn Ile Ile Met Pro Ser Val Phe Gly
        35                  40                  45

Thr Ile Cys Leu Leu Gly Ile Ile Gly Asn Ser Met Val Ile Phe Ala
    50                  55                  60

Val Val Lys Lys Ser Lys Leu His Trp Cys Asn Asn Val Pro Asp Ile
65                  70                  75                  80

Phe Ile Ile Asn Leu Ser Val Val Asp Leu Leu Phe Leu Leu Gly Met
                85                  90                  95

Pro Phe Met Ile His Gln Leu Met Gly Asn Gly Val Trp His Phe Gly
            100                 105                 110

Glu Thr Met Cys Thr Leu Ile Thr Ala Met Asp Ala Asn Ser Gln Phe
        115                 120                 125

Thr Ser Thr Tyr Ile Leu Thr Ala Met Ala Ile Asp Arg Tyr Leu Ala
    130                 135                 140

Thr Val His Pro Ile Ser Ser Thr Lys Phe Arg Lys Pro Ser Val Ala
145                 150                 155                 160

Thr Leu Val Ile Cys Leu Leu Trp Ala Leu Ser Phe Ile Ser Ile Thr
                165                 170                 175

Pro Val Trp Leu Tyr Ala Arg Leu Ile Pro Phe Pro Gly Gly Ala Val
            180                 185                 190

Gly Cys Gly Ile Arg Leu Pro Asn Pro Asp Thr Asp Leu Tyr Trp Phe
        195                 200                 205

Thr Leu Tyr Gln Phe Phe Leu Ala Phe Ala Leu Pro Phe Val Val Ile
    210                 215                 220

Thr Ala Ala Tyr Val Arg Ile Leu Gln Arg Met Thr Ser Ser Val Ala
225                 230                 235                 240

Pro Ala Ser Gln Arg Ser Ile Arg Leu Arg Thr Lys Arg Val Thr Arg
                245                 250                 255

Thr Ala Ile Ala Ile Cys Leu Val Phe Phe Val Cys Trp Ala Pro Tyr
            260                 265                 270

Tyr Val Leu Gln Leu Thr Gln Leu Ser Ile Ser Arg Pro Thr Leu Thr
        275                 280                 285

Phe Val Tyr Leu Tyr Asn Ala Ala Ile Ser Leu Gly Tyr Ala Asn Ser
    290                 295                 300

Cys Leu Asn Pro Phe Val Tyr Ile Val Leu Cys Glu Thr Phe Arg Lys
305                 310                 315                 320

Arg Leu Val Leu Ser Val Lys Pro Ala Ala Gln Gly Gln Leu Arg Ala
                325                 330                 335

Val Ser Asn Ala Gln Thr Ala Asp Glu Glu Arg Thr Glu Ser Lys Gly
            340                 345                 350

Thr


<210> SEQ ID NO 3
<211> LENGTH: 6
<212> TYPE: PRT
<213> ORGANISM: artificial sequence
<220> FEATURE:
<223> OTHER INFORMATION: His 6x epitope

<400> SEQUENCE: 3

His His His His His His
1               5
```

<210> SEQ ID NO 4
<211> LENGTH: 8
<212> TYPE: PRT
<213> ORGANISM: artificial sequence
<220> FEATURE:
<223> OTHER INFORMATION: FLAG epitope

<400> SEQUENCE: 4

```
Asp Tyr Lys Asp Asp Asp Asp Lys
1               5
```

<210> SEQ ID NO 5
<211> LENGTH: 1062
<212> TYPE: DNA
<213> ORGANISM: Homo sapiens

<400> SEQUENCE: 5

```
atggacctgg aagcctcgct gctgcccact ggtcccaacg ccagcaacac ctctgatggc     60

cccgataacc tcacttcggc aggatcacct cctcgcacgg ggagcatctc ctacatcaac    120

atcatcatgc cttcggtgtt cggcaccatc tgcctcctgg gcatcatcgg gaactccacg    180

gtcatcttcg cggtcgtgaa gaagtccaag ctgcactggt gcaacaacgt ccccgacatc    240

ttcatcatca acctctcggt agtagatctc ctctttctcc tgggcatgcc cttcatgatc    300

caccagctca tgggcaatgg ggtgtggcac tttggggaga ccatgtgcac cctcatcacg    360

gccatggatg ccaatagtca gttcaccagc acctacatcc tgaccgccat ggccattgac    420

cgctacctgg ccactgtcca ccccatctct tccacgaagt tccggaagcc ctctgtggcc    480

accctggtga tctgcctcct gtgggccctc tccttcatca gcatcacccc tgtgtggctg    540

tatgccagac tcatcccctt cccaggaggt gcagtgggct gcggcatacg cctgcccaac    600

ccagacactg acctctactg gttcaccctg taccagtttt tcctggcctt tgccctgcct    660

tttgtggtca tcacagccgc atacgtgagg atcctgcagc gcatgacgtc ctcagtggcc    720

cccgcctccc agcgcagcat ccggctgcgg acaaagaggg tgacccgcac agccatcgcc    780

atctgtctgg tcttctttgt gtgctgggca ccctactatg tgctacagct gacccagttg    840

tccatcagcc gcccgaccct cacctttgtc tacttataca atgcggccat cagcttgggc    900

tatgccaaca gctgcctcaa ccccttgtg tacatcgtgc tctgtgagac gttccgcaaa    960

cgcttggtcc tgtcggtgaa gcctgcagcc caggggcagc ttcgcgctgt cagcaacgct   1020

cagacggctg acgaggagag gacagaaagc aaaggcacct ga                      1062
```

<210> SEQ ID NO 6
<211> LENGTH: 353
<212> TYPE: PRT
<213> ORGANISM: homosapiens

<400> SEQUENCE: 6

```
Met Asp Leu Glu Ala Ser Leu Leu Pro Thr Gly Pro Asn Ala Ser Asn
1               5                   10                  15

Thr Ser Asp Gly Pro Asp Asn Leu Thr Ser Ala Gly Ser Pro Pro Arg
            20                  25                  30

Thr Gly Ser Ile Ser Tyr Ile Asn Ile Ile Met Pro Ser Val Phe Gly
        35                  40                  45

Thr Ile Cys Leu Leu Gly Ile Ile Gly Asn Ser Thr Val Ile Phe Ala
    50                  55                  60

Val Val Lys Lys Ser Lys Leu His Trp Cys Asn Asn Val Pro Asp Ile
65                  70                  75                  80
```

-continued

```
Phe Ile Ile Asn Leu Ser Val Val Asp Leu Leu Phe Leu Leu Gly Met
                85                  90                  95

Pro Phe Met Ile His Gln Leu Met Gly Asn Gly Val Trp His Phe Gly
            100                 105                 110

Glu Thr Met Cys Thr Leu Ile Thr Ala Met Asp Ala Asn Ser Gln Phe
        115                 120                 125

Thr Ser Thr Tyr Ile Leu Thr Ala Met Ala Ile Asp Arg Tyr Leu Ala
    130                 135                 140

Thr Val His Pro Ile Ser Ser Thr Lys Phe Arg Lys Pro Ser Val Ala
145                 150                 155                 160

Thr Leu Val Ile Cys Leu Leu Trp Ala Leu Ser Phe Ile Ser Ile Thr
                165                 170                 175

Pro Val Trp Leu Tyr Ala Arg Leu Ile Pro Phe Pro Gly Gly Ala Val
            180                 185                 190

Gly Cys Gly Ile Arg Leu Pro Asn Pro Asp Thr Asp Leu Tyr Trp Phe
        195                 200                 205

Thr Leu Tyr Gln Phe Phe Leu Ala Phe Ala Leu Pro Phe Val Val Ile
    210                 215                 220

Thr Ala Ala Tyr Val Arg Ile Leu Gln Arg Met Thr Ser Ser Val Ala
225                 230                 235                 240

Pro Ala Ser Gln Arg Ser Ile Arg Leu Arg Thr Lys Arg Val Thr Arg
                245                 250                 255

Thr Ala Ile Ala Ile Cys Leu Val Phe Phe Val Cys Trp Ala Pro Tyr
            260                 265                 270

Tyr Val Leu Gln Leu Thr Gln Leu Ser Ile Ser Arg Pro Thr Leu Thr
        275                 280                 285

Phe Val Tyr Leu Tyr Asn Ala Ala Ile Ser Leu Gly Tyr Ala Asn Ser
    290                 295                 300

Cys Leu Asn Pro Phe Val Tyr Ile Val Leu Cys Glu Thr Phe Arg Lys
305                 310                 315                 320

Arg Leu Val Leu Ser Val Lys Pro Ala Ala Gln Gly Gln Leu Arg Ala
                325                 330                 335

Val Ser Asn Ala Gln Thr Ala Asp Glu Glu Arg Thr Glu Ser Lys Gly
            340                 345                 350

Thr


<210> SEQ ID NO 7
<211> LENGTH: 24
<212> TYPE: DNA
<213> ORGANISM: artificial sequence
<220> FEATURE:
<223> OTHER INFORMATION: 5' Cynomolgus macaque MCH1R primer

<400> SEQUENCE: 7

gagcaggcga ccggcactgg ctgg                                              24


<210> SEQ ID NO 8
<211> LENGTH: 28
<212> TYPE: DNA
<213> ORGANISM: artificial sequence
<220> FEATURE:
<223> OTHER INFORMATION: 3' Cynomolgus macaque MCH1R primer

<400> SEQUENCE: 8

ggaggtgtgc agggtggcag gggaagta                                          28


<210> SEQ ID NO 9
```

<211> LENGTH: 1155
<212> TYPE: DNA
<213> ORGANISM: homo sapiens

<400> SEQUENCE: 9

```
atgaattcaa cattattttc ccaggttgaa aatcattcag tccactctaa tttctcagag     60
aagaatgccc agcttctggc ttttgaaaat gatgattgtc atctgccctt ggccatgata    120
tttaccttag ctcttgctta tggagctgtg atcattcttg gtgtctctgg aaacctggcc    180
ttgatcataa tcatcttgaa acaaaaggag atgagaaatg ttaccaacat cctgattgtg    240
aacctttcct tctcagactt gcttgttgcc atcatgtgtc tcccctttac atttgtctac    300
acattaatgg accactgggt ctttggtgag gcgatgtgta agttgaatcc ttttgtgcaa    360
tgtgtttcaa tcactgtgtc cattttctct ctggttctca ttgctgtgga acgacatcag    420
ctgataatca accctcgagg gtggagacca aataatagac atgcttatgt aggtattgct    480
gtgatttggg tccttgctgt ggcttcttct ttgcctttcc tgatctacca agtaatgact    540
gatgagccgt tccaaaatgt aacacttgat gcgtacaaag acaaatacgt gtgctttgat    600
caatttccat cggactctca taggttgtct tataccactc tcctcttggt gctgcagtat    660
tttggtccac tttgttttat atttatttgc tacttcaaga tatatatacg cctaaaaagg    720
agaaacaaca tgatggacaa gatgagagac aataagtaca ggtccagtga aaccaaaaga    780
atcaatatca tgctgctctc cattgtggta gcatttgcag tctgctggct ccctcttacc    840
atctttaaca ctgtgtttga ttggaatcat cagatcattg ctacctgcaa ccacaatctg    900
ttattcctgc tctgccacct cacagcaatg atatccactt gtgtcaaccc catattttat    960
gggttcctga acaaaaactt ccagagagac ttgcagttct tcttcaactt ttgtgatttc   1020
cggtctcggg atgatgatta tgaaacaata gccatgtcca cgatgcacac agatgtttcc   1080
aaaacttctt tgaagcaagc aagcccagtc gcatttaaaa aaatcaacaa caatgatgat   1140
aatgaaaaaa tctga                                                    1155
```

<210> SEQ ID NO 10
<211> LENGTH: 384
<212> TYPE: PRT
<213> ORGANISM: Homo sapiens

<400> SEQUENCE: 10

```
Met Asn Ser Thr Leu Phe Ser Gln Val Glu Asn His Ser Val His Ser
1               5                   10                  15

Asn Phe Ser Glu Lys Asn Ala Gln Leu Leu Ala Phe Glu Asn Asp Asp
            20                  25                  30

Cys His Leu Pro Leu Ala Met Ile Phe Thr Leu Ala Leu Ala Tyr Gly
        35                  40                  45

Ala Val Ile Ile Leu Gly Val Ser Gly Asn Leu Ala Leu Ile Ile Ile
    50                  55                  60

Ile Leu Lys Gln Lys Glu Met Arg Asn Val Thr Asn Ile Leu Ile Val
65                  70                  75                  80

Asn Leu Ser Phe Ser Asp Leu Leu Val Ala Ile Met Cys Leu Pro Phe
                85                  90                  95

Thr Phe Val Tyr Thr Leu Met Asp His Trp Val Phe Gly Glu Ala Met
            100                 105                 110

Cys Lys Leu Asn Pro Phe Val Gln Cys Val Ser Ile Thr Val Ser Ile
        115                 120                 125

Phe Ser Leu Val Leu Ile Ala Val Glu Arg His Gln Leu Ile Ile Asn
```

-continued

```
    130                 135                 140

Pro Arg Gly Trp Arg Pro Asn Asn Arg His Ala Tyr Val Gly Ile Ala
145                 150                 155                 160

Val Ile Trp Val Leu Ala Val Ala Ser Ser Leu Pro Phe Leu Ile Tyr
                165                 170                 175

Gln Val Met Thr Asp Glu Pro Phe Gln Asn Val Thr Leu Asp Ala Tyr
            180                 185                 190

Lys Asp Lys Tyr Val Cys Phe Asp Gln Phe Pro Ser Asp Ser His Arg
        195                 200                 205

Leu Ser Tyr Thr Thr Leu Leu Leu Val Leu Gln Tyr Phe Gly Pro Leu
    210                 215                 220

Cys Phe Ile Phe Ile Cys Tyr Phe Lys Ile Tyr Ile Arg Leu Lys Arg
225                 230                 235                 240

Arg Asn Asn Met Met Asp Lys Met Arg Asp Asn Lys Tyr Arg Ser Ser
                245                 250                 255

Glu Thr Lys Arg Ile Asn Ile Met Leu Leu Ser Ile Val Val Ala Phe
            260                 265                 270

Ala Val Cys Trp Leu Pro Leu Thr Ile Phe Asn Thr Val Phe Asp Trp
        275                 280                 285

Asn His Gln Ile Ile Ala Thr Cys Asn His Asn Leu Leu Phe Leu Leu
    290                 295                 300

Cys His Leu Thr Ala Met Ile Ser Thr Cys Val Asn Pro Ile Phe Tyr
305                 310                 315                 320

Gly Phe Leu Asn Lys Asn Phe Gln Arg Asp Leu Gln Phe Phe Phe Asn
                325                 330                 335

Phe Cys Asp Phe Arg Ser Arg Asp Asp Asp Tyr Glu Thr Ile Ala Met
            340                 345                 350

Ser Thr Met His Thr Asp Val Ser Lys Thr Ser Leu Lys Gln Ala Ser
        355                 360                 365

Pro Val Ala Phe Lys Lys Ile Asn Asn Asn Asp Asp Asn Glu Lys Ile
    370                 375                 380
```

<210> SEQ ID NO 11
<211> LENGTH: 25
<212> TYPE: DNA
<213> ORGANISM: artificial sequence
<220> FEATURE:
<223> OTHER INFORMATION: human NPY1 receptor - BspE forward primer for C-terminal

<400> SEQUENCE: 11
aaacttccgg agagacttgc agttc 25

<210> SEQ ID NO 12
<211> LENGTH: 32
<212> TYPE: DNA
<213> ORGANISM: artificial sequence
<220> FEATURE:
<223> OTHER INFORMATION: human NPY1 receptor - reverse primer for C-terminal

<400> SEQUENCE: 12
catccgcggc cgcaggctat aagtagtttc ag 32

<210> SEQ ID NO 13
<211> LENGTH: 199
<212> TYPE: DNA
<213> ORGANISM: homo sapiens -continued

<400> SEQUENCE: 13

```
tccggagaga cttgcagttc ttcttcaact tttgtgattt ccggtctcgg gatgatgatt     60

atgaaacaat agccatgtcc acgatgcaca cagatgtttc caaaacttct ttgaagcaag    120

caagcccagt cgcatttaaa aaaatcaaca acaatgatga taatgaaaaa atctgaaact    180

acttatagcc tgcggccgc                                                 199
```

<210> SEQ ID NO 14
<211> LENGTH: 82
<212> TYPE: DNA
<213> ORGANISM: artificial sequence
<220> FEATURE:
<223> OTHER INFORMATION: Human NPY1 receptor IC3 sense oligo

<400> SEQUENCE: 14

```
gatcctgata cgcctaaaaa ggagaaacaa catgatggac aagatgagag acaataagta     60

caggtccagt gaaaccaaaa gg                                              82
```

<210> SEQ ID NO 15
<211> LENGTH: 83
<212> TYPE: DNA
<213> ORGANISM: artificial sequence
<220> FEATURE:
<223> OTHER INFORMATION: human NPY1 receptor IC3 antisense oligo

<400> SEQUENCE: 15

```
gtcacccttt tggtttcact ggacctgtac ttattgtctc tcatcttgtc catcatgttg     60

tttctccttt ttaggcgtat cag                                             83
```

<210> SEQ ID NO 16
<211> LENGTH: 1062
<212> TYPE: DNA
<213> ORGANISM: artificial sequence
<220> FEATURE:
<223> OTHER INFORMATION: human MCH1R plus BspE site added for C-terminal chimera

<400> SEQUENCE: 16

```
atggacctgg aagcctcgct gctgcccact ggtcccaacg ccagcaacac ctctgatggc     60

cccgataacc tcacttcggc aggatcacct cctcgcacgg ggagcatctc ctacatcaac    120

atcatcatgc cttcggtgtt cggcaccatc tgcctcctgg gcatcatcgg gaactccacg    180

gtcatcttcg cggtcgtgaa gaagtccaag ctgcactggt gcaacaacgt ccccgacatc    240

ttcatcatca acctctcggt agtagatctc ctctttctcc tgggcatgcc cttcatgatc    300

caccagctca tgggcaatgg ggtgtggcac tttggggaga ccatgtgcac cctcatcacg    360

gccatggatg ccaatagtca gttcaccagc acctacatcc tgaccgccat ggccattgac    420

cgctacctgg ccactgtcca ccccatctct tccacgaagt tccggaagcc ctctgtggcc    480

accctggtga tctgcctcct gtgggccctc tccttcatca gcatcacccc tgtgtggctg    540

tatgccagac tcatcccctt cccaggaggt gcagtgggct gcggcatacg cctgcccaac    600

ccagacactg acctctactg gttcaccctg taccagtttt tcctggcctt tgccctgcct    660

tttgtggtca tcacagccgc atacgtgagg atcctgcagc gcatgacgtc ctcagtggcc    720

cccgcctccc agcgcagcat ccggctgcgg acaaagaggg tgacccgcac agccatcgcc    780

atctgtctgg tcttctttgt gtgctgggca ccctactatg tgctacagct gacccagttg    840

tccatcagcc gcccgaccct cacctttgtc tacttataca atgcggccat cagcttgggc    900
```

-continued

```
tatgccaaca gctgcctcaa ccccttttgtg tacatcgtgc tctgtgagac gttccggaaa     960

cgcttggtcc tgtcggtgaa gcctgcagcc caggggcagc ttcgcgctgt cagcaacgct    1020

cagacggctg acgaggagag gacagaaagc aaaggcacct ga                        1062
```

<210> SEQ ID NO 17
<211> LENGTH: 1074
<212> TYPE: DNA
<213> ORGANISM: artificial sequence
<220> FEATURE:
<223> OTHER INFORMATION: human MCH1R/NPY1 IC3 chimera

<400> SEQUENCE: 17

```
atggacctgg aagcctcgct gctgcccact ggtcccaatg ccagcaacac ctctgatggc      60

cccgataacc tcacttcggc aggatcacct cctcgcacgg ggagcatctc ctacatcaac     120

atcatcatgc cttcggtgtt cggcaccatc tgcctcctgg gcatcatcgg gaactccacg     180

gtcatcttcg cggtcgtgaa gaagtccaag ctgcactggt gcaacaacgt ccccgacatc     240

ttcatcatca acctctcggt agtagatctc ctctttctcc tgggcatgcc cttcatgatc     300

caccagctca tgggcaatgg ggtgtggcac tttggggaga ccatgtgcac cctcatcacg     360

gccatggatg ccaatagtca gttcaccagc acctacatcc tgaccgccat ggccattgac     420

cgctacctgg ccactgtcca ccccatctct tccacgaagt tccggaagcc ctctgtggcc     480

accctggtga tctgcctcct gtgggccctc tccttcatca gcatcacccc tgtgtggctg     540

tatgccagac tcatcccctt cccaggaggt gcagtgggct gcggcatacg cctgcccaac     600

ccagacactg acctctactg gttcaccctg taccagtttt tcctggcctt tgccctgcct     660

tttgtggtca tcacagccgc atacgtgagg atcctgatac gcctaaaaag gagaaacaac     720

atgatggaca agatgagaga caataagtac aggtccagtg aaaccaaaag ggtgacccgc     780

acagccatcg ccatctgtct ggtcttcttt gtgtgctggg caccctacta tgtgctacag     840

ctgacccagt tgtccatcag ccgcccgacc ctcacctttg tctacttata caatgcggcc     900

atcagcttgg gctatgccaa cagctgcctc aacccctttg tgtacatcgt gctctgtgag     960

acgttccgca aacgcttggt cctgtcggtg aagcctgcag cccaggggca gcttcgcgct    1020

gtcagcaacg ctcagacggc tgacgaggag aggacagaaa gcaaaggcac ctga          1074
```

<210> SEQ ID NO 18
<211> LENGTH: 357
<212> TYPE: PRT
<213> ORGANISM: artificial sequence
<220> FEATURE:
<223> OTHER INFORMATION: human MCH1R/NPY1 IC3 loop chimera

<400> SEQUENCE: 18

```
Met Asp Leu Glu Ala Ser Leu Leu Pro Thr Gly Pro Asn Ala Ser Asn
1               5                   10                  15

Thr Ser Asp Gly Pro Asp Asn Leu Thr Ser Ala Gly Ser Pro Pro Arg
            20                  25                  30

Thr Gly Ser Ile Ser Tyr Ile Asn Ile Ile Met Pro Ser Val Phe Gly
        35                  40                  45

Thr Ile Cys Leu Leu Gly Ile Ile Gly Asn Ser Thr Val Ile Phe Ala
    50                  55                  60

Val Val Lys Lys Ser Lys Leu His Trp Cys Asn Asn Val Pro Asp Ile
65                  70                  75                  80

Phe Ile Ile Asn Leu Ser Val Val Asp Leu Leu Phe Leu Leu Gly Met
                85                  90                  95
```

```
Pro Phe Met Ile His Gln Leu Met Gly Asn Gly Val Trp His Phe Gly
            100                 105                 110

Glu Thr Met Cys Thr Leu Ile Thr Ala Met Asp Ala Asn Ser Gln Phe
        115                 120                 125

Thr Ser Thr Tyr Ile Leu Thr Ala Met Ala Ile Asp Arg Tyr Leu Ala
    130                 135                 140

Thr Val His Pro Ile Ser Ser Thr Lys Phe Arg Lys Pro Ser Val Ala
145                 150                 155                 160

Thr Leu Val Ile Cys Leu Leu Trp Ala Leu Ser Phe Ile Ser Ile Thr
                165                 170                 175

Pro Val Trp Leu Tyr Ala Arg Leu Ile Pro Phe Pro Gly Gly Ala Val
            180                 185                 190

Gly Cys Gly Ile Arg Leu Pro Asn Pro Asp Thr Asp Leu Tyr Trp Phe
        195                 200                 205

Thr Leu Tyr Gln Phe Phe Leu Ala Phe Ala Leu Pro Phe Val Val Ile
    210                 215                 220

Thr Ala Ala Tyr Val Arg Ile Leu Ile Arg Leu Lys Arg Arg Asn Asn
225                 230                 235                 240

Met Met Asp Lys Met Arg Asp Asn Lys Tyr Arg Ser Ser Glu Thr Lys
                245                 250                 255

Arg Val Thr Arg Thr Ala Ile Ala Ile Cys Leu Val Phe Phe Val Cys
            260                 265                 270

Trp Ala Pro Tyr Tyr Val Leu Gln Leu Thr Gln Leu Ser Ile Ser Arg
        275                 280                 285

Pro Thr Leu Thr Phe Val Tyr Leu Tyr Asn Ala Ala Ile Ser Leu Gly
    290                 295                 300

Tyr Ala Asn Ser Cys Leu Asn Pro Phe Val Tyr Ile Val Leu Cys Glu
305                 310                 315                 320

Thr Phe Arg Lys Arg Leu Val Leu Ser Val Lys Pro Ala Ala Gln Gly
                325                 330                 335

Gln Leu Arg Ala Val Ser Asn Ala Gln Thr Ala Asp Glu Glu Arg Thr
            340                 345                 350

Glu Ser Lys Gly Thr
        355
```

<210> SEQ ID NO 19
<211> LENGTH: 1128
<212> TYPE: DNA
<213> ORGANISM: artificial sequence
<220> FEATURE:
<223> OTHER INFORMATION: human MCH1R/human NPY1 C-terminal chimera

<400> SEQUENCE: 19

```
atggacctgg aagcctcgct gctgcccact ggtcccaatg ccagcaacac ctctgatggc      60

cccgataacc tcacttcggc aggatcacct cctcgcacgg ggagcatctc ctacatcaac     120

atcatcatgc cttcggtgtt cggcaccatc tgcctcctgg gcatcatcgg gaactccacg     180

gtcatcttcg cggtcgtgaa gaagtccaag ctgcactggt gcaacaacgt ccccgacatc     240

ttcatcatca acctctcggt agtagatctc ctctttctcc tgggcatgcc cttcatgatc     300

caccagctca tgggcaatgg ggtgtggcac tttggggaga ccatgtgcac cctcatcacg     360

gccatggatg ccaatagtca gttcaccagc acctacatcc tgaccgccat ggccattgac     420

cgctacctgg ccactgtcca ccccatctct tccacgaagt tccggaagcc ctctgtggcc     480

accctggtga tctgcctcct gtgggccctc tccttcatca gcatcacccc tgtgtggctg     540
```

-continued

```
tatgccagac tcatcccctt cccaggaggt gcagtgggct gcggcatacg cctgcccaac    600

ccagacactg acctctactg gttcaccctg taccagtttt tcctggcctt tgccctgcct    660

tttgtggtca tcacagccgc atacgtgagg atcctgcagc gcatgacgtc ctcagtggcc    720

cccgcctccc agcgcagcat ccggctgcgg acaaagaggg tgacccgcac agccatcgcc    780

atctgtctgg tcttctttgt gtgctgggca ccctactatg tgctacagct gacccagttg    840

tccatcagcc gcccgaccct cacctttgtc tacttataca atgcggccat cagcttgggc    900

tatgccaaca gctgcctcaa ccccttgtg tacatcgtgc tctgtgagac gttccggaga    960

gacttgcagt tcttcttcaa cttttgtgat ttccggtctc gggatgatga ttatgaaaca   1020

atagccatgt ccacgatgca cacagatgtt tccaaaactt ctttgaagca agcaagccca   1080

gtcgcattta aaaaaatcaa caacaatgat gataatgaaa aaatctga               1128
```

<210> SEQ ID NO 20
<211> LENGTH: 375
<212> TYPE: PRT
<213> ORGANISM: artificial sequence
<220> FEATURE:
<223> OTHER INFORMATION: human MCH1R/NPY1 C-terminal chimera

<400> SEQUENCE: 20

```
Met Asp Leu Glu Ala Ser Leu Leu Pro Thr Gly Pro Asn Ala Ser Asn
1               5                   10                  15

Thr Ser Asp Gly Pro Asp Asn Leu Thr Ser Ala Gly Ser Pro Pro Arg
            20                  25                  30

Thr Gly Ser Ile Ser Tyr Ile Asn Ile Ile Met Pro Ser Val Phe Gly
        35                  40                  45

Thr Ile Cys Leu Leu Gly Ile Ile Gly Asn Ser Thr Val Ile Phe Ala
    50                  55                  60

Val Val Lys Lys Ser Lys Leu His Trp Cys Asn Asn Val Pro Asp Ile
65                  70                  75                  80

Phe Ile Ile Asn Leu Ser Val Val Asp Leu Leu Phe Leu Leu Gly Met
                85                  90                  95

Pro Phe Met Ile His Gln Leu Met Gly Asn Gly Val Trp His Phe Gly
            100                 105                 110

Glu Thr Met Cys Thr Leu Ile Thr Ala Met Asp Ala Asn Ser Gln Phe
        115                 120                 125

Thr Ser Thr Tyr Ile Leu Thr Ala Met Ala Ile Asp Arg Tyr Leu Ala
    130                 135                 140

Thr Val His Pro Ile Ser Ser Thr Lys Phe Arg Lys Pro Ser Val Ala
145                 150                 155                 160

Thr Leu Val Ile Cys Leu Leu Trp Ala Leu Ser Phe Ile Ser Ile Thr
                165                 170                 175

Pro Val Trp Leu Tyr Ala Arg Leu Ile Pro Phe Pro Gly Gly Ala Val
            180                 185                 190

Gly Cys Gly Ile Arg Leu Pro Asn Pro Asp Thr Asp Leu Tyr Trp Phe
        195                 200                 205

Thr Leu Tyr Gln Phe Phe Leu Ala Phe Ala Leu Pro Phe Val Val Ile
    210                 215                 220

Thr Ala Ala Tyr Val Arg Ile Leu Gln Arg Met Thr Ser Ser Val Ala
225                 230                 235                 240

Pro Ala Ser Gln Arg Ser Ile Arg Leu Arg Thr Lys Arg Val Thr Arg
                245                 250                 255
```

-continued

```
Thr Ala Ile Ala Ile Cys Leu Val Phe Phe Val Cys Trp Ala Pro Tyr
            260                 265                 270

Tyr Val Leu Gln Leu Thr Gln Leu Ser Ile Ser Arg Pro Thr Leu Thr
        275                 280                 285

Phe Val Tyr Leu Tyr Asn Ala Ala Ile Ser Leu Gly Tyr Ala Asn Ser
    290                 295                 300

Cys Leu Asn Pro Phe Val Tyr Ile Val Leu Cys Glu Thr Phe Arg Arg
305                 310                 315                 320

Asp Leu Gln Phe Phe Phe Asn Phe Cys Asp Phe Arg Ser Arg Asp Asp
                325                 330                 335

Asp Tyr Glu Thr Ile Ala Met Ser Thr Met His Thr Asp Val Ser Lys
            340                 345                 350

Thr Ser Leu Lys Gln Ala Ser Pro Val Ala Phe Lys Lys Ile Asn Asn
        355                 360                 365

Asn Asp Asp Asn Glu Lys Ile
    370                 375


<210> SEQ ID NO 21
<211> LENGTH: 6498
<212> TYPE: DNA
<213> ORGANISM: artificial sequence
<220> FEATURE:
<223> OTHER INFORMATION: human MCH1R/human NPY1 IC3 chimera in
      pcDNA3.1Plus (pN105)

<400> SEQUENCE: 21

gacggatcgg gagatctccc gatcccctat ggtcgactct cagtacaatc tgctctgatg      60

ccgcatagtt aagccagtat ctgctccctg cttgtgtgtt ggaggtcgct gagtagtgcg     120

cgagcaaaat ttaagctaca acaaggcaag gcttgaccga caattgcatg aagaatctgc     180

ttagggttag gcgttttgcg ctgcttcgcg atgtacgggc cagatatacg cgttgacatt     240

gattattgac tagttattaa tagtaatcaa ttacggggtc attagttcat agcccatata     300

tggagttccg cgttacataa cttacggtaa atggcccgcc tggctgaccg cccaacgacc     360

cccgcccatt gacgtcaata atgacgtatg ttcccatagt aacgccaata gggactttcc     420

attgacgtca atgggtggac tatttacggt aaactgccca cttggcagta catcaagtgt     480

atcatatgcc aagtacgccc cctattgacg tcaatgacgg taaatggccc gcctggcatt     540

atgcccagta catgacctta tgggactttc ctacttggca gtacatctac gtattagtca     600

tcgctattac catggtgatg cggttttggc agtacatcaa tgggcgtgga tagcggtttg     660

actcacgggg atttccaagt ctccacccca ttgacgtcaa tgggagtttg ttttggcacc     720

aaaatcaacg ggactttcca aaatgtcgta acaactccgc cccattgacg caaatgggcg     780

gtaggcgtgt acggtgggag gtctatataa gcagagctct ctggctaact agagaaccca     840

ctgcttactg gcttatcgaa attaatacga ctcactatag ggagacccaa gctggctagc     900

gtttaaactt aagcttggta ccgagctcgg atccgccccc accatggacc tggaagcctc     960

gctgctgccc actggtccca atgccagcaa cacctctgat ggccccgata acctcacttc    1020

ggcaggatca cctcctcgca cggggagcat ctcctacatc aacatcatca tgccttcggt    1080

gttcggcacc atctgcctcc tgggcatcat cgggaactcc acggtcatct tcgcggtcgt    1140

gaagaagtcc aagctgcact ggtgcaacaa cgtccccgac atcttcatca tcaacctctc    1200

ggtagtagat ctcctctttc tcctgggcat gcccttcatg atccaccagc tcatgggcaa    1260

tggggtgtgg cactttgggg agaccatgtg caccctcatc acggccatgg atgccaatag    1320
```

-continued

```
tcagttcacc agcacctaca tcctgaccgc catggccatt gaccgctacc tggccactgt   1380
ccaccccatc tcttccacga agttccggaa gccctctgtg gccaccctgg tgatctgcct   1440
cctgtgggcc ctctccttca tcagcatcac ccctgtgtgg ctgtatgcca gactcatccc   1500
cttcccagga ggtgcagtgg gctgcggcat acgcctgccc aacccagaca ctgacctcta   1560
ctggttcacc ctgtaccagt ttttcctggc ctttgccctg ccttttgtgg tcatcacagc   1620
cgcatacgtg aggatcctga tacgcctaaa aaggagaaac aacatgatgg acaagatgag   1680
agacaataag tacaggtcca gtgaaaccaa aagggtgacc cgcacagcca tcgccatctg   1740
tctggtcttc tttgtgtgct gggcacccta ctatgtgcta cagctgaccc agttgtccat   1800
cagccgcccg accctcacct ttgtctactt atacaatgcg gccatcagct tgggctatgc   1860
caacagctgc ctcaacccct ttgtgtacat cgtgctctgt gagacgttcc gcaaacgctt   1920
ggtcctgtcg gtgaagcctg cagcccaggg gcagcttcgc gctgtcagca acgctcagac   1980
ggctgacgag gagaggacag aaagcaaagg cacctgatac ttcccctgcc accctgggct   2040
agagcggccg ctcgagtcta gagggcccgt ttaaacccgc tgatcagcct cgactgtgcc   2100
ttctagttgc cagccatctg ttgtttgccc ctcccccgtg ccttccttga ccctggaagg   2160
tgccactccc actgtccttt cctaataaaa tgaggaaatt gcatcgcatt gtctgagtag   2220
gtgtcattct attctggggg gtggggtggg gcaggacagc aagggggagg attgggaaga   2280
caatagcagg catgctgggg atgcggtggg ctctatggct tctgaggcgg aaagaaccag   2340
ctggggctct agggggtatc cccacgcgcc ctgtagcggc gcattaagcg cggcgggtgt   2400
ggtggttacg cgcagcgtga ccgctacact tgccagcgcc ctagcgcccg ctcctttcgc   2460
tttcttccct tcctttctcg ccacgttcgc cggctttccc cgtcaagctc taaatcgggg   2520
catcccttta gggttccgat ttagtgcttt acggcacctc gaccccaaaa aacttgatta   2580
gggtgatggt tcacgtagtg ggccatcgcc ctgatagacg gtttttcgcc ctttgacgtt   2640
ggagtccacg ttctttaata gtggactctt gttccaaact ggaacaacac tcaaccctat   2700
ctcggtctat tcttttgatt tataagggat tttggggatt tcggcctatt ggttaaaaaa   2760
tgagctgatt taacaaaaat ttaacgcgaa ttaattctgt ggaatgtgtg tcagttaggg   2820
tgtggaaagt ccccaggctc cccaggcagg cagaagtatg caaagcatgc atctcaatta   2880
gtcagcaacc aggtgtggaa agtccccagg ctccccagca ggcagaagta tgcaaagcat   2940
gcatctcaat tagtcagcaa ccatagtccc gcccctaact ccgcccatcc cgcccctaac   3000
tccgcccagt tccgcccatt ctccgcccca tggctgacta atttttttta tttatgcaga   3060
ggccgaggcc gcctctgcct ctgagctatt ccagaagtag tgaggaggct tttttggagg   3120
cctaggcttt tgcaaaaagc tcccgggagc ttgtatatcc attttcggat ctgatcaaga   3180
gacaggatga ggatcgtttc gcatgattga acaagatgga ttgcacgcag gttctccggc   3240
cgcttgggtg gagaggctat tcggctatga ctgggcacaa cagacaatcg gctgctctga   3300
tgccgccgtg ttccggctgt cagcgcaggg gcgcccggtt ctttttgtca agaccgacct   3360
gtccggtgcc ctgaatgaac tgcaggacga ggcagcgcgg ctatcgtggc tggccacgac   3420
gggcgttcct tgcgcagctg tgctcgacgt tgtcactgaa gcgggaaggg actggctgct   3480
attgggcgaa gtgccggggc aggatctcct gtcatctcac cttgctcctg ccgagaaagt   3540
atccatcatg gctgatgcaa tgcggcggct gcatacgctt gatccggcta cctgcccatt   3600
cgaccaccaa gcgaaacatc gcatcgagcg agcacgtact cggatggaag ccggtcttgt   3660
cgatcaggat gatctggacg aagagcatca ggggctcgcg ccagccgaac tgttcgccag   3720
```

-continued

```
gctcaaggcg cgcatgcccg acggcgagga tctcgtcgtg acccatggcg atgcctgctt   3780
gccgaatatc atggtggaaa atggccgctt ttctggattc atcgactgtg gccggctggg   3840
tgtggcggac cgctatcagg acatagcgtt ggctacccgt gatattgctg aagagcttgg   3900
cggcgaatgg gctgaccgct tcctcgtgct ttacggtatc gccgctcccg attcgcagcg   3960
catcgccttc tatcgccttc ttgacgagtt cttctgagcg ggactctggg gttcgaaatg   4020
accgaccaag cgacgcccaa cctgccatca cgagatttcg attccaccgc cgccttctat   4080
gaaaggttgg gcttcggaat cgttttccgg gacgccggct ggatgatcct ccagcgcggg   4140
gatctcatgc tggagttctt cgcccacccc aacttgttta ttgcagctta taatggttac   4200
aaataaagca atagcatcac aaatttcaca aataaagcat ttttttcact gcattctagt   4260
tgtggtttgt ccaaactcat caatgtatct tatcatgtct gtataccgtc gacctctagc   4320
tagagcttgg cgtaatcatg gtcatagctg tttcctgtgt gaaattgtta tccgctcaca   4380
attccacaca acatacgagc cggaagcata aagtgtaaag cctggggtgc ctaatgagtg   4440
agctaactca cattaattgc gttgcgctca ctgcccgctt tccagtcggg aaacctgtcg   4500
tgccagctgc attaatgaat cggccaacgc gcggggagag gcggtttgcg tattgggcgc   4560
tcttccgctt cctcgctcac tgactcgctg cgctcggtcg ttcggctgcg gcgagcggta   4620
tcagctcact caaaggcggt aatacggtta tccacagaat caggggataa cgcaggaaag   4680
aacatgtgag caaaaggcca gcaaaaggcc aggaaccgta aaaaggccgc gttgctggcg   4740
tttttccata ggctccgccc ccctgacgag catcacaaaa atcgacgctc aagtcagagg   4800
tggcgaaacc cgacaggact ataaagatac caggcgtttc cccctggaag ctccctcgtg   4860
cgctctcctg ttccgaccct gccgcttacc ggatacctgt ccgcctttct cccttcggga   4920
agcgtggcgc tttctcaatg ctcacgctgt aggtatctca gttcggtgta ggtcgttcgc   4980
tccaagctgg gctgtgtgca cgaacccccc gttcagcccg accgctgcgc cttatccggt   5040
aactatcgtc ttgagtccaa cccggtaaga cacgacttat cgccactggc agcagccact   5100
ggtaacagga ttagcagagc gaggtatgta ggcggtgcta cagagttctt gaagtggtgg   5160
cctaactacg gctacactag aaggacagta tttggtatct gcgctctgct gaagccagtt   5220
accttcggaa aaagagttgg tagctcttga tccggcaaac aaaccaccgc tggtagcggt   5280
ggtttttttg tttgcaagca gcagattacg cgcagaaaaa aaggatctca agaagatcct   5340
ttgatctttt ctacggggtc tgacgctcag tggaacgaaa actcacgtta agggattttg   5400
gtcatgagat tatcaaaaag gatcttcacc tagatccttt taaattaaaa atgaagtttt   5460
aaatcaatct aaagtatata tgagtaaact tggtctgaca gttaccaatg cttaatcagt   5520
gaggcaccta tctcagcgat ctgtctattt cgttcatcca tagttgcctg actccccgtc   5580
gtgtagataa ctacgatacg ggagggctta ccatctggcc ccagtgctgc aatgataccg   5640
cgagacccac gctcaccggc tccagattta tcagcaataa accagccagc cggaagggcc   5700
gagcgcagaa gtggtcctgc aactttatcc gcctccatcc agtctattaa ttgttgccgg   5760
gaagctagag taagtagttc gccagttaat agtttgcgca acgttgttgc cattgctaca   5820
ggcatcgtgg tgtcacgctc gtcgtttggt atggcttcat tcagctccgg ttcccaacga   5880
tcaaggcgag ttacatgatc ccccatgttg tgcaaaaaag cggttagctc cttcggtcct   5940
ccgatcgttg tcagaagtaa gttggccgca gtgttatcac tcatggttat ggcagcactg   6000
cataattctc ttactgtcat gccatccgta agatgctttt ctgtgactgg tgagtactca   6060
```

-continued

```
accaagtcat tctgagaata gtgtatgcgg cgaccgagtt gctcttgccc ggcgtcaata   6120

cgggataata ccgcgccaca tagcagaact ttaaaagtgc tcatcattgg aaaacgttct   6180

tcggggcgaa aactctcaag gatcttaccg ctgttgagat ccagttcgat gtaacccact   6240

cgtgcaccca actgatcttc agcatctttt actttcacca gcgtttctgg gtgagcaaaa   6300

acaggaaggc aaaatgccgc aaaaaaggga ataagggcga cacggaaatg ttgaatactc   6360

atactcttcc tttttcaata ttattgaagc atttatcagg gttattgtct catgagcgga   6420

tacatatttg aatgtattta gaaaaataaa caaatagggg ttccgcgcac atttccccga   6480

aaagtgccac ctgacgtc                                                  6498
```

<210> SEQ ID NO 22
<211> LENGTH: 6582
<212> TYPE: DNA
<213> ORGANISM: artificial sequence
<220> FEATURE:
<223> OTHER INFORMATION: human MCH1R/human NPY1 C-terminal chimera in pcDNA3.1Plus (pN107)

<400> SEQUENCE: 22

```
gacggatcgg gagatctccc gatcccctat ggtcgactct cagtacaatc tgctctgatg     60

ccgcatagtt aagccagtat ctgctccctg cttgtgtgtt ggaggtcgct gagtagtgcg    120

cgagcaaaat ttaagctaca acaaggcaag gcttgaccga caattgcatg aagaatctgc    180

ttagggttag gcgttttgcg ctgcttcgcg atgtacgggc cagatatacg cgttgacatt    240

gattattgac tagttattaa tagtaatcaa ttacggggtc attagttcat agcccatata    300

tggagttccg cgttacataa cttacggtaa atggcccgcc tggctgaccg cccaacgacc    360

cccgcccatt gacgtcaata atgacgtatg ttcccatagt aacgccaata gggactttcc    420

attgacgtca atgggtggac tatttacggt aaactgccca cttggcagta catcaagtgt    480

atcatatgcc aagtacgccc cctattgacg tcaatgacgg taaatggccc gcctggcatt    540

atgcccagta catgacctta tgggactttc ctacttggca gtacatctac gtattagtca    600

tcgctattac catggtgatg cggttttggc agtacatcaa tgggcgtgga tagcggtttg    660

actcacgggg atttccaagt ctccacccca ttgacgtcaa tgggagtttg ttttggcacc    720

aaaatcaacg ggactttcca aaatgtcgta acaactccgc cccattgacg caaatgggcg    780

gtaggcgtgt acggtgggag gtctatataa gcagagctct ctggctaact agagaaccca    840

ctgcttactg gcttatcgaa attaatacga ctcactatag ggagacccaa gctggctagc    900

gtttaaactt aagcttggta ccgagctcgg atccactagt ccagtgtggt ggaattcctg    960

cagcccgggg gatccgcccc caccatggac ctggaagcct cgctgctgcc cactggtccc   1020

aatgccagca acacctctga tggccccgat aacctcactt cggcaggatc acctcctcgc   1080

acggggagca tctcctacat caacatcatc atgccttcgg tgttcggcac catctgcctc   1140

ctgggcatca tcgggaactc cacggtcatc ttcgcggtcg tgaagaagtc caagctgcac   1200

tggtgcaaca acgtccccga catcttcatc atcaacctct cggtagtaga tctcctcttt   1260

ctcctgggca tgcccttcat gatccaccag ctcatgggca atggggtgtg gcactttggg   1320

gagaccatgt gcaccctcat cacggccatg gatgccaata gtcagttcac cagcacctac   1380

atcctgaccg ccatggccat tgaccgctac ctggccactg tccaccccat ctcttccacg   1440

aagttccgga agccctctgt ggccaccctg gtgatctgcc tcctgtgggc cctctccttc   1500

atcagcatca cccctgtgtg gctgtatgcc agactcatcc ccttcccagg aggtgcagtg   1560
```

-continued

```
ggctgcggca tacgcctgcc caacccagac actgacctct actggttcac cctgtaccag   1620
tttttcctgg cctttgccct gccttttgtg gtcatcacag ccgcatacgt gaggatcctg   1680
cagcgcatga cgtcctcagt ggcccccgcc tcccagcgca gcatccggct gcggacaaag   1740
agggtgaccc gcacagccat cgccatctgt ctggtcttct ttgtgtgctg ggcaccctac   1800
tatgtgctac agctgaccca gttgtccatc agccgcccga ccctcacctt tgtctactta   1860
tacaatgcgg ccatcagctt gggctatgcc aacagctgcc tcaacccctt tgtgtacatc   1920
gtgctctgtg agacgttccg gagagacttg cagttcttct tcaacttttg tgatttccgg   1980
tctcgggatg atgattatga aacaatagcc atgtccacga tgcacacaga tgtttccaaa   2040
acttctttga agcaagcaag cccagtcgca tttaaaaaaa tcaacaacaa tgatgataat   2100
gaaaaaatct gaaactactt atagcctgcg gccgctcgag tctagagggc ccgtttaaac   2160
ccgctgatca gcctcgactg tgccttctag ttgccagcca tctgttgttt gcccctcccc   2220
cgtgccttcc ttgaccctgg aaggtgccac tcccactgtc ctttcctaat aaaatgagga   2280
aattgcatcg cattgtctga gtaggtgtca ttctattctg gggggtgggg tggggcagga   2340
cagcaagggg gaggattggg aagacaatag caggcatgct ggggatgcgg tgggctctat   2400
ggcttctgag gcggaaagaa ccagctgggg ctctaggggg tatccccacg cgccctgtag   2460
cggcgcatta agcgcggcgg gtgtggtggt tacgcgcagc gtgaccgcta cacttgccag   2520
cgccctagcg cccgctcctt tcgctttctt cccttccttt ctcgccacgt tcgccggctt   2580
tccccgtcaa gctctaaatc ggggcatccc tttagggttc cgatttagtg ctttacggca   2640
cctcgacccc aaaaaacttg attagggtga tggttcacgt agtgggccat cgccctgata   2700
gacggttttt cgccctttga cgttggagtc cacgttcttt aatagtggac tcttgttcca   2760
aactggaaca acactcaacc ctatctcggt ctattctttt gatttataag ggattttggg   2820
gatttcggcc tattggttaa aaaatgagct gatttaacaa aaatttaacg cgaattaatt   2880
ctgtggaatg tgtgtcagtt agggtgtgga aagtccccag gctccccagg caggcagaag   2940
tatgcaaagc atgcatctca attagtcagc aaccaggtgt ggaaagtccc caggctcccc   3000
agcaggcaga agtatgcaaa gcatgcatct caattagtca gcaaccatag tcccgcccct   3060
aactccgccc atcccgcccc taactccgcc cagttccgcc cattctccgc cccatggctg   3120
actaattttt tttatttatg cagaggccga ggccgcctct gcctctgagc tattccagaa   3180
gtagtgagga ggcttttttg gaggcctagg cttttgcaaa aagctcccgg gagcttgtat   3240
atccattttc ggatctgatc aagagacagg atgaggatcg tttcgcatga ttgaacaaga   3300
tggattgcac gcaggttctc cggccgcttg ggtggagagg ctattcggct atgactgggc   3360
acaacagaca atcggctgct ctgatgccgc cgtgttccgg ctgtcagcgc aggggcgccc   3420
ggttcttttt gtcaagaccg acctgtccgg tgccctgaat gaactgcagg acgaggcagc   3480
gcggctatcg tggctggcca cgacgggcgt tccttgcgca gctgtgctcg acgttgtcac   3540
tgaagcggga agggactggc tgctattggg cgaagtgccg gggcaggatc tcctgtcatc   3600
tcaccttgct cctgccgaga aagtatccat catggctgat gcaatgcggc ggctgcatac   3660
gcttgatccg gctacctgcc cattcgacca ccaagcgaaa catcgcatcg agcgagcacg   3720
tactcggatg gaagccggtc ttgtcgatca ggatgatctg gacgaagagc atcaggggct   3780
cgcgccagcc gaactgttcg ccaggctcaa ggcgcgcatg cccgacggcg aggatctcgt   3840
cgtgacccat ggcgatgcct gcttgccgaa tatcatggtg gaaaatggcc gcttttctgg   3900
attcatcgac tgtggccggc tgggtgtggc ggaccgctat caggacatag cgttggctac   3960
```

-continued

```
ccgtgatatt gctgaagagc ttggcggcga atgggctgac cgcttcctcg tgctttacgg   4020
tatcgccgct cccgattcgc agcgcatcgc cttctatcgc cttcttgacg agttcttctg   4080
agcgggactc tggggttcga aatgaccgac caagcgacgc ccaacctgcc atcacgagat   4140
ttcgattcca ccgccgcctt ctatgaaagg ttgggcttcg gaatcgtttt ccgggacgcc   4200
ggctggatga tcctccagcg cggggatctc atgctggagt tcttcgccca ccccaacttg   4260
tttattgcag cttataatgg ttacaaataa agcaatagca tcacaaattt cacaaataaa   4320
gcattttttt cactgcattc tagttgtggt ttgtccaaac tcatcaatgt atcttatcat   4380
gtctgtatac cgtcgacctc tagctagagc ttggcgtaat catggtcata gctgtttcct   4440
gtgtgaaatt gttatccgct cacaattcca cacaacatac gagccggaag cataaagtgt   4500
aaagcctggg gtgcctaatg agtgagctaa ctcacattaa ttgcgttgcg ctcactgccc   4560
gctttccagt cgggaaacct gtcgtgccag ctgcattaat gaatcggcca acgcgcgggg   4620
agaggcggtt tgcgtattgg gcgctcttcc gcttcctcgc tcactgactc gctgcgctcg   4680
gtcgttcggc tgcggcgagc ggtatcagct cactcaaagg cggtaatacg gttatccaca   4740
gaatcagggg ataacgcagg aaagaacatg tgagcaaaag gccagcaaaa ggccaggaac   4800
cgtaaaaagg ccgcgttgct ggcgtttttc cataggctcc gcccccctga cgagcatcac   4860
aaaaatcgac gctcaagtca gaggtggcga aacccgacag gactataaag ataccaggcg   4920
tttccccctg gaagctccct cgtgcgctct cctgttccga ccctgccgct taccggatac   4980
ctgtccgcct ttctcccttc gggaagcgtg gcgctttctc aatgctcacg ctgtaggtat   5040
ctcagttcgg tgtaggtcgt tcgctccaag ctgggctgtg tgcacgaacc ccccgttcag   5100
cccgaccgct gcgccttatc cggtaactat cgtcttgagt ccaacccggt aagacacgac   5160
ttatcgccac tggcagcagc cactggtaac aggattagca gagcgaggta tgtaggcggt   5220
gctacagagt tcttgaagtg gtggcctaac tacggctaca ctagaaggac agtatttggt   5280
atctgcgctc tgctgaagcc agttaccttc ggaaaaagag ttggtagctc ttgatccggc   5340
aaacaaacca ccgctggtag cggtggtttt tttgtttgca agcagcagat tacgcgcaga   5400
aaaaaaggat ctcaagaaga tcctttgatc ttttctacgg ggtctgacgc tcagtggaac   5460
gaaaactcac gttaagggat tttggtcatg agattatcaa aaaggatctt cacctagatc   5520
cttttaaatt aaaaatgaag ttttaaatca atctaaagta tatatgagta aacttggtct   5580
gacagttacc aatgcttaat cagtgaggca cctatctcag cgatctgtct atttcgttca   5640
tccatagttg cctgactccc cgtcgtgtag ataactacga tacgggaggg cttaccatct   5700
ggccccagtg ctgcaatgat accgcgagac ccacgctcac cggctccaga tttatcagca   5760
ataaaccagc cagccggaag ggccgagcgc agaagtggtc ctgcaacttt atccgcctcc   5820
atccagtcta ttaattgttg ccgggaagct agagtaagta gttcgccagt taatagtttg   5880
cgcaacgttg ttgccattgc tacaggcatc gtggtgtcac gctcgtcgtt tggtatggct   5940
tcattcagct ccggttccca acgatcaagg cgagttacat gatcccccat gttgtgcaaa   6000
aaagcggtta gctccttcgg tcctccgatc gttgtcagaa gtaagttggc cgcagtgtta   6060
tcactcatgg ttatggcagc actgcataat tctcttactg tcatgccatc cgtaagatgc   6120
ttttctgtga ctggtgagta ctcaaccaag tcattctgag aatagtgtat gcggcgaccg   6180
agttgctctt gcccggcgtc aatacgggat aataccgcgc cacatagcag aactttaaaa   6240
gtgctcatca ttggaaaacg ttcttcgggg cgaaaactct caaggatctt accgctgttg   6300
```

-continued

```
agatccagtt cgatgtaacc cactcgtgca cccaactgat cttcagcatc ttttactttc   6360

accagcgttt ctgggtgagc aaaaacagga aggcaaaatg ccgcaaaaaa gggaataagg   6420

gcgacacgga aatgttgaat actcatactc ttcctttttc aatattattg aagcatttat   6480

cagggttatt gtctcatgag cggatacata tttgaatgta tttagaaaaa taaacaaata   6540

ggggttccgc gcacatttcc ccgaaaagtg ccacctgacg tc                      6582
```

<210> SEQ ID NO 23
<211> LENGTH: 2305
<212> TYPE: DNA
<213> ORGANISM: homo sapiens

<400> SEQUENCE: 23

```
gaattcatgc cgcgtttctg tgttggacag gggtgacttt gtgccggatg gcttctgtgt     60

gagagcgcgc gcgagtgtgc atgtcggtga gctgggaggg tgtgtctcag tgtctatggc    120

tgtggttcgg tataagtcta agcatgtctg ccagggtgta tttgtgcctg tatgtgcgtg    180

cctcggtggg cactctcgtt tccttccgaa tgtggggcag tgccggtgtg ctgccctctg    240

ccttgagacc tcaagccgcg caggcgccca gggcaggcag gtagcggcca cagaagagcc    300

aaaagctccc gggttggctg gtaagcacac cacctccagc tttagccctc tggggccagc    360

cagggtagcc gggaagcagt ggtggcccgc cctccaggga gcagttgggc cccgcccggg    420

ccagcctcag gagaaggagg gcgaggggag gggagggaaa ggggaggagt gcctcgcccc    480

ttcgcggctg ccggcgtgcc attggccgaa agttcccgta cgtcacggcg agggcagttc    540

ccctaaagtc ctgtgcacat aacgggcaga acgcactgcg aagcggcttc ttcagagcac    600

gggctggaac tggcaggcac cgcgagcccc tagcacccga caagctgagt gtgcaggacg    660

agtccccacc acacccacac cacagccgct gaatgaggct tccaggcgtc cgctcgcggc    720

ccgcagagcc ccgccgtggg tccgcctgct gaggcgcccc cagccagtgc gcttacctgc    780

cagactgcgc gccatggggc aacccgggaa cggcagcgcc ttcttgctgg cacccaatag    840

aagccatgcg ccggaccacg acgtcacgca gcaaagggac gaggtgtggg tggtgggcat    900

gggcatcgtc atgtctctca tcgtcctggc catcgtgttt ggcaatgtgc tggtcatcac    960

agccattgcc aagttcgagc gtctgcagac ggtcaccaac tacttcatca cttcactggc   1020

ctgtgctgat ctggtcatgg gcctggcagt ggtgcccttt ggggccgccc atattcttat   1080

gaaaatgtgg acttttggca acttctggtg cgagttttgg acttccattg atgtgctgtg   1140

cgtcacggcc agcattgaga ccctgtgcgt gatcgcagtg gatcgctact ttgccattac   1200

ttcacctttc aagtaccaga gcctgctgac caagaataag gcccgggtga tcattctgat   1260

ggtgtggatt gtgtcaggcc ttacctcctt cttgcccatt cagatgcact ggtaccgggc   1320

cacccaccag gaagccatca actgctatgc caatgagacc tgctgtgact tcttcacgaa   1380

ccaagcctat gccattgcct cttccatcgt gtccttctac gttcccctgg tgatcatggt   1440

cttcgtctac tccagggtct ttcaggaggc caaaaggcag ctccagaaga ttgacaaatc   1500

tgagggccgc ttccatgtcc agaaccttag ccaggtggag caggatgggc ggacggggca   1560

tggactccgc agatcttcca agttctgctt gaaggagcac aaagccctca agacgttagg   1620

catcatcatg ggcactttca ccctctgctg gctgcccttc ttcatcgtta acattgtgca   1680

tgtgatccag gataacctca tccgtaagga agtttacatc ctcctaaatt ggataggcta   1740

tgtcaattct ggtttcaatc cccttatcta ctgccggagc ccagatttca ggattgcctt   1800

ccaggagctt ctgtgcctgc gcaggtcttc tttgaaggcc tatgggaatg gctactccag   1860
```

```
caacggcaac acaggggagc agagtggata tcacgtggaa caggagaaag aaaataaact   1920

gctgtgtgaa gacctcccag gcacggaaga ctttgtgggc catcaaggta ctgtgcctag   1980

cgataacatt gattcacaag ggaggaattg tagtacaaat gactcactgc tgtaaagcag   2040

tttttctact tttaaagacc ccccccccca acagaacact aaacagacta tttaacttga   2100

gggtaataaa cttagaataa aattgtaaaa ttgtatagag atatgcagaa ggaagggcat   2160

ccttctgcct tttttatttt tttaagctgt aaaaagagag aaaacttatt tgagtgatta   2220

tttgttattt gtacagttca gttcctcttt gcatggaatt tgtaagttta tgtctaaaga   2280

gctttagtcc tagaggacct gagtc                                         2305


<210> SEQ ID NO 24
<211> LENGTH: 413
<212> TYPE: PRT
<213> ORGANISM: Homo sapiens

<400> SEQUENCE: 24

Met Gly Gln Pro Gly Asn Gly Ser Ala Phe Leu Leu Ala Pro Asn Arg
1               5                   10                  15

Ser His Ala Pro Asp His Asp Val Thr Gln Gln Arg Asp Glu Val Trp
            20                  25                  30

Val Val Gly Met Gly Ile Val Met Ser Leu Ile Val Leu Ala Ile Val
        35                  40                  45

Phe Gly Asn Val Leu Val Ile Thr Ala Ile Ala Lys Phe Glu Arg Leu
    50                  55                  60

Gln Thr Val Thr Asn Tyr Phe Ile Thr Ser Leu Ala Cys Ala Asp Leu
65                  70                  75                  80

Val Met Gly Leu Ala Val Val Pro Phe Gly Ala Ala His Ile Leu Met
                85                  90                  95

Lys Met Trp Thr Phe Gly Asn Phe Trp Cys Glu Phe Trp Thr Ser Ile
            100                 105                 110

Asp Val Leu Cys Val Thr Ala Ser Ile Glu Thr Leu Cys Val Ile Ala
        115                 120                 125

Val Asp Arg Tyr Phe Ala Ile Thr Ser Pro Phe Lys Tyr Gln Ser Leu
    130                 135                 140

Leu Thr Lys Asn Lys Ala Arg Val Ile Ile Leu Met Val Trp Ile Val
145                 150                 155                 160

Ser Gly Leu Thr Ser Phe Leu Pro Ile Gln Met His Trp Tyr Arg Ala
                165                 170                 175

Thr His Gln Glu Ala Ile Asn Cys Tyr Ala Asn Glu Thr Cys Cys Asp
            180                 185                 190

Phe Phe Thr Asn Gln Ala Tyr Ala Ile Ala Ser Ser Ile Val Ser Phe
        195                 200                 205

Tyr Val Pro Leu Val Ile Met Val Phe Val Tyr Ser Arg Val Phe Gln
    210                 215                 220

Glu Ala Lys Arg Gln Leu Gln Lys Ile Asp Lys Ser Glu Gly Arg Phe
225                 230                 235                 240

His Val Gln Asn Leu Ser Gln Val Glu Gln Asp Gly Arg Thr Gly His
                245                 250                 255

Gly Leu Arg Arg Ser Ser Lys Phe Cys Leu Lys Glu His Lys Ala Leu
            260                 265                 270

Lys Thr Leu Gly Ile Ile Met Gly Thr Phe Thr Leu Cys Trp Leu Pro
        275                 280                 285
```

-continued

```
Phe Phe Ile Val Asn Ile Val His Val Ile Gln Asp Asn Leu Ile Arg
    290                 295                 300

Lys Glu Val Tyr Ile Leu Leu Asn Trp Ile Gly Tyr Val Asn Ser Gly
305                 310                 315                 320

Phe Asn Pro Leu Ile Tyr Cys Arg Ser Pro Asp Phe Arg Ile Ala Phe
                325                 330                 335

Gln Glu Leu Leu Cys Leu Arg Arg Ser Ser Leu Lys Ala Tyr Gly Asn
            340                 345                 350

Gly Tyr Ser Ser Asn Gly Asn Thr Gly Glu Gln Ser Gly Tyr His Val
        355                 360                 365

Glu Gln Glu Lys Glu Asn Lys Leu Leu Cys Glu Asp Leu Pro Gly Thr
    370                 375                 380

Glu Asp Phe Val Gly His Gln Gly Thr Val Pro Ser Asp Asn Ile Asp
385                 390                 395                 400

Ser Gln Gly Arg Asn Cys Ser Thr Asn Asp Ser Leu Leu
                405                 410


<210> SEQ ID NO 25
<211> LENGTH: 29
<212> TYPE: DNA
<213> ORGANISM: artificial sequence
<220> FEATURE:
<223> OTHER INFORMATION: human beta-2 adrenergic receptor forward primer

<400> SEQUENCE: 25

tgttccggag ttctttgaag gcctatggg                                        29


<210> SEQ ID NO 26
<211> LENGTH: 25
<212> TYPE: DNA
<213> ORGANISM: artificial sequence
<220> FEATURE:
<223> OTHER INFORMATION: human beta-2 adrenergic receptor reverse primer

<400> SEQUENCE: 26

gctctagagc ttacagcagt gagtc                                            25


<210> SEQ ID NO 27
<211> LENGTH: 1167
<212> TYPE: DNA
<213> ORGANISM: artificial sequence
<220> FEATURE:
<223> OTHER INFORMATION: human MCH1R/beta-2 adrenergic receptor
      C-terminal chimera coding
      sequence

<400> SEQUENCE: 27

atggacctgg aagcctcgct gctgcccact ggtcccaatg ccagcaacac ctctgatggc     60

cccgataacc tcacttcggc aggatcacct cctcgcacgg ggagcatctc ctacatcaac    120

atcatcatgc cttcggtgtt cggcaccatc tgcctcctgg gcatcatcgg gaactccacg    180

gtcatcttcg cggtcgtgaa gaagtccaag ctgcactggt gcaacaacgt ccccgacatc    240

ttcatcatca acctctcggt agtagatctc ctctttctcc tgggcatgcc cttcatgatc    300

caccagctca tgggcaatgg ggtgtggcac tttggggaga ccatgtgcac cctcatcacg    360

gccatggatg ccaatagtca gttcaccagc acctacatcc tgaccgccat ggccattgac    420

cgctacctgg ccactgtcca ccccatctct tccacgaagt tccggaagcc ctctgtggcc    480

accctggtga tctgcctcct gtgggccctc tccttcatca gcatcacccc tgtgtggctg    540

tatgccagac tcatcccctt cccaggaggt gcagtgggct gcggcatacg cctgcccaac    600
```

```
ccagacactg acctctactg gttcaccctg taccagtttt tcctggcctt tgccctgcct    660

tttgtggtca tcacagccgc atacgtgagg atcctgcagc gcatgacgtc ctcagtggcc    720

cccgcctccc agcgcagcat ccggctgcgg acaaagaggg tgacccgcac agccatcgcc    780

atctgtctgg tcttctttgt gtgctgggca ccctactatg tgctacagct gacccagttg    840

tccatcagcc gcccgaccct caccttttgtc tacttataca atgcggccat cagcttgggc    900

tatgccaaca gctgcctcaa ccccttttgtg tacatcgtgc tctgtgagac gttccggagt    960

tctttgaagg cctatgggaa tggctactcc agcaacggca acacagggga gcagagtgga   1020

tatcacgtgg aacaggagaa agaaaataaa ctgctgtgtg aagacctccc aggcacggaa   1080

gactttgtgg gccatcaagg tactgtgcct agcgataaca ttgattcaca agggaggaat   1140

tgtagtacaa atgactcact gctgtaa                                       1167
```

<210> SEQ ID NO 28
<211> LENGTH: 388
<212> TYPE: PRT
<213> ORGANISM: artificial sequence
<220> FEATURE:
<223> OTHER INFORMATION: human MCH1R/human beta-2 adrenergic receptor C-terminal chimera protein sequence

<400> SEQUENCE: 28

```
Met Asp Leu Glu Ala Ser Leu Leu Pro Thr Gly Pro Asn Ala Ser Asn
1               5                   10                  15

Thr Ser Asp Gly Pro Asp Asn Leu Thr Ser Ala Gly Ser Pro Pro Arg
            20                  25                  30

Thr Gly Ser Ile Ser Tyr Ile Asn Ile Ile Met Pro Ser Val Phe Gly
        35                  40                  45

Thr Ile Cys Leu Leu Gly Ile Ile Gly Asn Ser Thr Val Ile Phe Ala
    50                  55                  60

Val Val Lys Lys Ser Lys Leu His Trp Cys Asn Asn Val Pro Asp Ile
65                  70                  75                  80

Phe Ile Ile Asn Leu Ser Val Val Asp Leu Leu Phe Leu Leu Gly Met
                85                  90                  95

Pro Phe Met Ile His Gln Leu Met Gly Asn Gly Val Trp His Phe Gly
            100                 105                 110

Glu Thr Met Cys Thr Leu Ile Thr Ala Met Asp Ala Asn Ser Gln Phe
        115                 120                 125

Thr Ser Thr Tyr Ile Leu Thr Ala Met Ala Ile Asp Arg Tyr Leu Ala
    130                 135                 140

Thr Val His Pro Ile Ser Ser Thr Lys Phe Arg Lys Pro Ser Val Ala
145                 150                 155                 160

Thr Leu Val Ile Cys Leu Leu Trp Ala Leu Ser Phe Ile Ser Ile Thr
                165                 170                 175

Pro Val Trp Leu Tyr Ala Arg Leu Ile Pro Phe Pro Gly Gly Ala Val
            180                 185                 190

Gly Cys Gly Ile Arg Leu Pro Asn Pro Asp Thr Asp Leu Tyr Trp Phe
        195                 200                 205

Thr Leu Tyr Gln Phe Phe Leu Ala Phe Ala Leu Pro Phe Val Val Ile
    210                 215                 220

Thr Ala Ala Tyr Val Arg Ile Leu Gln Arg Met Thr Ser Ser Val Ala
225                 230                 235                 240

Pro Ala Ser Gln Arg Ser Ile Arg Leu Arg Thr Lys Arg Val Thr Arg
                245                 250                 255
```

-continued

```
Thr Ala Ile Ala Ile Cys Leu Val Phe Phe Val Cys Trp Ala Pro Tyr
            260                 265                 270

Tyr Val Leu Gln Leu Thr Gln Leu Ser Ile Ser Arg Pro Thr Leu Thr
        275                 280                 285

Phe Val Tyr Leu Tyr Asn Ala Ala Ile Ser Leu Gly Tyr Ala Asn Ser
    290                 295                 300

Cys Leu Asn Pro Phe Val Tyr Ile Val Leu Cys Glu Thr Phe Arg Ser
305                 310                 315                 320

Ser Leu Lys Ala Tyr Gly Asn Gly Tyr Ser Ser Asn Gly Asn Thr Gly
                325                 330                 335

Glu Gln Ser Gly Tyr His Val Glu Gln Glu Lys Glu Asn Lys Leu Leu
            340                 345                 350

Cys Glu Asp Leu Pro Gly Thr Glu Asp Phe Val Gly His Gln Gly Thr
        355                 360                 365

Val Pro Ser Asp Asn Ile Asp Ser Gln Gly Arg Asn Cys Ser Thr Asn
    370                 375                 380

Asp Ser Leu Leu
385
```

<210> SEQ ID NO 29
<211> LENGTH: 6595
<212> TYPE: DNA
<213> ORGANISM: artificial sequence
<220> FEATURE:
<223> OTHER INFORMATION: human MCH1R/human beta-2 adrenergic receptor in pcDNA3.1Plus(pN125)

<400> SEQUENCE: 29

```
gacggatcgg gagatctccc gatcccctat ggtcgactct cagtacaatc tgctctgatg      60

ccgcatagtt aagccagtat ctgctccctg cttgtgtgtt ggaggtcgct gagtagtgcg     120

cgagcaaaat ttaagctaca acaaggcaag gcttgaccga caattgcatg aagaatctgc     180

ttagggttag gcgttttgcg ctgcttcgcg atgtacgggc cagatatacg cgttgacatt     240

gattattgac tagttattaa tagtaatcaa ttacggggtc attagttcat agcccatata     300

tggagttccg cgttacataa cttacggtaa atggcccgcc tggctgaccg cccaacgacc     360

cccgcccatt gacgtcaata atgacgtatg ttcccatagt aacgccaata gggactttcc     420

attgacgtca atgggtggac tatttacggt aaactgccca cttggcagta catcaagtgt     480

atcatatgcc aagtacgccc cctattgacg tcaatgacgg taaatggccc gcctggcatt     540

atgcccagta catgacctta tgggactttc ctacttggca gtacatctac gtattagtca     600

tcgctattac catggtgatg cggttttggc agtacatcaa tgggcgtgga tagcggtttg     660

actcacgggg atttccaagt ctccacccca ttgacgtcaa tgggagtttg ttttggcacc     720

aaaatcaacg ggactttcca aaatgtcgta acaactccgc cccattgacg caaatgggcg     780

gtaggcgtgt acggtgggag gtctatataa gcagagctct ctggctaact agagaaccca     840

ctgcttactg gcttatcgaa attaatacga ctcactatag ggagacccaa gctggctagc     900

gtttaaactt aagcttggta ccgagctcgg atccactagt ccagtgtggt ggaattcctg     960

cagcccgggg gatccgcccc caccatggac ctggaagcct cgctgctgcc cactggtccc    1020

aatgccagca acacctctga tggccccgat aacctcactt cggcaggatc acctcctcgc    1080

acggggagca tctcctacat caacatcatc atgccttcgg tgttcggcac catctgcctc    1140

ctgggcatca tcgggaactc cacggtcatc ttcgcggtcg tgaagaagtc caagctgcac    1200
```

-continued tggtgcaaca acgtccccga catcttcatc atcaacctct cggtagtaga tctcctcttt 1260
ctcctgggca tgcccttcat gatccaccag ctcatgggca atggggtgtg gcactttggg 1320
gagaccatgt gcaccctcat cacggccatg gatgccaata gtcagttcac cagcacctac 1380
atcctgaccg ccatggccat tgaccgctac ctggccactg tccaccccat ctcttccacg 1440
aagttccgga agccctctgt ggccaccctg gtgatctgcc tcctgtgggc cctctccttc 1500
atcagcatca cccctgtgtg gctgtatgcc agactcatcc ccttcccagg aggtgcagtg 1560
ggctgcggca tacgcctgcc caacccagac actgacctct actggttcac cctgtaccag 1620
tttttcctgg cctttgccct gccttttgtg gtcatcacag ccgcatacgt gaggatcctg 1680
cagcgcatga cgtcctcagt ggcccccgcc tcccagcgca gcatccggct gcggacaaag 1740
agggtgaccc gcacagccat cgccatctgt ctggtcttct ttgtgtgctg ggcaccctac 1800
tatgtgctac agctgaccca gttgtccatc agccgcccga ccctcacctt tgtctactta 1860
tacaatgcgg ccatcagctt gggctatgcc aacagctgcc tcaacccctt tgtgtacatc 1920
gtgctctgtg agacgttccg gagttctttg aaggcctatg ggaatggcta ctccagcaac 1980
ggcaacacag gggagcagag tggatatcac gtggaacagg agaaagaaaa taaactgctg 2040
tgtgaagacc tcccaggcac ggaagacttt gtgggccatc aaggtactgt gcctagcgat 2100
aacattgatt cacaagggag gaattgtagt acaaatgact cactgctgta agctctagag 2160
ggcccgttta aacccgctga tcagcctcga ctgtgccttc tagttgccag ccatctgttg 2220
tttgcccctc ccccgtgcct tccttgaccc tggaaggtgc cactcccact gtcctttcct 2280
aataaaatga ggaaattgca tcgcattgtc tgagtaggtg tcattctatt ctggggggtg 2340
gggtggggca ggacagcaag ggggaggatt gggaagacaa tagcaggcat gctggggatg 2400
cggtgggctc tatggcttct gaggcggaaa gaaccagctg gggctctagg gggtatcccc 2460
acgcgccctg tagcggcgca ttaagcgcgg cgggtgtggt ggttacgcgc agcgtgaccg 2520
ctacacttgc cagcgcccta gcgcccgctc ctttcgcttt cttcccttcc tttctcgcca 2580
cgttcgccgg ctttccccgt caagctctaa atcggggcat ccctttaggg ttccgattta 2640
gtgctttacg gcacctcgac cccaaaaaac ttgattaggg tgatggttca cgtagtgggc 2700
catcgccctg atagacggtt tttcgccctt tgacgttgga gtccacgttc tttaatagtg 2760
gactcttgtt ccaaactgga acaacactca accctatctc ggtctattct tttgatttat 2820
aagggatttt ggggatttcg gcctattggt taaaaaatga gctgatttaa caaaaattta 2880
acgcgaatta attctgtgga atgtgtgtca gttagggtgt ggaaagtccc caggctcccc 2940
aggcaggcag aagtatgcaa agcatgcatc tcaattagtc agcaaccagg tgtggaaagt 3000
ccccaggctc cccagcaggc agaagtatgc aaagcatgca tctcaattag tcagcaacca 3060
tagtcccgcc cctaactccg cccatcccgc ccctaactcc gcccagttcc gcccattctc 3120
cgccccatgg ctgactaatt ttttttattt atgcagaggc cgaggccgcc tctgcctctg 3180
agctattcca gaagtagtga ggaggctttt ttggaggcct aggcttttgc aaaaagctcc 3240
cgggagcttg tatatccatt ttcggatctg atcaagagac aggatgagga tcgtttcgca 3300
tgattgaaca agatggattg cacgcaggtt ctccggccgc ttgggtggag aggctattcg 3360
gctatgactg ggcacaacag acaatcggct gctctgatgc cgccgtgttc cggctgtcag 3420
cgcaggggcg cccggttctt tttgtcaaga ccgacctgtc cggtgccctg aatgaactgc 3480
aggacgaggc agcgcggcta tcgtggctgg ccacgacggg cgttccttgc gcagctgtgc 3540
tcgacgttgt cactgaagcg ggaagggact ggctgctatt gggcgaagtg ccggggcagg 3600

-continued

```
atctcctgtc atctcacctt gctcctgccg agaaagtatc catcatggct gatgcaatgc   3660
ggcggctgca tacgcttgat ccggctacct gcccattcga ccaccaagcg aaacatcgca   3720
tcgagcgagc acgtactcgg atggaagccg gtcttgtcga tcaggatgat ctggacgaag   3780
agcatcaggg gctcgcgcca gccgaactgt tcgccaggct caaggcgcgc atgcccgacg   3840
gcgaggatct cgtcgtgacc catggcgatg cctgcttgcc gaatatcatg gtggaaaatg   3900
gccgcttttc tggattcatc gactgtggcc ggctgggtgt ggcggaccgc tatcaggaca   3960
tagcgttggc tacccgtgat attgctgaag agcttggcgg cgaatgggct gaccgcttcc   4020
tcgtgcttta cggtatcgcc gctcccgatt cgcagcgcat cgccttctat cgccttcttg   4080
acgagttctt ctgagcggga ctctggggtt cgaaatgacc gaccaagcga cgcccaacct   4140
gccatcacga gatttcgatt ccaccgccgc cttctatgaa aggttgggct tcggaatcgt   4200
tttccgggac gccggctgga tgatcctcca gcgcggggat ctcatgctgg agttcttcgc   4260
ccaccccaac ttgtttattg cagcttataa tggttacaaa taaagcaata gcatcacaaa   4320
tttcacaaat aaagcatttt tttcactgca ttctagttgt ggtttgtcca aactcatcaa   4380
tgtatcttat catgtctgta taccgtcgac ctctagctag agcttggcgt aatcatggtc   4440
atagctgttt cctgtgtgaa attgttatcc gctcacaatt ccacacaaca tacgagccgg   4500
aagcataaag tgtaaagcct ggggtgccta atgagtgagc taactcacat taattgcgtt   4560
gcgctcactg cccgctttcc agtcgggaaa cctgtcgtgc cagctgcatt aatgaatcgg   4620
ccaacgcgcg gggagaggcg gtttgcgtat tgggcgctct tccgcttcct cgctcactga   4680
ctcgctgcgc tcggtcgttc ggctgcggcg agcggtatca gctcactcaa aggcggtaat   4740
acggttatcc acagaatcag gggataacgc aggaaagaac atgtgagcaa aaggccagca   4800
aaaggccagg aaccgtaaaa aggccgcgtt gctggcgttt ttccataggc tccgcccccc   4860
tgacgagcat cacaaaaatc gacgctcaag tcagaggtgg cgaaacccga caggactata   4920
aagataccag gcgtttcccc ctggaagctc cctcgtgcgc tctcctgttc cgaccctgcc   4980
gcttaccgga tacctgtccg cctttctccc ttcgggaagc gtggcgcttt ctcaatgctc   5040
acgctgtagg tatctcagtt cggtgtaggt cgttcgctcc aagctgggct gtgtgcacga   5100
accccccgtt cagcccgacc gctgcgcctt atccggtaac tatcgtcttg agtccaaccc   5160
ggtaagacac gacttatcgc cactggcagc agccactggt aacaggatta gcagagcgag   5220
gtatgtaggc ggtgctacag agttcttgaa gtggtggcct aactacggct acactagaag   5280
gacagtattt ggtatctgcg ctctgctgaa gccagttacc ttcggaaaaa gagttggtag   5340
ctcttgatcc ggcaaacaaa ccaccgctgg tagcggtggt ttttttgttt gcaagcagca   5400
gattacgcgc agaaaaaaag gatctcaaga agatcctttg atcttttcta cggggtctga   5460
cgctcagtgg aacgaaaact cacgttaagg gattttggtc atgagattat caaaaaggat   5520
cttcacctag atccttttaa attaaaaatg aagttttaaa tcaatctaaa gtatatatga   5580
gtaaacttgg tctgacagtt accaatgctt aatcagtgag gcacctatct cagcgatctg   5640
tctatttcgt tcatccatag ttgcctgact ccccgtcgtg tagataacta cgatacggga   5700
gggcttacca tctggcccca gtgctgcaat gataccgcga gacccacgct caccggctcc   5760
agatttatca gcaataaacc agccagccgg aagggccgag cgcagaagtg gtcctgcaac   5820
tttatccgcc tccatccagt ctattaattg ttgccgggaa gctagagtaa gtagttcgcc   5880
agttaatagt ttgcgcaacg ttgttgccat tgctacaggc atcgtggtgt cacgctcgtc   5940
```

-continued

```
gtttggtatg gcttcattca gctccggttc ccaacgatca aggcgagtta catgatcccc   6000

catgttgtgc aaaaaagcgg ttagctcctt cggtcctccg atcgttgtca gaagtaagtt   6060

ggccgcagtg ttatcactca tggttatggc agcactgcat aattctctta ctgtcatgcc   6120

atccgtaaga tgcttttctg tgactggtga gtactcaacc aagtcattct gagaatagtg   6180

tatgcggcga ccgagttgct cttgcccggc gtcaatacgg gataataccg cgccacatag   6240

cagaacttta aaagtgctca tcattggaaa acgttcttcg gggcgaaaac tctcaaggat   6300

cttaccgctg ttgagatcca gttcgatgta acccactcgt gcacccaact gatcttcagc   6360

atcttttact ttcaccagcg tttctgggtg agcaaaaaca ggaaggcaaa atgccgcaaa   6420

aaagggaata agggcgacac ggaaatgttg aatactcata ctcttccttt ttcaatatta   6480

ttgaagcatt tatcagggtt attgtctcat gagcggatac atatttgaat gtatttagaa   6540

aaataaacaa ataggggttc cgcgcacatt tccccgaaaa gtgccacctg acgtc        6595
```

<210> SEQ ID NO 30
<211> LENGTH: 31
<212> TYPE: PRT
<213> ORGANISM: Macaca fascicularis

<400> SEQUENCE: 30

```
Pro Pro Arg Ser Gly Ser Val Ser Thr Ile Asn Ile Ile Met Pro Ser
1               5                   10                  15

Val Phe Gly Thr Ile Cys Leu Leu Gly Ile Ile Gly Asn Ser Met
            20                  25                  30
```

<210> SEQ ID NO 31
<211> LENGTH: 23
<212> TYPE: DNA
<213> ORGANISM: artificial sequence
<220> FEATURE:
<223> OTHER INFORMATION: human MCH1r forward primer

<400> SEQUENCE: 31

```
ccaccatgga cctggaagcc tcg                                             23
```

<210> SEQ ID NO 32
<211> LENGTH: 20
<212> TYPE: DNA
<213> ORGANISM: artificial sequence
<220> FEATURE:
<223> OTHER INFORMATION: human MCH1R reverse primer

<400> SEQUENCE: 32

```
agggtggcag gggaagtatc                                                 20
```

<210> SEQ ID NO 33
<211> LENGTH: 1023
<212> TYPE: DNA
<213> ORGANISM: Macaca fascicularis

<400> SEQUENCE: 33

```
atgaatccat ttcactcatc ttgttggaac acctctgccg aactttcaaa caaatcctgg     60

aataaagagt ttgcttatca aactgccagt gttgtagata cagtcatcct cccttccatg    120

attgggatta tctgttcaac agggctggtt ggcaacatcc tcattgtatt cactataata    180

aggtccagaa aaaaaacagt ccctgacatc tatatctgca acctggctgt ggctgatttg    240

gtccacatcg ttggaatgcc ttttcttatt caccagtggg cccgaggggg agagtgggta    300

tttgggggc ctctctgcac catcatcaca tccctggata cttgtaacca atttgcctgt     360
```

```
agtgccatca tgactgtaat gagtgtggac aggtactttg ccctcgtcca accatttcga     420

ctgacgagtt ggaggacaag gtacaagacc atccggatca atttgggcct ttgggcagct     480

tcctttatcc tggcattgcc tgtctggatc tactcgaagg tcatcaaatt taaagacggt     540

gtcgagagtt gtgcttttga tttgacatcc cctgacgatg tactctggta tacactttat     600

ttgacaataa caactttctt tttccctcta cccttgattt tggtgtgcta tattttaatt     660

ttatgctata cttgggagat gtatcaacag aataaggatg ccagatgttg caatcccagc     720

gtaccaaaac agagagtgat gaagttgaca aagatggtgc tggtgctggt ggcagtcttt     780

atcctaagtg ctgcccctta tcatgtgata caactggtga acttacagat ggaacagccc     840

acactggcct tctatgtggg ttattacctc tccatctgtc tcagctatgc cagcagcagc     900

attaaccctt ttctctacat cctgctgagt ggaaatttcc agaaacgtct gcctcaaatc     960

caaaggagag tgactgacaa ggaaatcaaa aatatgggaa acactctgaa atcacacttt    1020

tag                                                                  1023
```

```
<210> SEQ ID NO 34
<211> LENGTH: 340
<212> TYPE: PRT
<213> ORGANISM: Macaca fascicularis

<400> SEQUENCE: 34

Met Asn Pro Phe His Ser Ser Cys Trp Asn Thr Ser Ala Glu Leu Ser
1               5                   10                  15

Asn Lys Ser Trp Asn Lys Glu Phe Ala Tyr Gln Thr Ala Ser Val Val
            20                  25                  30

Asp Thr Val Ile Leu Pro Ser Met Ile Gly Ile Ile Cys Ser Thr Gly
        35                  40                  45

Leu Val Gly Asn Ile Leu Ile Val Phe Thr Ile Ile Arg Ser Arg Lys
    50                  55                  60

Lys Thr Val Pro Asp Ile Tyr Ile Cys Asn Leu Ala Val Ala Asp Leu
65                  70                  75                  80

Val His Ile Val Gly Met Pro Phe Leu Ile His Gln Trp Ala Arg Gly
                85                  90                  95

Gly Glu Trp Val Phe Gly Gly Pro Leu Cys Thr Ile Ile Thr Ser Leu
            100                 105                 110

Asp Thr Cys Asn Gln Phe Ala Cys Ser Ala Ile Met Thr Val Met Ser
        115                 120                 125

Val Asp Arg Tyr Phe Ala Leu Val Gln Pro Phe Arg Leu Thr Ser Trp
    130                 135                 140

Arg Thr Arg Tyr Lys Thr Ile Arg Ile Asn Leu Gly Leu Trp Ala Ala
145                 150                 155                 160

Ser Phe Ile Leu Ala Leu Pro Val Trp Ile Tyr Ser Lys Val Ile Lys
                165                 170                 175

Phe Lys Asp Gly Val Glu Ser Cys Ala Phe Asp Leu Thr Ser Pro Asp
            180                 185                 190

Asp Val Leu Trp Tyr Thr Leu Tyr Leu Thr Ile Thr Thr Phe Phe Phe
        195                 200                 205

Pro Leu Pro Leu Ile Leu Val Cys Tyr Ile Leu Ile Leu Cys Tyr Thr
    210                 215                 220

Trp Glu Met Tyr Gln Gln Asn Lys Asp Ala Arg Cys Cys Asn Pro Ser
225                 230                 235                 240

Val Pro Lys Gln Arg Val Met Lys Leu Thr Lys Met Val Leu Val Leu
```

-continued

```
                245                 250                 255

Val Ala Val Phe Ile Leu Ser Ala Ala Pro Tyr His Val Ile Gln Leu
            260                 265                 270

Val Asn Leu Gln Met Glu Gln Pro Thr Leu Ala Phe Tyr Val Gly Tyr
        275                 280                 285

Tyr Leu Ser Ile Cys Leu Ser Tyr Ala Ser Ser Ser Ile Asn Pro Phe
    290                 295                 300

Leu Tyr Ile Leu Leu Ser Gly Asn Phe Gln Lys Arg Leu Pro Gln Ile
305                 310                 315                 320

Gln Arg Arg Val Thr Asp Lys Glu Ile Lys Asn Met Gly Asn Thr Leu
                325                 330                 335

Lys Ser His Phe
            340


<210> SEQ ID NO 35
<211> LENGTH: 1023
<212> TYPE: DNA
<213> ORGANISM: Macaca fascicularis

<400> SEQUENCE: 35

atgaatccat ttcactcatc ttgttggaac acctctgccg aactttcaaa caaatcctgg      60

aataaagagt ttgcttatca aactgccagt gttgtagata cagtcatcct cctttccatg     120

attgggatta tctgttcaac agggctggtt ggcaacatcc tcattgtatt cactataata     180

aggtccagaa aaaaaacagt ccctgacatc tatatctgca acctggctgt ggctgatttg     240

gtccacatcg ttggaatgcc ttttcttatt caccagtggg cccgaggggg agagtgggta     300

tttgggggc ctctctgcac catcatcaca tccctggata cttgtaacca atttgcctgt      360

agtgccatca tgactgtaat gagtgtggac aggtactttg ccctcgtcca accatttcga     420

ctgacgagtt ggaggacaag gtacaagacc atccggatca atttgggcct ttgggcagct     480

tcctttatcc tggcattgcc tgtctggatc tactcgaagg tcatcaaatt taaagacggt     540

gtcgagagtt gtgcttttga tttgacatcc cctgacgatg tactctggta tacactttat     600

ttgacaataa caactttctt tttccctcta cccttgattt tggtgtgcta tattttaatt     660

ttatgctata cttgggagat gtatcaacag aataaggatg ccagatgttg caatcccagc     720

gtaccaaaac agagagtgat gaagttgaca aagatggtgc tggtgctggt ggcagtcttt     780

atcctaagtg ctgcccctta tcatgtgata caactggtga acttacagat ggaacagccc     840

acactggcct tctatgtggg ttattacctc tccatctgtc tcagctatgc cagcagcagc     900

attaaccctt ttctctacat cctgctgagt ggaaatttcc agaaacgtct gcctcaaatc     960

caaaggagag tgactgacaa ggaaatcaaa aatatgggaa acactctgaa atcacacttt    1020

tag                                                                  1023


<210> SEQ ID NO 36
<211> LENGTH: 340
<212> TYPE: PRT
<213> ORGANISM: Macaca fascicularis

<400> SEQUENCE: 36

Met Asn Pro Phe His Ser Ser Cys Trp Asn Thr Ser Ala Glu Leu Ser
1               5                   10                  15

Asn Lys Ser Trp Asn Lys Glu Phe Ala Tyr Gln Thr Ala Ser Val Val
            20                  25                  30

Asp Thr Val Ile Leu Leu Ser Met Ile Gly Ile Ile Cys Ser Thr Gly
```

-continued

```
        35                  40                  45

Leu Val Gly Asn Ile Leu Ile Val Phe Thr Ile Ile Arg Ser Arg Lys
    50                  55                  60

Lys Thr Val Pro Asp Ile Tyr Ile Cys Asn Leu Ala Val Ala Asp Leu
65                  70                  75                  80

Val His Ile Val Gly Met Pro Phe Leu Ile His Gln Trp Ala Arg Gly
                85                  90                  95

Gly Glu Trp Val Phe Gly Gly Pro Leu Cys Thr Ile Ile Thr Ser Leu
            100                 105                 110

Asp Thr Cys Asn Gln Phe Ala Cys Ser Ala Ile Met Thr Val Met Ser
        115                 120                 125

Val Asp Arg Tyr Phe Ala Leu Val Gln Pro Phe Arg Leu Thr Ser Trp
    130                 135                 140

Arg Thr Arg Tyr Lys Thr Ile Arg Ile Asn Leu Gly Leu Trp Ala Ala
145                 150                 155                 160

Ser Phe Ile Leu Ala Leu Pro Val Trp Ile Tyr Ser Lys Val Ile Lys
                165                 170                 175

Phe Lys Asp Gly Val Glu Ser Cys Ala Phe Asp Leu Thr Ser Pro Asp
            180                 185                 190

Asp Val Leu Trp Tyr Thr Leu Tyr Leu Thr Ile Thr Thr Phe Phe Phe
        195                 200                 205

Pro Leu Pro Leu Ile Leu Val Cys Tyr Ile Leu Ile Leu Cys Tyr Thr
    210                 215                 220

Trp Glu Met Tyr Gln Gln Asn Lys Asp Ala Arg Cys Cys Asn Pro Ser
225                 230                 235                 240

Val Pro Lys Gln Arg Val Met Lys Leu Thr Lys Met Val Leu Val Leu
                245                 250                 255

Val Ala Val Phe Ile Leu Ser Ala Ala Pro Tyr His Val Ile Gln Leu
            260                 265                 270

Val Asn Leu Gln Met Glu Gln Pro Thr Leu Ala Phe Tyr Val Gly Tyr
        275                 280                 285

Tyr Leu Ser Ile Cys Leu Ser Tyr Ala Ser Ser Ser Ile Asn Pro Phe
    290                 295                 300

Leu Tyr Ile Leu Leu Ser Gly Asn Phe Gln Lys Arg Leu Pro Gln Ile
305                 310                 315                 320

Gln Arg Arg Val Thr Asp Lys Glu Ile Lys Asn Met Gly Asn Thr Leu
                325                 330                 335

Lys Ser His Phe
            340
```

<210> SEQ ID NO 37
<211> LENGTH: 1023
<212> TYPE: DNA
<213> ORGANISM: Macaca fascicularis

<400> SEQUENCE: 37

```
atgaatccat ttcactcatc ttgttggaac acctctgccg aactttcaaa caaatcctgg      60

aataaagagt ttgcttatca aactgccagt gttgtagata cagtcatcct cccttccatg     120

attgggatta tctgttcaac agggctggtt ggcaacatcc tcattgtatt cactataata     180

aggtccagaa aaaaaacagt ccctgacatc tatatctgca acctggctgt ggctgatttg     240

gtccacatcg ttggaatgcc ttttcttatt caccagtggg cccgaggggg agagtgggta     300

tttgggggc ctctctgcac catcatcaca tccctggata cttgtaacca atttgcctgt     360
```

-continued

```
agtgccatca tgactgtaat gagtgtggac aggtactttg ccctcgtcca accatttcga    420

ctgacaagtt ggagaacaag gtacaagacc atccggatca atttgggcct ttgggcagct    480

tcctttatcc tggcattgcc tgtctggatc tactcgaagg tcatcaaatt taaagacggt    540

gtcgagagtt gtgcttttga tttgacatcc cctgacgatg tactctggta tacactttat    600

ttgacaataa caactttctt tttccctcta cccttgattt tggtgtgcta tattttaatt    660

ttatgctata cttgggagat gtatcaacag aataaggatg ccagatgttg caatcccagc    720

gtaccaaaac agagagtgat gaagttgaca aagatggtgc tggtgctggt ggcagtcttt    780

atcctaagtg ctgcccctta tcatgtgata caactggtga acttacagat ggaacagccc    840

acactggcct tctatgtggg ttattacctc tccatctgtc tcagctatgc cagcagcagc    900

attaaccctt ttctctacat cctgctgagt ggaaatttcc agaaacgtct gcctcaaatc    960

caaaggagag tgactgacaa ggaaatcaaa aatatgggaa acactctgaa atcacacttt   1020

tag                                                                 1023
```

<210> SEQ ID NO 38
<211> LENGTH: 993
<212> TYPE: DNA
<213> ORGANISM: Canis sp.

<400> SEQUENCE: 38

```
atgtattcac ttcactcatc ctgttggaac acctctgctg aacctttgaa caaatcctgc     60

aataaagagt ttgcttatca caccctcagc attttagata caatcatcct cccttctatg    120

attgggatta tctgttcaat ggggctagtt ggcaacatcc tcattgtatt cactataata    180

aggtccagga aaaaaaccat tcctgacatt tatatctgca acctggctgt ggctgatctg    240

gtccacatca ttggaatgcc atttcttatt catcagtggg cccggggagg agagtgggtg    300

tttggggggc ccctctgcac cattatcaca tccctggata cctgcaacca gtttgcctgt    360

agtgccatca tgactgtgat gagtatagac aggtacttgg ctctcgtcca accatttcga    420

cttacaagtt ggagaacgag gtacaagacc atccgcatca atttgggcct ttgggcagct    480

tccttcattc tggcgctgcc tgtctgggtc tactcgaagg tcatcaaatt taaagacggc    540

gtggagagtt gtgcttttga tttaacatcc cctgacgatg tactccggta tacactttat    600

ttgacgataa caactttttt tttccctttg cctttgattt tggtgtgcta tattttaatt    660

ttatgctata cttgggagat gtatcaacag aataaagatg caagatgtta caatcccagt    720

gttccaaaag agagagtgat gaagctgaca aagatggtgc tggtgctggt ggcggtcttt    780

atcctaagtg ctgcccccta ccacgtgata caactggtga acttaaagat gcagcagccc    840

acactggcct tccatgtagg ctattatctc tccatctgtt tcagctatgc cagcagcagc    900

attaaccctt tcctctacat catgctgagt ggaaatttcc ggaaacgcct acctcaagta    960

caaaggagag tgactgagaa atcaacaata tag                                 993
```

<210> SEQ ID NO 39
<211> LENGTH: 330
<212> TYPE: PRT
<213> ORGANISM: Canis sp.

<400> SEQUENCE: 39

```
Met Tyr Ser Leu His Ser Ser Cys Trp Asn Thr Ser Ala Glu Pro Leu
1               5                   10                  15

Asn Lys Ser Cys Asn Lys Glu Phe Ala Tyr His Thr Leu Ser Ile Leu
            20                  25                  30
```

```
Asp Thr Ile Ile Leu Pro Ser Met Ile Gly Ile Ile Cys Ser Met Gly
        35                  40                  45

Leu Val Gly Asn Ile Leu Ile Val Phe Thr Ile Ile Arg Ser Arg Lys
    50                  55                  60

Lys Thr Ile Pro Asp Ile Tyr Ile Cys Asn Leu Ala Val Ala Asp Leu
65                  70                  75                  80

Val His Ile Ile Gly Met Pro Phe Leu Ile His Gln Trp Ala Arg Gly
                85                  90                  95

Gly Glu Trp Val Phe Gly Gly Pro Leu Cys Thr Ile Ile Thr Ser Leu
            100                 105                 110

Asp Thr Cys Asn Gln Phe Ala Cys Ser Ala Ile Met Thr Val Met Ser
        115                 120                 125

Ile Asp Arg Tyr Leu Ala Leu Val Gln Pro Phe Arg Leu Thr Ser Trp
    130                 135                 140

Arg Thr Arg Tyr Lys Thr Ile Arg Ile Asn Leu Gly Leu Trp Ala Ala
145                 150                 155                 160

Ser Phe Ile Leu Ala Leu Pro Val Trp Val Tyr Ser Lys Val Ile Lys
                165                 170                 175

Phe Lys Asp Gly Val Glu Ser Cys Ala Phe Asp Leu Thr Ser Pro Asp
            180                 185                 190

Asp Val Leu Arg Tyr Thr Leu Tyr Leu Thr Ile Thr Thr Phe Phe Phe
        195                 200                 205

Pro Leu Pro Leu Ile Leu Val Cys Tyr Ile Leu Ile Leu Cys Tyr Thr
    210                 215                 220

Trp Glu Met Tyr Gln Gln Asn Lys Asp Ala Arg Cys Tyr Asn Pro Ser
225                 230                 235                 240

Val Pro Lys Glu Arg Val Met Lys Leu Thr Lys Met Val Leu Val Leu
                245                 250                 255

Val Ala Val Phe Ile Leu Ser Ala Ala Pro Tyr His Val Ile Gln Leu
            260                 265                 270

Val Asn Leu Lys Met Gln Gln Pro Thr Leu Ala Phe His Val Gly Tyr
        275                 280                 285

Tyr Leu Ser Ile Cys Phe Ser Tyr Ala Ser Ser Ser Ile Asn Pro Phe
    290                 295                 300

Leu Tyr Ile Met Leu Ser Gly Asn Phe Arg Lys Arg Leu Pro Gln Val
305                 310                 315                 320

Gln Arg Arg Val Thr Glu Lys Ser Thr Ile
                325                 330
```

<210> SEQ ID NO 40
<211> LENGTH: 1062
<212> TYPE: DNA
<213> ORGANISM: artificial sequence
<220> FEATURE:
<223> OTHER INFORMATION: Cynomolgus macaque MCH1R DNA sequence with BspE site added for C-terminal chimeras

<400> SEQUENCE: 40

```
atggacctgg aagcctcgct gctgcccact ggtcccaaca ccagcaacac ctctgatggc     60

cccgataacc tcacctcggc aggatcacct cctcgctcag ggagcgtctc ctacatcaac    120

atcatcatgc cttcggtgtt cggcaccatc tgcctcctgg gcatcatcgg gaactccatg    180

gtcatcttcg cggtcgtgaa gaagtccaag ctgcactggt gcaacaatgt ccccgacatc    240

ttcatcatca acctctcggt ggtggatctc ctctttctcc tgggcatgcc cttcatgatc    300
```

-continued

```
caccagctca tgggcaatgg ggtgtggcac tttggggaga ccatgtgcac cctcatcacg    360
gccatggatg ccaatagtca gttcaccagc acctacatcc tgaccgccat ggccattgac    420
cgctacctgg ccaccgtcca ccccatctct tccacaaagt tccggaagcc ctctgtggcc    480
accctggtga tctgcctcct gtgggccctc tccttcatca gcatcacccc cgtgtggttg    540
tatgccagac tcatcccctt cccaggaggt gcagtgggct gcggcatccg cttgcccaac    600
ccggacactg acctttactg gttcaccctg taccagtttt tcctggcctt tgccctgccc    660
ttcgtggtca tcacggccgc atacgtgagg atcctgcagc gcatgacgtc ctcagtggcc    720
cccgcctccc agcgcagcat ccggctgcgg acaaagaggg tgacccgcac agccatcgcc    780
atctgcctgg tcttctttgt gtgctgggca ccctactatg tgctacagct gacccagttg    840
tccatcagcc gcccgaccct caccttttgtc tacctgtaca atgcggccat cagcttgggc    900
tacgccaaca gctgcctcaa cccctttgtg tacattgtgc tctgcgagac gttccggaaa    960
cgcttggtcc tttcggtgaa gcctgcagcc caggggcagc ttcgcgctgt cagcaacgct   1020
cagacggctg acgaggagag gacagaaagc aaaggtacct ga                      1062
```

<210> SEQ ID NO 41
<211> LENGTH: 1074
<212> TYPE: DNA
<213> ORGANISM: artificial sequence
<220> FEATURE:
<223> OTHER INFORMATION: Cynomolgus macaque MCH1R/human NPY1 IC3 chimera

<400> SEQUENCE: 41

```
atggacctgg aagcctcgct gctgcccact ggtcccaaca ccagcaacac ctctgatggc     60
cccgataacc tcacctcggc aggatcacct cctcgctcag ggagcgtctc ctacatcaac    120
atcatcatgc cttcggtgtt cggcaccatc tgcctcctgg gcatcatcgg gaactccatg    180
gtcatcttcg cggtcgtgaa gaagtccaag ctgcactggt gcaacaatgt ccccgacatc    240
ttcatcatca acctctcggt ggtggatctc ctctttctcc tgggcatgcc cttcatgatc    300
caccagctca tgggcaatgg ggtgtggcac tttggggaga ccatgtgcac cctcatcacg    360
gccatggatg ccaatagtca gttcaccagc acctacatcc tgaccgccat ggccattgac    420
cgctacctgg ccaccgtcca ccccatctct tccacaaagt tccggaagcc ctctgtggcc    480
accctggtga tctgcctcct gtgggccctc tccttcatca gcatcacccc cgtgtggttg    540
tatgccagac tcatcccctt cccaggaggt gcagtgggct gcggcatccg cttgcccaac    600
ccggacactg acctttactg gttcaccctg taccagtttt tcctggcctt tgccctgccc    660
ttcgtggtca tcacggccgc atacgtgagg atcctgatac gcctaaaaag gagaaacaac    720
atgatggaca agatgagaga caataagtac aggtccagtg aaaccaaaag ggtgacccgc    780
acagccatcg ccatctgcct ggtcttcttt gtgtgctggg caccctacta tgtgctacag    840
ctgacccagt tgtccatcag ccgcccgacc ctcacctttg tctacctgta caatgcggcc    900
atcagcttgg gctacgccaa cagctgcctc aacccctttg tgtacattgt gctctgcgag    960
acgttccgca aacgcttggt cctttcggtg aagcctgcag cccaggggca gcttcgcgct   1020
gtcagcaacg ctcagacggc tgacgaggag aggacagaaa gcaaaggtac ctga         1074
```

<210> SEQ ID NO 42
<211> LENGTH: 357
<212> TYPE: PRT
<213> ORGANISM: artificial sequence
<220> FEATURE:
<223> OTHER INFORMATION: Cynomolgus macaque MCH1R/human NPY1 IC3

-continued

```
      chimera - amino acid sequence

<400> SEQUENCE: 42

Met Asp Leu Glu Ala Ser Leu Leu Pro Thr Gly Pro Asn Thr Ser Asn
1               5                   10                  15

Thr Ser Asp Gly Pro Asp Asn Leu Thr Ser Ala Gly Ser Pro Pro Arg
            20                  25                  30

Ser Gly Ser Val Ser Tyr Ile Asn Ile Ile Met Pro Ser Val Phe Gly
        35                  40                  45

Thr Ile Cys Leu Leu Gly Ile Ile Gly Asn Ser Met Val Ile Phe Ala
    50                  55                  60

Val Val Lys Lys Ser Lys Leu His Trp Cys Asn Asn Val Pro Asp Ile
65                  70                  75                  80

Phe Ile Ile Asn Leu Ser Val Val Asp Leu Leu Phe Leu Leu Gly Met
                85                  90                  95

Pro Phe Met Ile His Gln Leu Met Gly Asn Gly Val Trp His Phe Gly
            100                 105                 110

Glu Thr Met Cys Thr Leu Ile Thr Ala Met Asp Ala Asn Ser Gln Phe
        115                 120                 125

Thr Ser Thr Tyr Ile Leu Thr Ala Met Ala Ile Asp Arg Tyr Leu Ala
    130                 135                 140

Thr Val His Pro Ile Ser Ser Thr Lys Phe Arg Lys Pro Ser Val Ala
145                 150                 155                 160

Thr Leu Val Ile Cys Leu Leu Trp Ala Leu Ser Phe Ile Ser Ile Thr
                165                 170                 175

Pro Val Trp Leu Tyr Ala Arg Leu Ile Pro Phe Pro Gly Gly Ala Val
            180                 185                 190

Gly Cys Gly Ile Arg Leu Pro Asn Pro Asp Thr Asp Leu Tyr Trp Phe
        195                 200                 205

Thr Leu Tyr Gln Phe Phe Leu Ala Phe Ala Leu Pro Phe Val Val Ile
    210                 215                 220

Thr Ala Ala Tyr Val Arg Ile Leu Ile Arg Leu Lys Arg Arg Asn Asn
225                 230                 235                 240

Met Met Asp Lys Met Arg Asp Asn Lys Tyr Arg Ser Ser Glu Thr Lys
                245                 250                 255

Arg Val Thr Arg Thr Ala Ile Ala Ile Cys Leu Val Phe Phe Val Cys
            260                 265                 270

Trp Ala Pro Tyr Tyr Val Leu Gln Leu Thr Gln Leu Ser Ile Ser Arg
        275                 280                 285

Pro Thr Leu Thr Phe Val Tyr Leu Tyr Asn Ala Ala Ile Ser Leu Gly
    290                 295                 300

Tyr Ala Asn Ser Cys Leu Asn Pro Phe Val Tyr Ile Val Leu Cys Glu
305                 310                 315                 320

Thr Phe Arg Lys Arg Leu Val Leu Ser Val Lys Pro Ala Ala Gln Gly
                325                 330                 335

Gln Leu Arg Ala Val Ser Asn Ala Gln Thr Ala Asp Glu Glu Arg Thr
            340                 345                 350

Glu Ser Lys Gly Thr
        355


<210> SEQ ID NO 43
<211> LENGTH: 1128
<212> TYPE: DNA
<213> ORGANISM: artificial sequence
<220> FEATURE:
```

-continued

<223> OTHER INFORMATION: Cynomolgus macaque MCH1R/human NPY1 C-terminal chimera

<400> SEQUENCE: 43

```
atggacctgg aagcctcgct gctgcccact ggtcccaaca ccagcaacac ctctgatggc     60
cccgataacc tcacctcggc aggatcacct cctcgctcag ggagcgtctc ctacatcaac    120
atcatcatgc cttcggtgtt cggcaccatc tgcctcctgg gcatcatcgg gaactccatg    180
gtcatcttcg cggtcgtgaa gaagtccaag ctgcactggt gcaacaatgt ccccgacatc    240
ttcatcatca acctctcggt ggtggatctc ctctttctcc tgggcatgcc cttcatgatc    300
caccagctca tgggcaatgg ggtgtggcac tttggggaga ccatgtgcac cctcatcacg    360
gccatggatg ccaatagtca gttcaccagc acctacatcc tgaccgccat ggccattgac    420
cgctacctgg ccaccgtcca ccccatctct tccacaaagt tccggaagcc ctctgtggcc    480
accctggtga tctgcctcct gtgggccctc tccttcatca gcatcacccc cgtgtggttg    540
tatgccagac tcatcccctt cccaggaggt gcagtgggct gcggcatccg cttgcccaac    600
ccggacactg acctttactg gttcaccctg taccagtttt tcctggcctt tgccctgccc    660
ttcgtggtca tcacggccgc atacgtgagg atcctgcagc gcatgacgtc ctcagtggcc    720
cccgcctccc agcgcagcat ccggctgcgg acaaagaggg tgacccgcac agccatcgcc    780
atctgcctgg tcttctttgt gtgctgggca ccctactatg tgctacagct gacccagttg    840
tccatcagcc gcccgaccct cacctttgtc tacctgtaca atgcggccat cagcttgggc    900
tacgccaaca gctgcctcaa cccctttgtg tacattgtgc tctgcgagac gttccggaga    960
gacttgcagt tcttcttcaa cttttgtgat ttccggtctc gggatgatga ttatgaaaca   1020
atagccatgt ccacgatgca cacagatgtt tccaaaactt ctttgaagca agcaagccca   1080
gtcgcattta aaaaaatcaa caacaatgat gataatgaaa aaatctga                1128
```

<210> SEQ ID NO 44
<211> LENGTH: 375
<212> TYPE: PRT
<213> ORGANISM: artificial sequence
<220> FEATURE:
<223> OTHER INFORMATION: Cynomolgus macaque MCH1R/human NPY1 C-terminal chimera - amino acid sequence

<400> SEQUENCE: 44

```
Met Asp Leu Glu Ala Ser Leu Leu Pro Thr Gly Pro Asn Thr Ser Asn
1               5                   10                  15

Thr Ser Asp Gly Pro Asp Asn Leu Thr Ser Ala Gly Ser Pro Pro Arg
            20                  25                  30

Ser Gly Ser Val Ser Tyr Ile Asn Ile Ile Met Pro Ser Val Phe Gly
        35                  40                  45

Thr Ile Cys Leu Leu Gly Ile Ile Gly Asn Ser Met Val Ile Phe Ala
    50                  55                  60

Val Val Lys Lys Ser Lys Leu His Trp Cys Asn Asn Val Pro Asp Ile
65                  70                  75                  80

Phe Ile Ile Asn Leu Ser Val Val Asp Leu Leu Phe Leu Leu Gly Met
                85                  90                  95

Pro Phe Met Ile His Gln Leu Met Gly Asn Gly Val Trp His Phe Gly
            100                 105                 110

Glu Thr Met Cys Thr Leu Ile Thr Ala Met Asp Ala Asn Ser Gln Phe
        115                 120                 125

Thr Ser Thr Tyr Ile Leu Thr Ala Met Ala Ile Asp Arg Tyr Leu Ala
```

-continued

```
    130                 135                 140

Thr Val His Pro Ile Ser Ser Thr Lys Phe Arg Lys Pro Ser Val Ala
145                 150                 155                 160

Thr Leu Val Ile Cys Leu Leu Trp Ala Leu Ser Phe Ile Ser Ile Thr
                165                 170                 175

Pro Val Trp Leu Tyr Ala Arg Leu Ile Pro Phe Pro Gly Gly Ala Val
            180                 185                 190

Gly Cys Gly Ile Arg Leu Pro Asn Pro Asp Thr Asp Leu Tyr Trp Phe
        195                 200                 205

Thr Leu Tyr Gln Phe Phe Leu Ala Phe Ala Leu Pro Phe Val Val Ile
    210                 215                 220

Thr Ala Ala Tyr Val Arg Ile Leu Gln Arg Met Thr Ser Ser Val Ala
225                 230                 235                 240

Pro Ala Ser Gln Arg Ser Ile Arg Leu Arg Thr Lys Arg Val Thr Arg
                245                 250                 255

Thr Ala Ile Ala Ile Cys Leu Val Phe Phe Val Cys Trp Ala Pro Tyr
            260                 265                 270

Tyr Val Leu Gln Leu Thr Gln Leu Ser Ile Ser Arg Pro Thr Leu Thr
        275                 280                 285

Phe Val Tyr Leu Tyr Asn Ala Ala Ile Ser Leu Gly Tyr Ala Asn Ser
    290                 295                 300

Cys Leu Asn Pro Phe Val Tyr Ile Val Leu Cys Glu Thr Phe Arg Arg
305                 310                 315                 320

Asp Leu Gln Phe Phe Phe Asn Phe Cys Asp Phe Arg Ser Arg Asp Asp
                325                 330                 335

Asp Tyr Glu Thr Ile Ala Met Ser Thr Met His Thr Asp Val Ser Lys
            340                 345                 350

Thr Ser Leu Lys Gln Ala Ser Pro Val Ala Phe Lys Lys Ile Asn Asn
        355                 360                 365

Asn Asp Asp Asn Glu Lys Ile
    370                 375
```

<210> SEQ ID NO 45
<211> LENGTH: 1167
<212> TYPE: DNA
<213> ORGANISM: artificial sequence
<220> FEATURE:
<223> OTHER INFORMATION: Cynomolgus macaque MCH1R/human beta-2 adrenergic receptor C-terminal chimera

<400> SEQUENCE: 45

```
atggacctgg aagcctcgct gctgcccact ggtcccaaca ccagcaacac ctctgatggc     60

cccgataacc tcacctcggc aggatcacct cctcgctcag ggagcgtctc ctacatcaac    120

atcatcatgc cttcggtgtt cggcaccatc tgcctcctgg gcatcatcgg gaactccatg    180

gtcatcttcg cggtcgtgaa gaagtccaag ctgcactggt gcaacaatgt ccccgacatc    240

ttcatcatca acctctcggt ggtggatctc ctctttctcc tgggcatgcc cttcatgatc    300

caccagctca tgggcaatgg ggtgtggcac tttggggaga ccatgtgcac cctcatcacg    360

gccatggatg ccaatagtca gttcaccagc acctacatcc tgaccgccat ggccattgac    420

cgctacctgg ccaccgtcca ccccatctct tccacaaagt tccggaagcc ctctgtggcc    480

accctggtga tctgcctcct gtgggccctc tccttcatca gcatcacccc cgtgtggttg    540

tatgccagac tcatcccctt cccaggaggt gcagtgggct gcggcatccg cttgcccaac    600

ccggacactg acctttactg gttcaccctg taccagtttt tcctggcctt tgccctgccc    660
```

```
ttcgtggtca tcacggccgc atacgtgagg atcctgcagc gcatgacgtc ctcagtggcc    720

cccgcctccc agcgcagcat ccggctgcgg acaaagaggg tgacccgcac agccatcgcc    780

atctgcctgg tcttctttgt gtgctgggca ccctactatg tgctacagct gacccagttg    840

tccatcagcc gcccgacct caccttttgtc tacctgtaca atgcggccat cagcttgggc    900

tacgccaaca gctgcctcaa cccctttgtg tacattgtgc tctgcgagac gttccggagt    960

tctttgaagg cctatgggaa tggctactcc agcaacggca acacagggga gcagagtgga   1020

tatcacgtgg aacaggagaa agaaaataaa ctgctgtgtg aagacctccc aggcacggaa   1080

gactttgtgg gccatcaagg tactgtgcct agcgataaca ttgattcaca agggaggaat   1140

tgtagtacaa atgactcact gctgtaa                                       1167
```

```
<210> SEQ ID NO 46
<211> LENGTH: 388
<212> TYPE: PRT
<213> ORGANISM: artificial sequence
<220> FEATURE:
<223> OTHER INFORMATION: Cynomolgus macaque MCH1R/human beta-2
      adrenergic receptor C-terminal chimera - amino acid sequence

<400> SEQUENCE: 46

Met Asp Leu Glu Ala Ser Leu Leu Pro Thr Gly Pro Asn Thr Ser Asn
1               5                   10                  15

Thr Ser Asp Gly Pro Asp Asn Leu Thr Ser Ala Gly Ser Pro Pro Arg
            20                  25                  30

Ser Gly Ser Val Ser Tyr Ile Asn Ile Ile Met Pro Ser Val Phe Gly
        35                  40                  45

Thr Ile Cys Leu Leu Gly Ile Ile Gly Asn Ser Met Val Ile Phe Ala
    50                  55                  60

Val Val Lys Lys Ser Lys Leu His Trp Cys Asn Asn Val Pro Asp Ile
65                  70                  75                  80

Phe Ile Ile Asn Leu Ser Val Val Asp Leu Leu Phe Leu Leu Gly Met
                85                  90                  95

Pro Phe Met Ile His Gln Leu Met Gly Asn Gly Val Trp His Phe Gly
            100                 105                 110

Glu Thr Met Cys Thr Leu Ile Thr Ala Met Asp Ala Asn Ser Gln Phe
        115                 120                 125

Thr Ser Thr Tyr Ile Leu Thr Ala Met Ala Ile Asp Arg Tyr Leu Ala
    130                 135                 140

Thr Val His Pro Ile Ser Ser Thr Lys Phe Arg Lys Pro Ser Val Ala
145                 150                 155                 160

Thr Leu Val Ile Cys Leu Leu Trp Ala Leu Ser Phe Ile Ser Ile Thr
                165                 170                 175

Pro Val Trp Leu Tyr Ala Arg Leu Ile Pro Phe Pro Gly Gly Ala Val
            180                 185                 190

Gly Cys Gly Ile Arg Leu Pro Asn Pro Asp Thr Asp Leu Tyr Trp Phe
        195                 200                 205

Thr Leu Tyr Gln Phe Phe Leu Ala Phe Ala Leu Pro Phe Val Val Ile
    210                 215                 220

Thr Ala Ala Tyr Val Arg Ile Leu Gln Arg Met Thr Ser Ser Val Ala
225                 230                 235                 240

Pro Ala Ser Gln Arg Ser Ile Arg Leu Arg Thr Lys Arg Val Thr Arg
                245                 250                 255

Thr Ala Ile Ala Ile Cys Leu Val Phe Phe Val Cys Trp Ala Pro Tyr
```

-continued

```
        260                 265                 270

Tyr Val Leu Gln Leu Thr Gln Leu Ser Ile Ser Arg Pro Thr Leu Thr
        275                 280                 285

Phe Val Tyr Leu Tyr Asn Ala Ala Ile Ser Leu Gly Tyr Ala Asn Ser
    290                 295                 300

Cys Leu Asn Pro Phe Val Tyr Ile Val Leu Cys Glu Thr Phe Arg Ser
305                 310                 315                 320

Ser Leu Lys Ala Tyr Gly Asn Gly Tyr Ser Ser Asn Gly Asn Thr Gly
                325                 330                 335

Glu Gln Ser Gly Tyr His Val Glu Gln Glu Lys Glu Asn Lys Leu Leu
            340                 345                 350

Cys Glu Asp Leu Pro Gly Thr Glu Asp Phe Val Gly His Gln Gly Thr
        355                 360                 365

Val Pro Ser Asp Asn Ile Asp Ser Gln Gly Arg Asn Cys Ser Thr Asn
    370                 375                 380

Asp Ser Leu Leu
385
```

<210> SEQ ID NO 47
<211> LENGTH: 1059
<212> TYPE: DNA
<213> ORGANISM: artificial sequence
<220> FEATURE:
<223> OTHER INFORMATION: Cynomolgus macaque MCH1R/MCH2R N-terminal chimera

<400> SEQUENCE: 47

```
atgaatccat ttcactcatc ttgttggaac acctctgccg aactttcaaa caaatcctgg     60

aataaagagt ttgcttatca aactgccagt gttgtagata ccgtctccta catcaacatc    120

atcatgcctt cggtgttcgg caccatctgc ctcctgggca tcatcgggaa ctccatggtc    180

atcttcgcgg tcgtgaagaa gtccaagctg cactggtgca acaatgtccc cgacatcttc    240

atcatcaacc tctcggtggt ggatctcctc tttctcctgg gcatgccctt catgatccac    300

cagctcatgg gcaatggggt gtggcacttt ggggagacca tgtgcaccct catcacggcc    360

atggatgcca atagtcagtt caccagcacc tacatcctga ccgccatggc cattgaccgc    420

tacctggcca ccgtccaccc catctcttcc acaaagttcc ggaagccctc tgtggccacc    480

ctggtgatct gcctcctgtg ggccctctcc ttcatcagca tcacccccgt gtggttgtat    540

gccagactca tccccttccc aggaggtgca gtgggctgcg gcatccgctt gcccaacccg    600

gacactgacc tttactggtt caccctgtac cagtttttcc tggcctttgc cctgcccttc    660

gtggtcatca cggccgcata cgtgaggatc ctgcagcgca tgacgtcctc agtggccccc    720

gcctcccagc gcagcatccg gctgcggaca aagagggtga cccgcacagc catcgccatc    780

tgcctggtct tctttgtgtg ctgggcaccc tactatgtgc tacagctgac ccagttgtcc    840

atcagccgcc cgaccctcac ctttgtctac ctgtacaatg cggccatcag cttgggctac    900

gccaacagct gcctcaaccc ctttgtgtac attgtgctct gcgagacgtt ccgcaaacgc    960

ttggtccttt cggtgaagcc tgcagcccag ggcagcttc gcgctgtcag caacgctcag    1020

acggctgacg aggagaggac agaaagcaaa ggtacctga                           1059
```

<210> SEQ ID NO 48
<211> LENGTH: 352
<212> TYPE: PRT
<213> ORGANISM: artificial sequence
<220> FEATURE:

<223> OTHER INFORMATION: Cynomolgus macaque MCH1R/MCH2R N-terminal chimera - amino acid se quence

<400> SEQUENCE: 48

```
Met Asn Pro Phe His Ser Ser Cys Trp Asn Thr Ser Ala Glu Leu Ser
1               5                   10                  15

Asn Lys Ser Trp Asn Lys Glu Phe Ala Tyr Gln Thr Ala Ser Val Val
            20                  25                  30

Asp Thr Val Ser Tyr Ile Asn Ile Ile Met Pro Ser Val Phe Gly Thr
        35                  40                  45

Ile Cys Leu Leu Gly Ile Ile Gly Asn Ser Met Val Ile Phe Ala Val
    50                  55                  60

Val Lys Lys Ser Lys Leu His Trp Cys Asn Asn Val Pro Asp Ile Phe
65                  70                  75                  80

Ile Ile Asn Leu Ser Val Val Asp Leu Leu Phe Leu Leu Gly Met Pro
                85                  90                  95

Phe Met Ile His Gln Leu Met Gly Asn Gly Val Trp His Phe Gly Glu
            100                 105                 110

Thr Met Cys Thr Leu Ile Thr Ala Met Asp Ala Asn Ser Gln Phe Thr
        115                 120                 125

Ser Thr Tyr Ile Leu Thr Ala Met Ala Ile Asp Arg Tyr Leu Ala Thr
    130                 135                 140

Val His Pro Ile Ser Ser Thr Lys Phe Arg Lys Pro Ser Val Ala Thr
145                 150                 155                 160

Leu Val Ile Cys Leu Leu Trp Ala Leu Ser Phe Ile Ser Ile Thr Pro
                165                 170                 175

Val Trp Leu Tyr Ala Arg Leu Ile Pro Phe Pro Gly Gly Ala Val Gly
            180                 185                 190

Cys Gly Ile Arg Leu Pro Asn Pro Asp Thr Asp Leu Tyr Trp Phe Thr
        195                 200                 205

Leu Tyr Gln Phe Phe Leu Ala Phe Ala Leu Pro Phe Val Val Ile Thr
    210                 215                 220

Ala Ala Tyr Val Arg Ile Leu Gln Arg Met Thr Ser Ser Val Ala Pro
225                 230                 235                 240

Ala Ser Gln Arg Ser Ile Arg Leu Arg Thr Lys Arg Val Thr Arg Thr
                245                 250                 255

Ala Ile Ala Ile Cys Leu Val Phe Phe Val Cys Trp Ala Pro Tyr Tyr
            260                 265                 270

Val Leu Gln Leu Thr Gln Leu Ser Ile Ser Arg Pro Thr Leu Thr Phe
        275                 280                 285

Val Tyr Leu Tyr Asn Ala Ala Ile Ser Leu Gly Tyr Ala Asn Ser Cys
    290                 295                 300

Leu Asn Pro Phe Val Tyr Ile Val Leu Cys Glu Thr Phe Arg Lys Arg
305                 310                 315                 320

Leu Val Leu Ser Val Lys Pro Ala Ala Gln Gly Gln Leu Arg Ala Val
                325                 330                 335

Ser Asn Ala Gln Thr Ala Asp Glu Glu Arg Thr Glu Ser Lys Gly Thr
            340                 345                 350
```

<210> SEQ ID NO 49
<211> LENGTH: 1080
<212> TYPE: DNA
<213> ORGANISM: artificial sequence
<220> FEATURE:
<223> OTHER INFORMATION: Cynomolgus macaque MCH1R/MCH2R IC3 chimera

<400> SEQUENCE: 49

```
atggacctgg aagcctcgct gctgcccact ggtcccaaca ccagcaacac ctctgatggc     60
cccgataacc tcacctcggc aggatcacct cctcgctcag ggagcgtctc ctacatcaac    120
atcatcatgc cttcggtgtt cggcaccatc tgcctcctgg gcatcatcgg gaactccatg    180
gtcatcttcg cggtcgtgaa gaagtccaag ctgcactggt gcaacaatgt ccccgacatc    240
ttcatcatca acctctcggt ggtggatctc ctctttctcc tgggcatgcc cttcatgatc    300
caccagctca tgggcaatgg ggtgtggcac tttggggaga ccatgtgcac cctcatcacg    360
gccatggatg ccaatagtca gttcaccagc acctacatcc tgaccgccat ggccattgac    420
cgctacctgg ccaccgtcca ccccatctct tccacaaagt tccggaagcc ctctgtggcc    480
accctggtga tctgcctcct gtgggccctc tccttcatca gcatcacccc cgtgtggttg    540
tatgccagac tcatcccctt cccaggaggt gcagtgggct gcggcatccg cttgcccaac    600
ccggacactg acctttactg gttcaccctg taccagtttt tcctggcctt tgccctgccc    660
ttcgtggtca tcacggccgc atacgtgagg atcctgtgct atacttggga gatgtatcaa    720
cagaataagg atgccagatg ttgcaatccc agcgtaccaa aacagagagt gatgaaggtg    780
acccgcacag ccatcgccat ctgcctggtc ttctttgtgt gctgggcacc ctactatgtg    840
ctacagctga cccagttgtc catcagccgc ccgaccctca cctttgtcta cctgtacaat    900
gcggccatca gcttgggcta cgccaacagc tgcctcaacc cctttgtgta cattgtgctc    960
tgcgagacgt tccgcaaacg cttggtcctt tcggtgaagc ctgcagccca ggggcagctt   1020
cgcgctgtca gcaacgctca gacggctgac gaggagagga cagaaagcaa aggtacctga   1080
```

<210> SEQ ID NO 50
<211> LENGTH: 359
<212> TYPE: PRT
<213> ORGANISM: artificial sequence
<220> FEATURE:
<223> OTHER INFORMATION: Cynomolgus macaque MCH1R/MCH2R IC3 chimera - amino acid sequence

<400> SEQUENCE: 50

```
Met Asp Leu Glu Ala Ser Leu Leu Pro Thr Gly Pro Asn Thr Ser Asn
1               5                   10                  15

Thr Ser Asp Gly Pro Asp Asn Leu Thr Ser Ala Gly Ser Pro Pro Arg
            20                  25                  30

Ser Gly Ser Val Ser Tyr Ile Asn Ile Ile Met Pro Ser Val Phe Gly
        35                  40                  45

Thr Ile Cys Leu Leu Gly Ile Ile Gly Asn Ser Met Val Ile Phe Ala
    50                  55                  60

Val Val Lys Lys Ser Lys Leu His Trp Cys Asn Asn Val Pro Asp Ile
65                  70                  75                  80

Phe Ile Ile Asn Leu Ser Val Val Asp Leu Leu Phe Leu Leu Gly Met
                85                  90                  95

Pro Phe Met Ile His Gln Leu Met Gly Asn Gly Val Trp His Phe Gly
            100                 105                 110

Glu Thr Met Cys Thr Leu Ile Thr Ala Met Asp Ala Asn Ser Gln Phe
        115                 120                 125

Thr Ser Thr Tyr Ile Leu Thr Ala Met Ala Ile Asp Arg Tyr Leu Ala
    130                 135                 140

Thr Val His Pro Ile Ser Ser Thr Lys Phe Arg Lys Pro Ser Val Ala
145                 150                 155                 160
```

-continued

```
Thr Leu Val Ile Cys Leu Leu Trp Ala Leu Ser Phe Ile Ser Ile Thr
                165                 170                 175

Pro Val Trp Leu Tyr Ala Arg Leu Ile Pro Phe Pro Gly Gly Ala Val
            180                 185                 190

Gly Cys Gly Ile Arg Leu Pro Asn Pro Asp Thr Asp Leu Tyr Trp Phe
        195                 200                 205

Thr Leu Tyr Gln Phe Phe Leu Ala Phe Ala Leu Pro Phe Val Val Ile
    210                 215                 220

Thr Ala Ala Tyr Val Arg Ile Leu Cys Tyr Thr Trp Glu Met Tyr Gln
225                 230                 235                 240

Gln Asn Lys Asp Ala Arg Cys Cys Asn Pro Ser Val Pro Lys Gln Arg
                245                 250                 255

Val Met Lys Val Thr Arg Thr Ala Ile Ala Ile Cys Leu Val Phe Phe
            260                 265                 270

Val Cys Trp Ala Pro Tyr Tyr Val Leu Gln Leu Thr Gln Leu Ser Ile
        275                 280                 285

Ser Arg Pro Thr Leu Thr Phe Val Tyr Leu Tyr Asn Ala Ala Ile Ser
    290                 295                 300

Leu Gly Tyr Ala Asn Ser Cys Leu Asn Pro Phe Val Tyr Ile Val Leu
305                 310                 315                 320

Cys Glu Thr Phe Arg Lys Arg Leu Val Leu Ser Val Lys Pro Ala Ala
                325                 330                 335

Gln Gly Gln Leu Arg Ala Val Ser Asn Ala Gln Thr Ala Asp Glu Glu
            340                 345                 350

Arg Thr Glu Ser Lys Gly Thr
        355
```

<210> SEQ ID NO 51
<211> LENGTH: 1038
<212> TYPE: DNA
<213> ORGANISM: artificial sequence
<220> FEATURE:
<223> OTHER INFORMATION: Cynomolgus macaque MCH1R/MCH2R C-terminal chimera

<400> SEQUENCE: 51

```
atggacctgg aagcctcgct gctgcccact ggtcccaaca ccagcaacac ctctgatggc     60

cccgataacc tcacctcggc aggatcacct cctcgctcag ggagcgtctc ctacatcaac    120

atcatcatgc cttcggtgtt cggcaccatc tgcctcctgg gcatcatcgg gaactccatg    180

gtcatcttcg cggtcgtgaa gaagtccaag ctgcactggt gcaacaatgt ccccgacatc    240

ttcatcatca acctctcggt ggtggatctc ctctttctcc tgggcatgcc cttcatgatc    300

caccagctca tgggcaatgg ggtgtggcac tttggggaga ccatgtgcac cctcatcacg    360

gccatggatg ccaatagtca gttcaccagc acctacatcc tgaccgccat ggccattgac    420

cgctacctgg ccaccgtcca ccccatctct tccacaaagt tccggaagcc ctctgtggcc    480

accctggtga tctgcctcct gtgggccctc tccttcatca gcatcacccc cgtgtggttg    540

tatgccagac tcatcccctt cccaggaggt gcagtgggct gcggcatccg cttgcccaac    600

ccggacactg acctttactg gttcaccctg taccagtttt tcctggcctt tgccctgccc    660

ttcgtggtca tcacggccgc atacgtgagg atcctgcagc gcatgacgtc ctcagtggcc    720

cccgcctccc agcgcagcat ccggctgcgg acaaagaggg tgacccgcac agccatcgcc    780

atctgcctgg tcttctttgt gtgctgggca ccctactatg tgctacagct gacccagttg    840
```

-continued

```
tccatcagcc gcccgaccct cacctttgtc tacctgtaca atgcggccat cagcttgggc    900

tacgccaaca gctgcctcaa cccctttgtg tacattgtgc tctgcgagac gttccggaaa    960

cgtctgcctc aaatccaaag gagagtgact gacaaggaaa tcaaaaatat gggaaacact   1020

ctgaaatcac acttttag                                                 1038


<210> SEQ ID NO 52
<211> LENGTH: 345
<212> TYPE: PRT
<213> ORGANISM: artificial sequence
<220> FEATURE:
<223> OTHER INFORMATION: Cynomolgus macaque MCH1R/MCH2R C-terminal
      chimera - amino acid sequence

<400> SEQUENCE: 52

Met Asp Leu Glu Ala Ser Leu Leu Pro Thr Gly Pro Asn Thr Ser Asn
1               5                   10                  15

Thr Ser Asp Gly Pro Asp Asn Leu Thr Ser Ala Gly Ser Pro Pro Arg
            20                  25                  30

Ser Gly Ser Val Ser Tyr Ile Asn Ile Ile Met Pro Ser Val Phe Gly
        35                  40                  45

Thr Ile Cys Leu Leu Gly Ile Ile Gly Asn Ser Met Val Ile Phe Ala
    50                  55                  60

Val Val Lys Lys Ser Lys Leu His Trp Cys Asn Asn Val Pro Asp Ile
65                  70                  75                  80

Phe Ile Ile Asn Leu Ser Val Val Asp Leu Leu Phe Leu Leu Gly Met
                85                  90                  95

Pro Phe Met Ile His Gln Leu Met Gly Asn Gly Val Trp His Phe Gly
            100                 105                 110

Glu Thr Met Cys Thr Leu Ile Thr Ala Met Asp Ala Asn Ser Gln Phe
        115                 120                 125

Thr Ser Thr Tyr Ile Leu Thr Ala Met Ala Ile Asp Arg Tyr Leu Ala
    130                 135                 140

Thr Val His Pro Ile Ser Ser Thr Lys Phe Arg Lys Pro Ser Val Ala
145                 150                 155                 160

Thr Leu Val Ile Cys Leu Leu Trp Ala Leu Ser Phe Ile Ser Ile Thr
                165                 170                 175

Pro Val Trp Leu Tyr Ala Arg Leu Ile Pro Phe Pro Gly Gly Ala Val
            180                 185                 190

Gly Cys Gly Ile Arg Leu Pro Asn Pro Asp Thr Asp Leu Tyr Trp Phe
        195                 200                 205

Thr Leu Tyr Gln Phe Phe Leu Ala Phe Ala Leu Pro Phe Val Val Ile
    210                 215                 220

Thr Ala Ala Tyr Val Arg Ile Leu Gln Arg Met Thr Ser Ser Val Ala
225                 230                 235                 240

Pro Ala Ser Gln Arg Ser Ile Arg Leu Arg Thr Lys Arg Val Thr Arg
                245                 250                 255

Thr Ala Ile Ala Ile Cys Leu Val Phe Phe Val Cys Trp Ala Pro Tyr
            260                 265                 270

Tyr Val Leu Gln Leu Thr Gln Leu Ser Ile Ser Arg Pro Thr Leu Thr
        275                 280                 285

Phe Val Tyr Leu Tyr Asn Ala Ala Ile Ser Leu Gly Tyr Ala Asn Ser
    290                 295                 300

Cys Leu Asn Pro Phe Val Tyr Ile Val Leu Cys Glu Thr Phe Arg Lys
305                 310                 315                 320
```

```
Arg Leu Pro Gln Ile Gln Arg Arg Val Thr Asp Lys Glu Ile Lys Asn
                325                 330                 335

Met Gly Asn Thr Leu Lys Ser His Phe
            340                 345
```

<210> SEQ ID NO 53
<211> LENGTH: 207
<212> TYPE: DNA
<213> ORGANISM: Macaca fascicularis

<400> SEQUENCE: 53

```
atgtcagtga gagccgcgaa ggagggagta gggagggcag ttgggcttgg aggcggcagc     60

ggctgccagg ctgccaagga agaccccctt cccgactgcg gggcttgcgc tcctggacaa    120

ggtggcaggc gctggaggct gccgcagcct gcgtgggtgg aggggagctc agcttggttg    180

tgggagccgg cgaccggcac tggctgg                                        207
```

<210> SEQ ID NO 54
<211> LENGTH: 69
<212> TYPE: PRT
<213> ORGANISM: Macaca fascicularis

<400> SEQUENCE: 54

```
Met Ser Val Arg Ala Ala Lys Glu Gly Val Gly Arg Ala Val Gly Leu
1               5                   10                  15

Gly Gly Gly Ser Gly Cys Gln Ala Ala Lys Glu Asp Pro Leu Pro Asp
            20                  25                  30

Cys Gly Ala Cys Ala Pro Gly Gln Gly Gly Arg Arg Trp Arg Leu Pro
        35                  40                  45

Gln Pro Ala Trp Val Glu Gly Ser Ser Ala Trp Leu Trp Glu Pro Ala
    50                  55                  60

Thr Gly Thr Gly Trp
65
```

<210> SEQ ID NO 55
<211> LENGTH: 1269
<212> TYPE: DNA
<213> ORGANISM: Macaca fascicularis

<400> SEQUENCE: 55

```
atgtcagtga gagccgcgaa ggagggagta gggagggcag ttgggcttgg aggcggcagc     60

ggctgccagg ctgccaagga agaccccctt cccgactgcg gggcttgcgc tcctggacaa    120

ggtggcaggc gctggaggct gccgcagcct gcgtgggtgg aggggagctc agcttggttg    180

tgggagccgg cgaccggcac tggctggatg gacctggaag cctcgctgct gcccactggt    240

cccaacacca gcaacacctc tgatggcccc gataacctca cctcggcagg atcacctcct    300

cgctcaggga gcgtctccta catcaacatc atcatgcctt cggtgttcgg caccatctgc    360

ctcctgggca tcatcgggaa ctccatggtc atcttcgcgg tcgtgaagaa gtccaagctg    420

cactggtgca acaatgtccc cgacatcttc atcatcaacc tctcggtggt ggatctcctc    480

tttctcctgg gcatgccctt catgatccac cagctcatgg gcaatggggt gtggcacttt    540

ggggagacca tgtgcaccct catcacggcc atggatgcca atagtcagtt caccagcacc    600

tacatcctga ccgccatggc cattgaccgc tacctggcca ccgtccaccc catctcttcc    660

acaaagttcc ggaagccctc tgtggccacc ctggtgatct gcctcctgtg ggccctctcc    720

ttcatcagca tcacccccgt gtggttgtat gccagactca tcccctttcc aggaggtgca    780
```

-continued

```
gtgggctgcg gcatccgctt gcccaacccg gacactgacc tttactggtt caccctgtac    840

cagtttttcc tggcctttgc cctgcccttc gtggtcatca cggccgcata cgtgaggatc    900

ctgcagcgca tgacgtcctc agtggccccc gcctcccagc gcagcatccg gctgcggaca    960

aagagggtga cccgcacagc catcgccatc tgcctggtct tctttgtgtg ctgggcaccc   1020

tactatgtgc tacagctgac ccagttgtcc atcagccgcc cgaccctcac ctttgtctac   1080

ctgtacaatg cggccatcag cttgggctac gccaacagct gcctcaaccc ctttgtgtac   1140

attgtgctct gcgagacgtt ccgcaaacgc ttggtccttt cggtgaagcc tgcagcccag   1200

gggcagcttc gcgctgtcag caacgctcag acggctgacg aggagaggac agaaagcaaa   1260

ggtacctga                                                           1269
```

<210> SEQ ID NO 56
<211> LENGTH: 422
<212> TYPE: PRT
<213> ORGANISM: Macaca fascicularis

<400> SEQUENCE: 56

```
Met Ser Val Arg Ala Ala Lys Glu Gly Val Gly Arg Ala Val Gly Leu
1               5                   10                  15

Gly Gly Gly Ser Gly Cys Gln Ala Ala Lys Glu Asp Pro Leu Pro Asp
            20                  25                  30

Cys Gly Ala Cys Ala Pro Gly Gln Gly Gly Arg Arg Trp Arg Leu Pro
        35                  40                  45

Gln Pro Ala Trp Val Glu Gly Ser Ser Ala Trp Leu Trp Glu Pro Ala
    50                  55                  60

Thr Gly Thr Gly Trp Met Asp Leu Glu Ala Ser Leu Leu Pro Thr Gly
65                  70                  75                  80

Pro Asn Thr Ser Asn Thr Ser Asp Gly Pro Asp Asn Leu Thr Ser Ala
                85                  90                  95

Gly Ser Pro Pro Arg Ser Gly Ser Val Ser Tyr Ile Asn Ile Ile Met
            100                 105                 110

Pro Ser Val Phe Gly Thr Ile Cys Leu Leu Gly Ile Ile Gly Asn Ser
        115                 120                 125

Met Val Ile Phe Ala Val Val Lys Lys Ser Lys Leu His Trp Cys Asn
    130                 135                 140

Asn Val Pro Asp Ile Phe Ile Ile Asn Leu Ser Val Val Asp Leu Leu
145                 150                 155                 160

Phe Leu Leu Gly Met Pro Phe Met Ile His Gln Leu Met Gly Asn Gly
                165                 170                 175

Val Trp His Phe Gly Glu Thr Met Cys Thr Leu Ile Thr Ala Met Asp
            180                 185                 190

Ala Asn Ser Gln Phe Thr Ser Thr Tyr Ile Leu Thr Ala Met Ala Ile
        195                 200                 205

Asp Arg Tyr Leu Ala Thr Val His Pro Ile Ser Ser Thr Lys Phe Arg
    210                 215                 220

Lys Pro Ser Val Ala Thr Leu Val Ile Cys Leu Leu Trp Ala Leu Ser
225                 230                 235                 240

Phe Ile Ser Ile Thr Pro Val Trp Leu Tyr Ala Arg Leu Ile Pro Phe
                245                 250                 255

Pro Gly Gly Ala Val Gly Cys Gly Ile Arg Leu Pro Asn Pro Asp Thr
            260                 265                 270

Asp Leu Tyr Trp Phe Thr Leu Tyr Gln Phe Phe Leu Ala Phe Ala Leu
        275                 280                 285
```

```
Pro Phe Val Val Ile Thr Ala Ala Tyr Val Arg Ile Leu Gln Arg Met
    290                 295                 300

Thr Ser Ser Val Ala Pro Ala Ser Gln Arg Ser Ile Arg Leu Arg Thr
305                 310                 315                 320

Lys Arg Val Thr Arg Thr Ala Ile Ala Ile Cys Leu Val Phe Phe Val
                325                 330                 335

Cys Trp Ala Pro Tyr Tyr Val Leu Gln Leu Thr Gln Leu Ser Ile Ser
            340                 345                 350

Arg Pro Thr Leu Thr Phe Val Tyr Leu Tyr Asn Ala Ala Ile Ser Leu
        355                 360                 365

Gly Tyr Ala Asn Ser Cys Leu Asn Pro Phe Val Tyr Ile Val Leu Cys
    370                 375                 380

Glu Thr Phe Arg Lys Arg Leu Val Leu Ser Val Lys Pro Ala Ala Gln
385                 390                 395                 400

Gly Gln Leu Arg Ala Val Ser Asn Ala Gln Thr Ala Asp Glu Glu Arg
                405                 410                 415

Thr Glu Ser Lys Gly Thr
            420
```

<210> SEQ ID NO 57
<211> LENGTH: 26
<212> TYPE: DNA
<213> ORGANISM: artificial sequence
<220> FEATURE:
<223> OTHER INFORMATION: MCH1R outer reverse primer

<400> SEQUENCE: 57

```
cacaggaggc agatcaccag ggtggc                                          26
```

<210> SEQ ID NO 58
<211> LENGTH: 22
<212> TYPE: DNA
<213> ORGANISM: artificial sequence
<220> FEATURE:
<223> OTHER INFORMATION: MCH1R inner reverse primer

<400> SEQUENCE: 58

```
ggtgctggtg aactgactat tg                                              22
```

<210> SEQ ID NO 59
<211> LENGTH: 1044
<212> TYPE: DNA
<213> ORGANISM: artificial sequence
<220> FEATURE:
<223> OTHER INFORMATION: alternate Cynomolgus macaque MCH1R/MCH2R N-terminal chimera - DNA sequence

<400> SEQUENCE: 59

```
atgaatccat ttcactcatc ttgttggaac acctctgccg aactttcaaa caaatcctgg      60

aataaagagt ttgcttatca aactgccagt gttgtagata caatcatcat gccttcggtg     120

ttcggcacca tctgcctcct gggcatcatc gggaactcca tggtcatctt cgcggtcgtg     180

aagaagtcca agctgcactg gtgcaacaat gtccccgaca tcttcatcat caacctctcg     240

gtggtggatc tcctctttct cctgggcatg cccttcatga tccaccagct catgggcaat     300

ggggtgtggc actttgggga gaccatgtgc accctcatca cggccatgga tgccaatagt     360

cagttcacca gcacctacat cctgaccgcc atggccattg accgctacct ggccaccgtc     420

caccccatct cttccacaaa gttccggaag ccctctgtgg ccaccctggt gatctgcctc     480
```

-continued

```
ctgtgggccc tctccttcat cagcatcacc cccgtgtggt tgtatgccag actcatcccc    540

ttcccaggag gtgcagtggg ctgcggcatc cgcttgccca acccggacac tgacctttac    600

tggttcaccc tgtaccagtt tttcctggcc tttgccctgc ccttcgtggt catcacggcc    660

gcatacgtga ggatcctgca gcgcatgacg tcctcagtgg cccccgcctc ccagcgcagc    720

atccggctgc ggacaaagag ggtgacccgc acagccatcg ccatctgcct ggtcttcttt    780

gtgtgctggg caccctacta tgtgctacag ctgacccagt tgtccatcag ccgcccgacc    840

ctcacctttg tctacctgta caatgcggcc atcagcttgg gctacgccaa cagctgcctc    900

aacccctttg tgtacattgt gctctgcgag acgttccgca aacgcttggt cctttcggtg    960

aagcctgcag cccaggggca gcttcgcgct gtcagcaacg ctcagacggc tgacgaggag   1020

aggacagaaa gcaaaggtac ctga                                          1044


<210> SEQ ID NO 60
<211> LENGTH: 347
<212> TYPE: PRT
<213> ORGANISM: artificial sequence
<220> FEATURE:
<223> OTHER INFORMATION: alternate MCH1R/MCH2R N-terminal chimera amino
      acid sequence

<400> SEQUENCE: 60

Met Asn Pro Phe His Ser Ser Cys Trp Asn Thr Ser Ala Glu Leu Ser
1               5                   10                  15

Asn Lys Ser Trp Asn Lys Glu Phe Ala Tyr Gln Thr Ala Ser Val Val
            20                  25                  30

Asp Thr Ile Ile Met Pro Ser Val Phe Gly Thr Ile Cys Leu Leu Gly
        35                  40                  45

Ile Ile Gly Asn Ser Met Val Ile Phe Ala Val Val Lys Lys Ser Lys
    50                  55                  60

Leu His Trp Cys Asn Asn Val Pro Asp Ile Phe Ile Ile Asn Leu Ser
65                  70                  75                  80

Val Val Asp Leu Leu Phe Leu Leu Gly Met Pro Phe Met Ile His Gln
                85                  90                  95

Leu Met Gly Asn Gly Val Trp His Phe Gly Glu Thr Met Cys Thr Leu
            100                 105                 110

Ile Thr Ala Met Asp Ala Asn Ser Gln Phe Thr Ser Thr Tyr Ile Leu
        115                 120                 125

Thr Ala Met Ala Ile Asp Arg Tyr Leu Ala Thr Val His Pro Ile Ser
    130                 135                 140

Ser Thr Lys Phe Arg Lys Pro Ser Val Ala Thr Leu Val Ile Cys Leu
145                 150                 155                 160

Leu Trp Ala Leu Ser Phe Ile Ser Ile Thr Pro Val Trp Leu Tyr Ala
                165                 170                 175

Arg Leu Ile Pro Phe Pro Gly Gly Ala Val Gly Cys Gly Ile Arg Leu
            180                 185                 190

Pro Asn Pro Asp Thr Asp Leu Tyr Trp Phe Thr Leu Tyr Gln Phe Phe
        195                 200                 205

Leu Ala Phe Ala Leu Pro Phe Val Val Ile Thr Ala Ala Tyr Val Arg
    210                 215                 220

Ile Leu Gln Arg Met Thr Ser Ser Val Ala Pro Ala Ser Gln Arg Ser
225                 230                 235                 240

Ile Arg Leu Arg Thr Lys Arg Val Thr Arg Thr Ala Ile Ala Ile Cys
                245                 250                 255
```

-continued

```
Leu Val Phe Phe Val Cys Trp Ala Pro Tyr Tyr Val Leu Gln Leu Thr
            260                 265                 270

Gln Leu Ser Ile Ser Arg Pro Thr Leu Thr Phe Val Tyr Leu Tyr Asn
        275                 280                 285

Ala Ala Ile Ser Leu Gly Tyr Ala Asn Ser Cys Leu Asn Pro Phe Val
    290                 295                 300

Tyr Ile Val Leu Cys Glu Thr Phe Arg Lys Arg Leu Val Leu Ser Val
305                 310                 315                 320

Lys Pro Ala Ala Gln Gly Gln Leu Arg Ala Val Ser Asn Ala Gln Thr
                325                 330                 335

Ala Asp Glu Glu Arg Thr Glu Ser Lys Gly Thr
            340                 345
```

MELANIN CONCENTRATING HORMONE RECEPTORS

CROSS-REFERENCE TO RELATED APPLICATIONS

This application is a continuation-in-part of U.S. patent application Ser. No. 10/126,764, filed Apr. 18, 2002, which claims priority to U.S. Provisional Application 60/284,835, filed Apr. 19, 2001.

FIELD OF THE INVENTION

The present invention relates generally to tools useful for the discovery of drugs for the treatment of conditions associated with melanin concentrating hormone (MCH) receptor activation in humans and other animals. The invention is more specifically related to polypeptides comprising monkey MCH type 1 receptor (MCH1R) sequences, including monkey MCH1R and chimeric MCH receptors, and to polynucleotides encoding such polypeptides. Such polypeptides and polynucleotides may be used in the identification of agents that modulate MCH receptor activity.

DESCRIPTION OF THE SEQUENCE LISTING

SEQ ID NO:1 Cynomolgus macaque MCH1R DNA sequence

SEQ ID NO:2 Cynomolgus macaque MCH1R amino acid sequence

SEQ ID NO:3 Amino acid sequence of the $HiS_{6x}$, epitope

SEQ ID NO:4 Amino acid sequence of the FLAG epitope

SEQ ID NO:5 Human MCH1R DNA sequence

SEQ ID NO:6 Human MCH1R amino acid sequence

SEQ ID NO:7 5' Cynomolgus macaque MCH1R primer

SEQ ID NO:8 3' Cynomolgus macaque MCH1R primer

SEQ ID NO:9 Human NPY1 receptor DNA CDS only

SEQ ID NO:10 Human NPY1 receptor amino acid sequence

SEQ ID NO:11 Human NPY1 receptor BspE forward primer for CT

SEQ ID NO:12 Human NPY1 receptor reverse primer for CT

SEQ ID NO:13 Human NPY1 receptor BspE—Not I fragment for CT

SEQ ID NO:14 Human NPY1 receptor IC3 loop Sense oligo

SEQ ID NO:15 Human NPY1 receptor IC3 loop Anti-sense oligo

SEQ ID NO:16 Human MCH1R plus BspE Site added for C-terminal chimeras

SEQ ID NO:17 Human MCH1R/NPY1 IC3 loop chimera—DNA CDS only

SEQ ID NO:18 Human MCH1R/NPY1 IC3 loop chimera—amino acid sequence

SEQ ID NO:19 Human MCH1R/NPY1 C-terminal chimera—DNA CDS only

SEQ ID NO:20 Human MCH1R/NPY1 C-terminal chimera—amino acid sequence

SEQ ID NO:21 Human MCH1R/NPY1 IC3 loop chimera in pcDNA3.1Plus (pN105)

SEQ ID NO:22 Human MCH1R/NPY1 C-terminal chimera in pcDNA3.1Plus (pN107)

SEQ ID NO:23 Human beta-2 adrenergic receptor—DNA sequence

SEQ ID NO:24 Human beta-2 adrenergic receptor amino acid sequence

SEQ ID NO:25 Human beta-2 adrenergic receptor C-terminal forward primer

SEQ ID NO:26 Human beta-2 adrenergic receptor C-terminal reverse primer

SEQ ID NO:27 Human MCH1R/beta-2 adrenergic receptor C-term. chimera—DNA CDS

SEQ ID NO:28 Human MCH1R/beta-2 adrenergic receptor C-term. chimera—amino acid sequence SEQ ID NO:29 Human MCH1R/beta-2 adrenergic receptor C-term. chimera in pcDNA3.1Plus (pN 125)

SEQ ID NO:30 Amino acid residues 30–60 of SEQ ID NO:2

SEQ ID NO:31 Human MCH1R forward primer

SEQ ID NO:32 Human MCH1R reverse primer

SEQ ID NO:33 Cynomolgus macaque MCH2R clone A DNA sequence

SEQ ID NO:34 Cynomolgus macaque MCH2R clone A amino acid sequence

SEQ ID NO:35 Cynomolgus macaque MCH2R clone B DNA sequence

SEQ ID NO:36 Cynomolgus macaque MCH2R clone B amino acid sequence

SEQ ID NO:37 Cynomolgus macaque MCH2R DNA sequence

SEQ ID NO:38 Canine MCH2R DNA sequence

SEQ ID NO:39 Canine MCH2R amino acid sequence

SEQ ID NO:40 Cynomolgus macaque MCH1R with BspE Site for C-term. chimeras

SEQ ID NO:41 Cynomolgus macaque MCH1R/human NPY1 IC3 loop chimera—DNA sequence

SEQ ID NO:42 Cynomolgus macaque MCH1R/human NPY1 IC3 loop chimera—amino acid sequence SEQ ID NO:43 Cynomolgus macaque MCH1R/human NPY1 C-term. chimera—DNA sequence SEQ ID NO:44 Cynomolgus macaque MCH1R/human NPY1 C-term. chimera—amino acid sequence SEQ ID NO:45 Cynomolgus macaque MCH1R/human beta-2 adrenergic receptor C-terminal chimera—DNA sequence SEQ ID NO:46 Cynomolgus macaque MCH1R/human beta-2 adrenergic receptor C-terminal chimera—amino acid sequence SEQ ID NO:47 Cynomolgus macaque MCH1R/MCH2R N-terminal chimera—DNA sequence SEQ ID NO:48 Cynomolgus macaque MCH1R/MCH2R N-terminal chimera—amino acid sequence SEQ ID NO:49 Cynomolgus macaque MCH1R/MCH2R IC3 LOOP chimera—DNA sequence SEQ ID NO:50 Cynomolgus macaque MCH1R/MCH2R IC3 LOOP chimera—amino acid sequence SEQ ID NO:51 Cynomolgus macaque MCH1R/MCH2R C-terminal chimera—DNA sequence SEQ ID NO:52 Cynomolgus macaque MCH1R/MCH2R C-terminal chimera—amino acid sequence SEQ ID NO:53 Cynomolgus macaque MCH1R 5' extension—DNA sequence SEQ ID NO:54 Cynomolgus macaque MCH1R 5' extension—amino acid sequence SEQ ID NO:55 Cynomolgus macaque MCH1R long form 5'—DNA sequence SEQ ID NO:56 Cynomolgus macaque MCH1R long form 5'—amino acid sequence SEQ ID NO:57 MCH1R outer reverse primer SEQ ID NO:58 MCH1R inner reverse primer SEQ ID NO:59 Alternate cynomolgus macaque MCH1R/MCH2R N-terminal chimera—DNA sequence SEQ ID NO:60 Alternate cynomolgus macaque MCH1R/MCH2R N-terminal chimera—amino acid sequence

BACKGROUND OF THE INVENTION

Melanin concentrating hormone, or MCH, is a cyclic 19 amino acid neuropeptide that functions as a regulator of food intake and energy balance. In many vertebrate species, including humans, MCH is produced in the hypothalamus, which is associated with behaviors such as eating, drinking, aggression and sexual behavior. MCH is also produced at various peripheral sites, including the gastrointestinal tract and testis.

The postulated role of MCH in feeding behavior and body weight is confirmed by the finding that i.c.v. injection of MCH into the lateral ventrical of the hypothalamus increases caloric consumption in rats over similarly treated control animals. Furthermore, rats having the ob/ob genotype exhibit a 50–80% increase in MCH mRNA expression as compared to leaner ob/+ genotype mice. MCH knockout mice are leaner than mice that produce MCH, but are otherwise genetically identical, due to hypophagia and an increased metabolic rate.

MCH activity is mediated via binding to specific receptors. Like other G protein-coupled receptors (e.g., neuropeptide Y (NPY) and beta-adrenergic receptors), MCH receptors are membrane-spanning proteins that consist of a single contiguous amino acid chain comprising an extracellular N-terminal domain, seven membrane-spanning alpha helical domains (connected by three intracellular loop domains alternating with three extracellular loop domains), and an intracellular C-terminal domain. Signal transduction is initiated by the binding of MCH to the receptor. This elicits conformational changes in the extracellular domains. When the receptor is functioning properly, these conformational changes propagate through the transmembrane domains and result in a coordinated change in the intracellular portions of the receptor. This precise alteration in the intracellular domains acts to trigger the associated G-protein complex to modulate intracellular signaling.

MCH1R is a 353 amino acid, 7-transmembrane, alpha-helical, G protein-coupled receptor, initially reported as orphan receptor SCL-1 by Kolakowski et al. (1996) *FEBS Lett.* 398:253–58 and Lakaye et al. (1998) *Biochim. Biophys. Acta* 1401:216–220. Chambers et al. (1999) *Nature* 400: 261–65 and Saito et al. (1999) *Nature* 400:265–69 subsequently showed that SLC-1 was an MCH receptor. Immunohistochemistry studies of rat brain sections indicate that MCH1R is widely expressed in brain. MCH1R expression is found in olfactory tubercle, cerebral cortex, substantia nigra, basal forebrain CA1, CA2, and CA3 field of the hippocampus, amygdala, and in nuclei of the hypothalamus, thalamus, midbrain and hindbrain. Strong signals are observed in the ventromedial and dorsomedial nuclei of the hypothalamus, two areas of the brain involved in feeding behavior. Upon binding MCH, MCH1R expressed in HEK 293 cells mediates a dose-dependent release of intracellular calcium. Cells expressing MCH1R also exhibit a pertussis toxin sensitive dose-dependent inhibition of forskolin-elevated cyclic AMP, indicating that the receptor couples to a $G_{i/o}$ G-protein alpha subunit.

Agents capable of modulating MCH receptor activity are highly desirable for the treatment of obesity, eating disorders (e.g., bulimia and anorexia), sexual disorders (e.g., anorgasmic or psychogenic impotence) and metabolic disorders, such as diabetes. Isolated MCH receptors (e.g., as components of membrane preparations), cells expressing such receptors and cloned MCH receptor genes are needed to facilitate the discovery of such agents.

Accordingly, there is a need in the art for additional MCH receptor sequences. The present invention fulfills this need, and provides further related advantages.

SUMMARY OF THE INVENTION

Briefly stated, the present invention provides compositions and methods for the identification of therapeutic agents useful for treating conditions associated with MCH receptor activation. In one aspect, the present invention provides isolated MCH1R polypeptides that comprise a monkey MCH1R sequence. Within certain embodiments, such polypeptides comprise at least 30 consecutive amino acids of the cynomolgus macaque (*Macaca fascicularis*) MCH1R sequence provided in SEQ ID NO:56; preferably, the 30 consecutive amino acids are located within residues 1–130 of SEQ ID NO:56. Preferably, such polypeptides exhibit MCH1R ligand binding activity. Certain polypeptides comprise at least amino acids 30–60 of the cynomolgus macaque sequence provided in SEQ ID NO:2.

Within related aspects, the present invention provides MCH1R chimeric polypeptides that comprise a MCH1R sequence, wherein one or more domains are replaced with a corresponding domain of a different G protein-coupled receptor. Preferably, from 1 to 3 domains are replaced; more preferably 1 domain is replaced. For example, the intracellular loop 3, N-terminal domain or C-terminal domain of MCH1R may be replaced with a corresponding domain of MCH2R, $NPY_1$ receptor, beta-2-adrenergic receptor or MCH1R from another species. Representative chimeric polypeptides include those provided in SEQ ID NOs:18, 20, 28, 42, 44, 46, 48, 50, 52 and 60.

Within further aspects, the present invention provides isolated polynucleotides (e.g., DNA or RNA) that encode a MCH1R polypeptide or chimeric polypeptide as described above. Such polynucleotides may comprise a native sequence (e.g., SEQ ID NO:1 or 55) or may contain changes relative to the native sequence that do not affect the sequence of the encoded polypeptide. Certain such polynucleotides comprise at least 90 consecutive nucleotides of SEQ ID NO:55.

The present invention further provides, within related aspects, expression vectors (e.g., plasmids and viral vectors) that comprise a polynucleotide as described above, as well as transgenic host cells (i.e., cells comprising at least one heterologous expression vector) that express a polypeptide as described above (e.g., as a result of being transformed or transfected with at least one such expression vector) and cell membrane preparations isolated from such transgenic cells.

Methods are further provided, within other aspects, for determining MCH receptor binding activity of a compound, comprising the steps of: (a) contacting a compound with at least one transgenic cell or with a cell membrane preparation as described above; and (b) detecting binding of the compound to the cell(s) or cell membrane preparation. Binding may be detected, for example, by measuring the ability of the compound to compete with detectably labeled MCH for binding to the membrane preparation.

Within further aspects, the present invention provides methods for detecting MCH receptor modulating activity of a compound, comprising the steps of: (a) contacting a compound with at least one transgenic cell as described above; (b) detecting a cellular property (e.g., a level of $Ca^{2+}$ in the contacted cell(s)); and (c) comparing the detected cellular property with a property detected in control cells in the absence of compound (e.g., comparing a detected level of $Ca^{2+}$ with a level of $Ca^{2+}$ detected in control cells in the absence of compound). Within certain embodiments, before step (a), the transgenic cells are: (i) contacted with an indicator of intracellular $Ca^{2+}$ concentration to yield indicator-loaded cells; and (ii) washed. The level of $Ca^{2+}$ may be detected, for example, by quantifying $Ca^{2+}$-concentration-dependent changes in the properties of the indicator of intracellular $Ca^{2+}$.

Methods are further provided, within other aspects, for detecting MCH receptor agonist activity of a compound, comprising the steps of: (a) contacting transgenic cells as described above with an indicator of intracellular $Ca^{2+}$ concentration, to yield indicator-loaded cells; (b) washing the indicator-loaded cells; (c) contacting a portion of the washed, indicator-loaded cells with a compound to yield test cells; (d) separately detecting a property of the indicator of intracellular $Ca^{2+}$ concentration in the test cells and in a second portion of the washed and indicator-loaded cells; and (e) comparing the detected property of the test cells with the detected property of the washed indicator-loaded cells.

The present invention further provides methods for detecting MCH receptor antagonist activity of a compound, comprising the steps of: (a) contacting a compound and an MCH receptor agonist with transgenic cells as described above; (b) detecting a level of $Ca^{2+}$ in the contacted cells; and (c) comparing the detected level of $Ca^{2+}$ with a level of $Ca^{2+}$ detected in control cells in the presence of agonist and in the absence of compound. In certain embodiments, prior to the step of contacting with compound an agonist, the transgenic cells are: (i) contacted with an indicator of intracellular $Ca^{2+}$ concentration and (ii) washed.

Methods are further provided for detecting MCH receptor antagonist activity of a compound, comprising the steps of: (a) contacting transgenic cells as described above with an indicator of intracellular $Ca^{2+}$ concentration, to yield indicator-loaded cells; (b) washing the indicator-loaded cells; (c) contacting a first portion of the washed, indicator-loaded cells with a compound and an MCH receptor agonist to yield test cells; (d) contacting a second portion of the washed, indicator-loaded cells with an MCH receptor agonist to yield control cells; (e) separately detecting a property of the indicator of intracellular $Ca^{2+}$ in the test cells and in the control cells; and (f) comparing the detected property of the test cells with the detected property of the control cells.

These and other aspects of the present invention will become apparent upon reference to the following detailed description and attached drawings.

BRIEF DESCRIPTION OF THE DRAWINGS

FIGS. 1A and 1B depict an alignment of the amino acid sequences of (a) cynomolgus macaque MCH1R long form (SEQ ID NO:56); (b) cynomolgus macaque MCH1R (SEQ ID NO:2), (c) the human somatostatin-like protein recited in SEQ ID NO:2 of U.S. Pat. No. 6,008,012, (d) human MCH1R and (e) rat MCH1R.

FIGS. 2A and 2B depict an alignment of the amino acid sequences of (a) cynomolgus macaque MCH1R (SEQ ID NO:2), (b) cynomolgus macaque MCH1R long form (SEQ ID NO:56); and (c) the human MCH1 recited as SEQ ID NO:2 of U.S. Pat. No. 6,291,195 (encoded by GenBank accession number AR169785).

DETAILED DESCRIPTION OF THE INVENTION

As noted above, the present invention is generally directed to compounds and methods for identifying therapeutic agents that may be used to treat conditions associated with MCH receptor activation. Compounds provided herein include polypeptides that comprise a monkey MCH1R sequence, as well as polynucleotides that encode such polypeptides. Chimeric polypeptides comprising a MCH1R sequence in which one or more domains are replaced with a corresponding domain of another G protein-coupled receptor are also provided. MCH1R polypeptides and polynucleotides may be used to identify therapeutic agents, as discussed in further detail below.

MCH Receptor Polynucleotides

Any polynucleotide that encodes an MCH1R polypeptide or chimera as described herein is encompassed by the present invention. Polynucleotides may be single-stranded (coding or antisense) or double-stranded, and may be DNA (e.g., genomic, cDNA or synthetic) or RNA, such as mRNA molecules. Modified analogues of such polynucleotides are also encompassed (e.g., phosphorthioate derivatives). Additional coding or non-coding sequences may, but need not, be present within a polynucleotide of the present invention, and a polynucleotide may, but need not, be linked to other molecules and/or support materials.

Certain polynucleotides encode a cynomolgus macaque MCH1R polypeptide. Such polynucleotides generally encode at least 30 consecutive amino acid residues of the MCH1R sequence provided in SEQ ID NO:56. Preferably, at least 30 consecutive amino acids located between residues 1 and 130 are encoded by such polynucleotides, and the encoded polypeptide exhibits MCH1R ligand binding activity (i.e., detectably bind MCH within the assay provided in Example 4). Certain polynucleotides encode at least amino acid residues 30–60 (SEQ ID NO:30) of a cynomolgus macaque MCH1R protein sequence provided in SEQ ID NO:2. For less than full length MCH1R sequences, deletions at the 3' end are generally preferred. Certain preferred cynomolgus macaque MCH1R polynucleotides encode at least amino acid residues 2–64 of SEQ ID NO:2, more preferably at least amino acid residues 2 to 230 of SEQ ID NO:2 and still more preferably at least amino acid residues 2 to 353 of SEQ ID NO:2. Certain such polynucleotides comprise at least 90 consecutive nucleotides, preferably at least nucleotides 28–220, of a cynomolgus macaque MCH1R sequence provided herein (SEQ ID NO:1).

Cynomolgus macaque MCH1R polynucleotides may, but need not, further encode the 5' sequence provided in SEQ ID NO:54 (by comprising, for example, the 5' sequence recited in SEQ ID NO:53). The 5' sequence is also shown as residues 1 to 69 of SEQ ID NO:56 (encoded by nucleotides 1 to 207 of SEQ ID NO:55). Polynucleotides with this 5' sequence are referred to herein as MCH1R long form polynucleotides.

The present invention also provides polynucleotides that encode chimeric MCH1R polypeptides. Such chimeric polypeptides, as discussed in more detail herein, generally comprise a MCH1R sequence (e.g., monkey, as described herein, or human, as in SEQ ID NO:6) in which one or more domains have been replaced with a corresponding domain of a different G protein-coupled receptor (e.g., MCH1R from a different species; a different MCH receptor such as MCH2R; NPY1 receptor; or beta-2-adrenergic receptor). Certain such chimeric polypeptides are MCH1R intracellular loop 3 chimeras (i.e., MCH1R sequences in which the amino acid sequence of the third intracellular loop has been replaced by the amino acid sequence of the third intracellular loop of another G protein-coupled receptor), C-terminal chimeras or N-terminal chimeras. As noted above, polynucleotides encoding such chimeras may comprise naturally occurring and/or non-naturally occurring sequences.

Naturally-occurring sequences that may be used to construct chimeric polynucleotides are provided herein and in the literature (e.g., SEQ ID NO:9 and GenBank Accession Number M88461 for human NPY1 receptor sequence; SEQ ID NO:23 and Accession Number Y00106 for human beta-2 adrenergic receptor; SEQ ID NO:33, 35 or 37 for macaque MCH2R; SEQ ID NO:38 for canine MCH2R). A precise coding sequence suitable for the construction of a chimera is readily determined by those of ordinary skill in the art from the nucleotide and amino acid sequences provided herein, and may be constructed using standard recombinant techniques.

Polynucleotides complementary to the MCH1R sequences discussed above (or portions thereof) are also encompassed by the present invention. Such polynucleotides include, for example, PCR products and restriction fragments, and may find use as probes or primers. Probes may be labeled with a variety of reporter groups, such as radionuclides and enzymes. Complementary polynucleotides generally hybridize to a MCH1R polynucleotide under stringent conditions. Stringent conditions include, for example, hybridization to filter-bound DNA in 0.5 M $NaHPO_4$, 0.5% sodium dodecyl sulfate (SDS), 1 mM EDTA at 65° C., and washing in 0.1×SSC/0.1% SDS at 68° C.). For short oligonucleotide probes, washing may be performed in 6×SSC/0.05% sodium pyrophosphate at 37° C. (for 14-base oligos), 48° C. (for 17-base oligos), 55° C. (for 20-base oligos), and 60° C. (for 23-base oligos). Other stringent conditions include overnight hybridization at 42° C. in a solution comprising: 50% formamide, 5×SSC (150 mM NaCl, 15 mM trisodium citrate), 50 mM sodium phosphate (pH 7.6), 5× Denhardt's solution, 10% dextran sulfate, and 20 μg/mL denatured, sheared salmon sperm DNA, followed by washing the filters in 0×SSC at about 65° C.

It will be appreciated by those of ordinary skill in the art that, as a result of the degeneracy of the genetic code, there are many nucleotide sequences that encode the polypeptides provided herein. Some of these polynucleotides bear minimal homology to the nucleotide sequence of any naturally occurring gene. Nonetheless, polynucleotides that vary due to differences in codon usage are specifically contemplated by the present invention. Additionally, it will be apparent that sequence changes may be made in the non-coding regions of the polynucleotides without altering the amino acid sequence of the protein product.

The present invention also encompasses polynucleotides that encode amino acid sequences with up to 15 (preferably no more than 10, more preferably no more than 5) amino acid substitutions relative to a naturally occurring monkey MCH1R sequence, provided that any substitutions do not substantially diminish receptor function (e.g., determined using a calcium mobilization assay as described within Example 5 herein) and are non-human (i.e., do not result in a human MCH1R sequence (SEQ ID NO:6)). In general, as discussed below, conservative substitutions are preferred. MCH1R polynucleotides preferably encode a polypeptide that does not comprise one or more of the following residues: (1) Ala in the position corresponding to position 14 of SEQ ID NO:2; (2) Thr in the position corresponding to position 33 of SEQ ID NO:2; (3) Ile in the position corresponding to position 36 of SEQ ID NO:2; and/or (4) Thr in the position corresponding to position 60 of SEQ ID NO:2. More preferably, an MCH1R polynucleotide encodes a polypeptide having at least one, preferably at least three or four, of the following residues (or conservative substitutions thereof): (1) Thr in the position corresponding to position 14 of SEQ ID NO:2; (2) Ser in the position corresponding to position 33 of SEQ ID NO:2; (3) Val in the position corresponding to position 36 of SEQ ID NO:2; and/or (4) Met in the position corresponding to position 60 of SEQ ID NO:2. The phrase "in the position corresponding to," as used herein, refers to the position within the polypeptide that, when aligned with SEQ ID NO:2 (using, for example, a ClustalW alignment) is matched with the specified residue of SEQ ID NO:2.

Polynucleotides provided herein may further comprise additional sequences. For example, an optimized translation initiation sequence (Kozak sequence) may be added to the 5' terminus. In-frame additions of sequences encoding antibody recognition sites may also, or alternatively, be included. Such sites are well known in the art, and include, but are not limited to the His-6× (hexa-histidine) epitope (SEQ ID NO:3) which is specifically bound by the Monoclonal Anti-polyhistidine Clone HIS-1 monoclonal antibody (Sigma, St. Louis No. H1029), and the FLAG epitope (SEQ ID NO:4) which is specifically bound by the FLAG-M2 monoclonal antibody (Sigma, St. Louis No. F3165). Techniques for making such modifications are also well known in the art, and may be readily carried out using routine methods or by using prepared kits, such as the Sigma Mammalian FLAG Expression Kits (Sigma, St. Louis; e.g., Nos. FL-MA and FL-MC). Preferably, fusions are made as in-frame amino- (N-) or carboxy- (C) terminal fusions. C-terminal fusions are generally less prone to interfere with membrane insertion of the fusion protein, and are commonly used when properly membrane-inserted fusion proteins (e.g., proteins retaining receptor signal transduction function) are desired.

Polynucleotides are preferably "isolated" (i.e., represent at least 10% of total nucleic acid molecules, preferably at least 20% and more preferably at least 50% of total nucleic acid molecules, within a sample or preparation). Unless otherwise specified, a polynucleotide comprising a given sequence may be of any length.

Polynucleotides may be prepared using any of a variety of well known techniques. For example, polynucleotides (or portions thereof) may be amplified via polymerase chain reaction (PCR), using sequence-specific primers designed based on the sequences provided herein, which may be purchased or synthesized. Portions of a desired polynucleotide obtained using PCR may be assembled into a single contiguous sequence by ligating suitable fragments, using well known techniques. Alternatively, amplified portion may be used to isolate a full length gene from a suitable library (e.g., one or more brain regions such as hypothalamus) using well known hybridization techniques. Within such techniques, a library (cDNA or genomic) is screened using one or more polynucleotide probes or primers corresponding to a portion of the desired sequence. Preferably, a library is size-selected for larger molecules. Random primed libraries may also be preferred for obtaining 5' regions of genes.

It will be apparent that primers designed based on the sequences provided herein may be used to obtain polynucleotides encoding MCH1R from other species, and that such polynucleotides are within the scope of the present invention.

RNA molecules may be generated by in vitro or in vivo transcription of DNA sequences encoding an MCH1R polypeptide, provided that the DNA is incorporated into a vector with a suitable RNA polymerase promoter (such as T7 or SP6). For example, antisense RNA may be generated from suitable cDNA constructs that have been introduced into cells or tissues to facilitate the production of antisense RNA.

Polynucleotides containing nucleotide substitutions, additions and deletions may generally be prepared by any method known in the art, including chemical synthesis by, for example, solid phase phosphoramidite chemical synthesis. Modifications in a polynucleotide sequence may also be introduced using standard mutagenesis techniques, such as oligonucleotide-directed site-specific mutagenesis.

Nucleotide sequences as described herein may be joined to a variety of other nucleotide sequences using established recombinant DNA techniques. For example, a polynucleotide may be cloned into any of a variety of cloning vectors, including plasmids, phagemids, lambda phage derivatives and cosmids. Vectors of particular interest include expression vectors, replication vectors, probe generation vectors and sequencing vectors. In general, a vector will contain an origin of replication functional in at least one organism, convenient restriction endonuclease sites and one or more selectable markers. Other elements will depend upon the desired use, and will be apparent to those of ordinary skill in the art.

MCH Receptor Polypeptides

The term "MCH1R polypeptide," as used herein, refers to monkey MCH1R polypeptides (i.e., polypeptides comprising a naturally-occurring monkey MCH1R sequence or variant thereof containing amino acid insertions, deletions and/or substitutions as described herein), as well as MCH1R chimeric polypeptides comprising an MCH1R sequence from any species in which one or more domains are replaced with corresponding domain(s) from a different G protein-coupled receptor. Cynomolgus macaque MCH1R polypeptides provided herein generally comprise at least 30 consecutive amino acid residues of SEQ ID NO:56, preferably at least 30 consecutive amino acids present between amino acids 1 and 130 of SEQ ID NO:56. Certain preferred MCH1R polypeptides comprise at least amino acid residues 30–60 (SEQ ID NO:30), 2–64 or 2 to 230 of SEQ ID NO:2. Certain such polypeptides comprise at least amino acid residues 2 to 353 of SEQ ID NO:2. MCH1R long form polypeptides may further comprise the N-terminal sequence shown in SEQ ID NO:54 (and as amino acids 1–69 of SEQ ID NO:56, which provides the full long form MCH1R sequence). Unless otherwise specified, a polypeptide comprising a given sequence may be of any length.

MCH1R polypeptides are preferably isolated. A polypeptide is said to be "isolated" if it represents at least 1% of total polypeptide molecules, preferably at least 10% and more preferably at least 20% of total polypeptide molecules, within a sample or preparation).

Certain MCH1R polypeptides and chimeric polypeptides exhibit MCH binding activity and/or receptor function. In other words, such polypeptides detectably bind MCH within a MCH1R ligand binding assay (i.e., within the assay provided in Example 4) and/or display detectable activity within a calcium mobilization assay as provided in Example 5. References herein to "MCH1R ligand binding activity" refer to binding detected within the assay described in Example 4.

As noted above, amino acid substitutions may be made within cynomolgus macaque MCH1R sequences at up to 15 amino acid residues, preferably at no more than 10 residues and more preferably at no more than 5 residues. Any substitutions should not substantially diminish MCH1R ligand binding activity and/or MCH receptor function. A substitution does not "substantially diminish" binding activity or receptor function if the activity within a ligand binding assay or calcium mobilization assay is enhanced, unchanged or diminished by no more than 10%, relative to the native MCH1R sequence of SEQ ID NO:2. In addition, substitutions should not result in a human MCH1R sequence (SEQ ID NO:6). Preferably, MCH1R polypeptides retain at least one, preferably all four, of the following amino acid residues: (1) Thr in the position corresponding to position 14 of SEQ ID NO:2; (2) Ser in the position corresponding to position 33 of SEQ ID NO:2; (3) Val in the position corresponding to position 36 of SEQ ID NO:2; and/or (4) Met in the position corresponding to position 60 of SEQ ID NO:2.

In general, conservative substitutions are preferred. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include Lys and Arg; and amino acids with uncharged polar head groups having similar hydrophilicity values include Leu, Ile and Val; Gly and Ala; Asn and Gin; and Ser, Thr, Phe and Tyr. Other groups of amino acids that may represent conservative changes include: (1) Ala, Pro, Gly, Glu, Asp, Gin, Asn, Ser, Thr; (2) Cys, Ser, Tyr, Thr; (3) Val, Ile, Leu, Met, Ala, Phe; (4) Lys, Arg, His; and (5) Phe, Tyr, Trp, His.

Chimeric MCH1R polypeptides are those in which at least one domain is derived from a MCH1R sequence (e.g., monkey, human or rat), with one or more domains replaced with corresponding domain(s) from a different G protein-coupled receptor. As noted above, MCH receptors contain an N-terminal domain, seven transmembrane domains interspersed with three intracellular loop domains alternating with three extracellular loop domains, and an intracellular C-terminal domain. The precise locations of domains may be conveniently calculated by computer analysis of hydrophobicity or hydrophilicity using hydropathy profiles, such as standard Kyte-Doolittle analysis (Kyte and Doolittle, *J. Mol. Biol.* 157:105–32, 1982). The transition boundaries between the hydrophobic and hydrophilic domains are typically marked by the presence of charged or polar (hydrophilic) amino acid residues at the beginning or end of a stretch of nonpolar (hydrophobic) residues. The N-terminus extends into the extracellular space and the C-terminus into the cell cytoplasm. Each of the seven hydrophobic domains is about 20–25 amino acids long, assumes a largely alpha helical conformation, and crosses once through the plasma membrane, its entire extent generally embedded in the membrane. The hydrophobic domains are thus also referred to as transmembrane domains or membrane-spanning alpha helical domains, while the hydrophilic domains are referred to as either extracellular or intracellular domains, depending upon their predicted locations in a functional, membrane-bound receptor. The hydrophilic domains interconnecting transmembrane domains form loops within the cytoplasm or extracellular space, and are consequently referred to as cytoplasmic or extracellular loop domains.

G protein-coupled receptors, including MCH receptors, have been structurally modeled as to secondary and tertiary structural conformation, and the precise locations of the extracellular, transmembrane and intracellular domains within their primary structures (i.e., their amino acid sequences) are well known and generally agreed to in the art. The location of G protein-coupled receptor domains may be determined using the model of Baldwin (*EMBO J.* 12:1693–703, 1993), in which certain conserved residues are initially located and aligned. For constructing chimeric polypeptides provided herein, locations of domains within the MCH1R polypeptide of SEQ ID NO:2 are generally as follows: extracellular N-terminal (residues 1 to 40), seven transmembrane domains (approximately residues 41–66, 76–101, 117–142, 158–183, 207–232, 254–279 and 291–316, respectively) interspersed with three intracellular loop domains alternating with three extracellular loop domains, and an intracellular C-terminal domain (residues 317 to end). Intracellular loop 3 consists of residues 233–253. Any of these domains may be replaced with a corresponding domain from MCH1R of a different species, MCH2R, or a non-MCH receptor such as $NPY_1$ or beta-2 adrenergic receptor. It will be apparent that, when replacing one domain with another, the residue numbers provided above may be altered slightly in either direction in order to facilitate cloning. In general, residue numbers may be altered by up to 6, preferably up to 4, amino acid residues in either direction. For example, if intracellular loop 3 (IC3 loop) is to be replaced, the replaced portion may begin at any residue between 227 and 239, and may end at any residue between 247 and 259. Preferred macaque MCH1R IC3 loop chimeras contain residues 1–232 and 254–353 of MCH1R, with residues corresponding to MCH1R 233–253 derived from a different G protein-coupled receptor. Similarly, the C-terminal domain may be replaced beginning at any residue between 311 and 323, preferably beginning at residue 319–320. Corresponding domains of other G protein-coupled receptors may be readily identified, as noted above, by performing an alignment of the receptor sequence with an MCH1R sequence provided herein. By way of example, the N-terminal domain, intracellular loop 3 and the C-terminal domain of macaque MCH2R may be amino acids 1–35, 222–248 and 312–340, respectively, of SEQ ID NO:34 or 36; intracellular loop 3 and the C-terminal domain of human $NPY_1$, may be amino acids 236–260 and 329–384, respectively, of SEQ ID NO:10; and the C-terminal domain of human beta-2 adrenergic receptor may be amino acids 344–413 of SEQ ID NO:24.

Preferred chimeric polypeptides are those in which IC3 loop, the C-terminal domain or the N-terminal domain is replaced. The sequences of certain representative chimeras are summarized in Table I and recited in SEQ ID NOs:18, 20, 28, 42, 44, 46, 48, 50, 52 and 60. More specifically, SEQ ID NO:18 is a human MCH1R/human $NPY_1$ receptor IC3 loop chimera in which the amino acid sequence of the third intracellular loop of MCH1R is replaced by the amino acid sequence of the third intracellular loop of the human $NPY_1$ receptor (polynucleotide sequence provided in SEQ ID NO:17); SEQ ID NO:20 is a human MCH1R/human $NPY_1$ receptor C-terminal chimera in which the C-terminal domain of MCH1R is replaced by the C-terminal domain of the human $NPY_1$ receptor (polynucleotide sequence provided in SEQ ID NO:19); SEQ ID NO:28 is a human MCH1R/human beta-2 adrenergic receptor C-terminal chimera in which the C-terminal domain of MCH1R is replaced by the C-terminal domain of the human beta-2 adrenergic receptor (polynucleotide sequence provided in SEQ ID NO:27); SEQ ID NO:42 is a cynomolgus macaque MCH1R/human $NPY_1$ receptor IC3 loop chimera (polynucleotide sequence provided in SEQ ID NO:41); SEQ ID NO:44 is a cynomolgus macaque MCH1R/human $NPY_1$ C-terminal chimera (polynucleotide sequence provided in SEQ ID NO:43); SEQ ID NO:46 is a cynomolgus macaque MCH1R/human beta-2 adrenergic receptor C-terminal chimera (polynucleotide sequence provided in SEQ ID NO:45); SEQ ID NOs:48 and 60 are cynomolgus macaque MCH1R/cynomolgus macaque MCH2R N-terminal chimeras, in which the N-terminal amino acid sequence of MCH1R is replaced by the N-terminal amino acid sequence of MCH2R (polynucleotide sequence provided in SEQ ID NO:47); SEQ ID NO:50 is a cynomolgus macaque MCH1R/cynomolgus macaque MCH2R IC3 loop chimera (polynucleotide sequence provided in SEQ ID NO:49); and SEQ ID NO:52 is a cynomolgus macaque MCH1R/cynomolgus macaque MCH2R C-terminal chimera (polynucleotide sequence provided in SEQ ID NO:51). It will be apparent that similar chimeras may be generated using the MCH1R long form shown in SEQ ID NO:56). As noted above, sequences that may be used to construct such chimeras are provided herein, and in the literature. Additional precise coding sequences suitable for the construction of a chimera may be readily determined by those of ordinary skill in the art from the amino acid sequences provided herein, and may be constructed using standard recombinant techniques.

TABLE I

Representative MCH1R Chimeras

| SEQ ID | MCH1R Residues | Inserted Domain |
|---|---|---|
| 18 | 1–232, 251–353 of SEQ ID NO:6 | Human NPY1 IC3 loop (aa 236–260 of SEQ ID NO:10) |
| 20 | 1–319 of SEQ ID NO:6 | Human NPY1 C-terminal (aa 329–384 of SEQ ID NO:10) |
| 28 | 1–319 of SEQ ID NO:6 | Human beta-2 adrenergic receptor C-terminal (aa 344–413 of SEQ ID NO:24) |
| 42 | 1–232, 254–353 of SEQ ID NO:2 | Human NPY1 IC3 loop (aa 236–260 of SEQ ID NO:10) |
| 44 | 1–319 of SEQ ID NO:2 | Human NPY1 C-terminal (aa 329–384 of SEQ ID NO:10) |
| 46 | 1–318 of SEQ ID NO:2 | Human beta-2 adrenergic receptor C-terminal (aa 344–413 of SEQ ID NO:24) |
| 48 | 36–353 of SEQ ID NO:2 | Macaque MCH2R N-terminal (aa 1–34 of SEQ ID NO:34 or 36) |
| 50 | 1–232, 254–353 of SEQ ID NO:2 | Macaque MCH2R IC3 loop (aa 222–248 of SEQ ID NO:34 or 36) |
| 52 | 1–319 of SEQ ID NO:2 | Macaque MCH2R C-terminal (aa 315–340 of SEQ ID NO:34 or 36) |
| 60 | 41–353 of SEQ ID NO:2 | Macaque MCH2R N-terminal (aa 1–34 of SEQ ID NO:34 or 36) |

Polypeptides may be prepared using any of a variety of well known techniques from transgenic cells (i.e., cells that have been genetically altered to express a MCH1R polypeptide). Recombinant polypeptides encoded by polynucleotide sequences as described above may be readily prepared from the, polynucleotide sequences using any of a variety of expression vectors known to those of ordinary skill in the art. Expression may be achieved in any appropriate host cell that has been transformed or transfected with at least one expression vector containing a DNA molecule that encodes a recombinant polypeptide. Suitable host cells include prokaryotes, yeast and higher eukaryotic cells, such as insect, mammalian or plant cells. Preferably, the host cells employed are *E. coli*, yeast, amphibian oocytes or a mammalian cell line such as COS, CHO, BHK, HEK 293, VERO, HeLa, MDCK, WI38 or NIH 3T3 cells. Insect cell systems infected with recombinant virus expression vectors (for example, baculovirus) comprising a MCH1R polynucleotide provided herein may also be employed. Alternatively, a transgenic cell may be isolated from a transgenic animal.

Within certain embodiments, a MCH1R polypeptide is present within a membrane preparation. Such preparations are generated from transgenic cells that express a MCH1R polypeptide, using any standard procedure. Briefly, transfected host cell pellets are homogenized and centrifuged (e.g., 10 minutes at 48,000×g). The supernatant is discarded and the pellet is resuspended and homogenized again to generate an isolated membrane preparation. A more detailed protocol is provided in Example 3 herein. Preferably, isolated membranes have an MCH binding activity that is at least 2-fold greater, preferably 10-fold greater and more preferably at least 20-fold greater than that exhibited by control membranes isolated from a control cell (e.g., an untransfected cell of the same cell line used to prepare the recombinant cell or a cell transfected with a control vector that does not encode an MCH1R polypeptide). Preferred membrane preparations contain at least 0.1 pmol, 1 pmol or 5 pmol of MCH receptor polypeptide per mg of total membrane protein.

As noted above, MCH1R polypeptides may comprise additional sequences, such as antibody recognition sequences, that are not naturally present within a G protein-coupled receptor. A tagged fusion protein may be purified using an antibody specific for the tag (e.g., by affinity chromatography). Such purification procedures will typically require detergent extraction, and may result in a decrease in signal transduction activity. Such purified proteins are useful as antigens for the preparation of receptor-specific antibodies, in which case the retention of receptor signal transduction function is typically of little consequence.

Chimeric proteins may be prepared using standard recombinant methods. Briefly, convenient restriction sites may be incorporated into a MCH1R polynucleotide using site-directed mutagenesis. This allows the removal of polynucleotide encoding a particular domain. The domain to be inserted may be synthesized, and ligated to the digested MCH1R polynucleotide. The resulting polynucleotide encodes the chimeric polypeptide, and may be expressed using standard techniques, and as described herein. A similar process may be used to generate polypeptides that comprise a single MCH1R domain inserted into a different G protein-coupled receptor.

Expression Systems

An expression vector is a vector for recombinant expression of a MCH1R polypeptide, comprising a MCH1R polynucleotide operatively linked to the necessary nucleotide sequences for expression (e.g., a suitable promoter and, if necessary, a terminating signal). A promoter is a nucleotide sequence (typically located 5' to the MCH receptor polynucleotide) that directs the transcription of adjacently linked coding sequences. A terminating signal may be a stop codon to end translation and/or a transcription termination signal. Additional regulatory element(s) (e.g., enhancer elements) may also be present within an expression vector. Such a vector is preferably a plasmid or viral vector. Techniques for incorporating DNA into such vectors are well known to those of ordinary skill in the art.

Preferably, an expression vector further comprises a selectable marker, which confers resistance to a selection. This allows cells to stably integrate the vector into their chromosomes and grow to form foci, which in turn can be cloned and expanded into cell lines. A number of selection systems can be used. For example, the hypoxanthine-guanine phosphoribosyl-transferase, adenine phosphoribosyl-transferase and herpes simplex virus thymidine kinase genes can be employed in hgprt$^-$, aprt$^-$ or tk$^-$cells, respectively. Also, anti-metabolite resistance can be used as the basis of selection for genes such as: dhfr, which confers resistance to methotrexate; gpt, which confers resistance to mycophenolic acid; neo, which confers resistance to the aminoglycoside G-418); hygro, which confers resistance to hygromycin; and puro, which confers resistance to puromycin.

Expression systems that may be used in the practice of certain aspects of the present invention include, but are not limited to, (a) insect cell systems infected with recombinant virus expression vectors (e.g., baculovirus) comprising one or more polynucleotides provided herein and (b) mammalian cell systems (e.g., COS, CHO, BHK, HEK 293, VERO, HeLa, MDCK, WI38 and NIH 3T3 cells) harboring recombinant expression constructs comprising one or more polynucleotides provided herein.

Mammalian vectors should contain promoters, preferably derived from the genome of mammalian cells (for example, a metallothionein actin or phosphoglycerate kinase promoter) or from mammalian viruses (for example, the adenovirus late promoter, a CMV promoter and the vaccinia virus 7.5K promoter). One suitable mammalian expression vector is the pcDNA3.1 vector (INVITROGEN, Carlsbad, Calif.). In adenoviral expression vectors, the MCH receptor polynucleotide may be ligated to an adenovirus transcription/translation control complex such as the late promoter and tripartite leader sequence. Specific initiation signals (e.g., the ATG initiation codon and adjacent sequences such as ribosome binding sites) may also be required for efficient translation of inserted nucleic acid molecules. The efficiency of expression may be further enhanced by the inclusion of appropriate transcription enhancer elements, transcription terminators, etc. The recombinant gene may then be inserted in the adenovirus genome by in vitro or in vivo recombination. Insertion in a non-essential region of the viral genome (for example, region E1 or E3) will result in a recombinant virus that is viable and capable of expressing an MCH receptor polypeptide in infected.

Another representative expression system is an amphibian oocyte system in which MCH1R RNA is introduced into an oocyte. Preferably the amphibian is a frog, most preferably the African clawed frog, *Xenopus laveis*. One suitable expression vector for expression in amphibian oocytes is the pBLUESCRIPT SK vector (STRATAGENE Cloning Systems, La Jolla, Calif.). Typically such vectors are used to generate MCH receptor polypeptide-encoding RNAs in in vitro transcription systems, which RNAs are then injected into the oocytes to induce expression of the encoded protein.

An insect system utilizing a baculovirus such as *Autographa californica* nuclear polyhedrosis virus (AcNPV) can be used to express the MCH receptor polypeptides provided herein. The virus grows in insect cells such as *Spodoptera frugiperda* cells. The coding sequence encoding the MCH receptor polypeptide is typically inserted (e.g., ligated) into non-essential regions of the virus (for example into the polyhedrin gene) and placed under control of an AcNPV promoter (for example the polyhedrin promoter). Preferably, the successful introduction of the insert will result in inactivation of a viral gene. For example, when targeted into the polyhedrin gene, the successful incorporation of the insert will inactivate that gene and result in production of non-occluded recombinant virus (i.e., virus lacking the proteinaceous coat coded for by the polyhedrin gene). The resulting recombinant viruses are then used to infect insect cells, preferably *Spodoptera frugiperda* cells, in which the inserted coding sequence is expressed. A variety of kits for use in the preparation of an insect expression system are commercially available.

Host cells transformed or transfected with an expression vector comprising an MCH receptor polynucleotide, and capable of expressing an MCH1R polypeptide, are further provided herein. Such cells may be prepared using standard transformation techniques. Stable expression is generally preferred, although transient expression systems may be suitable for certain uses. Following the introduction of the vector (often following incubation in a non-selective medium to allow for recovery from the stress of vector introduction), engineered cells may be grown in a selective medium.

Assays

MCH1R polynucleotides and polypeptides may be used within a variety of assays to screen for and characterize compounds that modulate MCH receptor function. Such assays typically involve contacting a test compound with transfected host cells or isolated membranes prepared from such cells, and subsequently detecting (a) binding of the test compound to the cells or membranes (direct binding assays—e.g., via surface plasmon resonance, using a device available from BIAcor AB, Sweden); (b) an effect of the test compound on labeled ligand (e.g., radiolabeled MCH) binding to the cells or membranes (competitive binding assays); or (c) an effect on a cellular receptor response to MCH (functional assays). Test compounds may be any substance, but are preferably small organic, non-peptide molecules. Active compounds identified using such assays are useful, for example, as tools for receptor mapping and as pharmaceutical agents.

One suitable competitive binding assay is provided within Example 4. In such an assay, a test compound is used as a cold displacer. Briefly, a MCH1R polypeptide-containing membrane preparation (e.g., prepared from transfected HEK293 cells) is contacted (incubated) with labeled (e.g., $^{125}I$) MCH and unlabeled test compound. Unbound MCH is then removed (e.g., by washing) and remaining bound label is detected. Incubation with a compound that detectably modulates MCH binding to MCH receptor will result in a decrease or increase in the amount of label bound to the MCH receptor preparation, relative to the amount of label bound in the absence of the compound. Preferably, such a compound will exhibit a $K_i$ at an MCH receptor of less than 1 micromolar, more preferably less than 500 nM, 100 nM, 20 nM or 10 nM, within a ligand binding assay performed as described in Example 4.

Functional assays use transfected host cells as substrates and measure cellular responses to contact with a test compound. Within such assays, a compound may act as an agonist, mediating a cell-based response when contacted with a cell-surface MCH receptor, or as an antagonist, inhibiting the response of cell-surface MCH receptor to an MCH receptor agonist (e.g., MCH). A representative functional assay in antagonist mode is set forth below as Example 5. Within $Ca^{2+}$ mobilization assays, MCH receptor modulating activity of a compound is detected by: (a) incubating (i.e., contacting) transgenic (e.g., transformed or transfected) cells with a compound; (b) detecting a level of $Ca^{2+}$ in the contacted cells; and (c) comparing the detected level of calcium with a level of $Ca^{2+}$ detected in control cells that are incubated in the absence of test compound. Preferably, within such assays, the transgenic cells are initially contacted with an indicator of intracellular $Ca^{2+}$ concentration, such as Fluo-3 Calcium Sensitive Dye (Molecular Probes; Eugene, Oreg.) and then washed. The compound is then contacted with the washed cells, and the level of calcium is detected by quantifying $Ca^{2+}$ concentration-dependant changes in the properties of the indicator of intracellular $Ca^{2+}$. The level of calcium detected in the presence of test compound is preferably at least 2-fold lower than the level detected in the absence of test compound (i.e., in control cells that are contacted with the indicator of intracellular $Ca^{2+}$ concentration, but not with the test compound).

MCH receptor antagonist activity may also be detected using calcium mobilization assays performed in the presence of a known MCH receptor agonist (e.g., MCH). MCH receptor agonist is preferably added to test and control cells just prior to detecting intracellular $Ca^{2+}$ concentration. Preferably, the concentration of intracellular $Ca^{2+}$ in the agonist-contacted test cell (i.e., contacted with agonist and test compound) is significantly less (to the $p \leqq 0.05$ level, as measured using a parametric test of statistical significance) than the concentration of intracellular $Ca^{2+}$ in the agonist-contacted control cell.

Compounds identified using such assays may be used for treating diseases and disorders associated with MCH receptor activation, such as eating disorders (e.g., obesity and bulimia nervosa), sexual disorders, diabetes, heart disease and stroke. Patients may include humans, companion animals (such as dogs) and livestock animals.

The following Examples are offered by way of illustration and not by way of limitation.

EXAMPLES

Example 1

MCH1R Polynucleotide Preparation

This Example illustrates the isolation of representative MCH1R polynucleotides.

A. Monkey MCH1R

RNA was isolated from cynomolgus macaque hypothalamus using Trizol Reagent (Life Technologies, Gaithersburg, Md.). cDNA was prepared using random primers and Reverse Transcriptase (Life Technologies) according to the manufacturer's instructions.

Cynomolgus macaque MCH1R cDNA was obtained using PCR, with the following primers:

```
5'Forward Outer Primer
GAGCAGGCGA CCGGCACTGG CTGG        (SEQ ID NO:7)

3'Reverse Primer
GGAGGTGTGC AGGGTGGCAG GGGAAGTA    (SEQ ID NO:8)
```

PCR was performed using the Advantage-GC cDNA PCR Kit (Clontech Laboratories Palo Alto, Calif.) in 50 microliter reactions containing: 10 microliters GC Melt, 10 microliters 5× PCR reaction buffer, 1 microliter 50× dNTP Mix (10 mM each), 12.5 pmol foward and reverse primers, 1 microliter Advantage-GC cDNA Polymerase Mix (50×), 1 microliter cynomolgus macaque RT product. Conditions for touch-down PCR were as follows:

94° C.—3 minutes 20 cycles:

94° C.—30 seconds

60° C. to 50° C. in 0.5° C. intervals for 20 rounds—30 seconds

68° C.—60 seconds 20 cycles:

94° C.—30 seconds

50° C.—30 seconds

68° C.—60 seconds

4° C.

The full length PCR product was initially cloned into the vector pGEM-T (PROMEGA, Madison, Wis.). The cDNA was reamplified using a forward primer engineered to include an optimal translation initiation site (Kozak sequence). A cDNA expression cassette fragment encoding the monkey MCH1R was blunt end ligated into the pCR-SCRIPT vector (STRATAGENE, La Jolla, Calif.). The receptor sequence was excised from this vector using EcoRI and Not I and subcloned into the EcoRI/Not I site of pcDNA3.1 (INVITROGEN Corp.; Carlsbad, Calif.).

A receptor cDNA expression cassette thus cloned from cynomolgus macaque total hypothalamic cDNA (and referred to herein as cynMacMCH1R, SEQ ID NO:1) was subcloned into the pcDNA3.1 expression vector to create the MCH1 receptor expression vector, CynMacMCH1RDNA. This cynMacMCH1R cDNA expression cassette has been also been cloned into pCR-Script, and pBacPac9 vectors. The nucleotide and amino acid sequences of cynomolgus macaque MCH1R are shown in SEQ ID NO:1 and 2, respectively.

The MCH1R 5' extension was cloned using rapid amplification of cDNA ends (RACE). Cynomolgus macaque temporal cortex total RNA was used as a template and RACE was performed using the FirstChoice™ RLM-RACE kit (Ambion, Austin, Tex.) according to the manufacturer's instructions, with the outer reverse primer corresponding to nucleotides 503–478 of SEQ ID NO:1 (CACAGGAGGCAGATCACCAGGGTGGC; SEQ ID NO:57) and the inner reverse primer corresponding to nucleotides 393–372 of SEQ ID NO:1 (GGTGCTGGTGAACTGA CTATTG; SEQ ID NO:58). PCR conditions were as follows:

94° C.—3 minutes 35 cycles:

94° C.—30 seconds

58° C.—30 seconds

68° C.—30 seconds

68° C.—7 minutes

4° C.

The sequence of the 5' region is shown in SEQ ID NO:53, with the encoded amino acid sequence in SEQ ID NO:54. The long form of MCH1R, which includes the 5' extension, is shown in SEQ ID NO:55 (DNA sequence) and SEQ ID NO:56 (amino acid sequence). Alignments of the monkey MCH1R sequences with other MCH1R sequences are shown in FIGS. 1(A and B) and 2.

B. Human MCH1R/Human NPY1 Receptor Intracellular Loop 3 Chimera

Human MCH1R (SEQ ID NO:5) was cloned as a PCR product from a Gibco Human Brain library (Life Technologies; Rockville, Md.) as described above using the following primers:

```
Forward 5'CCACCATGGACCTGGAAGCCTCG  (SEQ ID NO:31)

Reverse 5'AGGGTGGCAGGGGAAGTATC     (SEQ ID NO:32)
```

The human MCH1R cDNA (SEQ ID NO:5) was digested with BamH I (base 689–694) and BstE II (bases 759–765) to remove the IC3 loop domain. This corresponds to amino acids 230–255 in SEQ ID NO:6. The IC3 loop domain from the human NPY 1 receptor cDNA (SEQ ID NO:9, bases 706–779 and corresponding to amino acids 236–260 of SEQ ID NO:10) was constructed from two complementary oligonucleotides (SEQ ID NO:14 and SEQ ID NO:15) which contain the BamH I and BstE II sites. The two oligonucleotides were heated to 95° C., allowed to anneal, and are inserted into the digested MCH1R to yield the sequence the human MCH1R/human NPY1 receptor Intracellular Loop 3 chimera (SEQ ID NO:17). The corresponding amino acid sequence is given as SEQ ID NO:18. The entire sequence was subcloned into pcDNA 3.1 plus to yield SEQ ID NO:21.

C. Human MCH1R/Human NPY 1 Receptor C-Terminal Chimera

To exchange the human NPY1 receptor C-terminal with that of the human MCH1R, a BspE I restriction site was introduced into both receptors. In the human MCH1R (SEQ ID NO:5) a silent C to G point mutation was made at base 957 to produce SEQ ID NO:16. For the human NPY1 receptor C-terminal, base 983 was mutated from A to G which results in a Q to R amino acid change at 328 of SEQ ID NO:10. A PCR fragment (SEQ ID NO:13) generated with SEQ ID NO:9 as a template using primers SEQ ID NO:11 and SEQ ID NO:12 (SEQ ID NO:12 is mainly comprised of vector sequence) was amplified. This PCR fragment was subcloned BspE I to Not I into the mutated human MCH1R (SEQ ID NO:16) to form the human MCH1R/human NPY1 receptor C-terminal chimera (SEQ ID NO:19). The corresponding amino acid sequence is given as SEQ ID NO:20. The final sequence in pcDNA 3.1 plus is given as SEQ ID NO:21.

D. Human MCH1R/Human Beta Adrenergic Receptor C-Terminal Chimera

The C-terminal sequence from the human beta-2 adrenergic receptor (SEQ ID NOs:23 and 24) was also used form a human MCH1R/beta adrenergic receptor C-terminal chimera. Primers (SEQ ID NOs:25 and 26) were used to amplify a PCR product from the human beta-2 adrenergic receptor (SEQ ID NO:23) which includes a BspE I site on the 5' end and an Xba I site on the 3' end. This fragment was introduced BspE I to Xba I into the human MCH1R mutated at base 957 as discussed above (SEQ ID NO:16) to form the Human MCH1R/human beta adrenergic receptor C-terminal chimera (SEQ ID NO:27). The corresponding amino acid sequence is given as SEQ ID NO:28. The final sequence in pcDNA 3.1 plus is given as SEQ ID NO:29.

It will be apparent that similar cloning procedures can be used to generate the corresponding chimeras based on the monkey MCH1R sequence and/or substituting domains from other G protein-coupled receptors.

Example 2

Preparation of Host Cells Expressing MCH1R Polypeptides

This Example illustrates the expression of representative MCH1R polynucleotides in host cells.

HEK 293 cells were transiently or stably transfected via standard calcium phosphate precipitation procedures with the CynMacDNA monkey MCH1 receptor expression vector described in Example 1.

For transient transfection, cells were grown to confluency at 37° C., 5% $CO_2$, for approximately 48–72 hours in DMEM high glucose culture medium (catalog #10–017-CV, MEDIATECH, Herndon, Va.) supplemented with 10% fetal bovine serum, 25 mM HEPES. Cells could then be used directly within assays. For stable expression, cells were grown under the conditions described above (with the addition of 500 μg/ml G418) for 2–3 weeks. Single selected colonies were then chosen to generate a stable cell line.

CHO (Chinese Hamster Ovary) cells were also transfected via standard calcium phosphate precipitation procedures with the MCH1R expression vector. For transient transfection, cells were grown to confluency at 37° C., 5% $CO_2$, approximately 48–72 hours, in Ham's F12 culture medium (catalog #10–080-CV, MEDIATECH, Herndon, Va.) supplemented with 10% fetal bovine serum, 25 mM HEPES. Cells could then be used directly within assays. For stable expression, cells were grown under the conditions described above (with the addition of 500 μg/ml G418) for 2–3 weeks. Single selected colonies were then chosen to generate a stable cell line.

Example 3

Preparation of Isolated Membranes

This Example illustrates the preparation of isolated membranes comprising MCH1R polypeptides, for use within a variety of binding and activity assays.

Transfected HEK 293 cell pellets stored frozen at −80° C. are thawed by addition of wash buffer (25 mM Hepes with 1.0 mM $CaCl_2$, 5.0 mM $MgCl_2$, 120 mM NaCl, PH 7.4) and homogenized for 30 seconds using a BRINKMAN POLYTRON, setting 5. Cells are centrifuged for 10 minutes at 48,000×g. The supernatant is discarded and the pellet is resuspended in fresh wash buffer, and homogenized again. The protein concentration of the resulting membrane preparation is measured using the Bradford protein assay (Bio-Rad Laboratories, Hercules, Calif.). By this measure, a 1-liter culture of cells typically yields 50–75 mg of total membrane protein.

Example 4

MCH1R Ligand Binding Assays

This Example illustrates the use of MCH1R-containing membranes within binding assays to monitor the ability of cells expressing MCH receptors to bind MCH or to screen for MCH1R agonists and antagonists.

Purified membranes from HEK 293 cells expressing MCH1R are prepared as described above. The membrane homogenate is centrifuged as before and resuspended to a protein concentration of 333 μg/ml in binding buffer (Wash buffer+0.1% BSA and 1.0 μM final conc. phosphoramidon) for an assay volume of 50 μg membrane protein/150 μl binding buffer. Phosphoramidon is from SIGMA BIOCHEMICALS, St. Louis, Mo. (cat# R-7385).

Ligand binding assays are performed at room temperature by combining 150 μl of MCH1R-containing membranes in binding buffer, prepared as described above, 50 μl $^{125}$I-Tyr MCH in binding buffer and 50 μl binding buffer. $^{125}$I-Tyr MCH (specific activity=2200 Ci/mMol) is purchased from NEN, Boston, Mass. (Cat # NEX 373) and is diluted in binding buffer to provide a final assay concentration of 30 pM.

Competition binding assays for screening test compounds are performed at room temperature in Falcon 96 well round bottom polypropylene plates. To each assay well is added 150 μl of MCH1R-containing membranes in binding buffer, prepared as described above, 50 μl $^{125}$I-Tyr MCH in binding buffer, 50 μl binding buffer and 2 μl test compound in DMSO.

Non-specific binding is defined as the binding measured in the presence of 1 μM unlabeled MCH. MCH is purchased from BACHEM U.S.A., King of Prussia, Pa. (cat # H-1482). To each assay well used to determine non-specific MCH binding is added: 150 μl of MCH1R-containing membranes in binding buffer, 50 μl $^{125}$I-Tyr MCH in binding buffer, unlabeled MCH in 25 μl binding buffer, and 25 μl binding buffer.

Assay plates are incubated for 1 hour at room temperature. Membranes are harvested onto WALLAC glass fiber filters (PERKIN-ELMER, Gaithersburg, Md.) which are pre-soaked with 1.0% PEI (polyethyleneimine) for 2 hours prior to use. Filters are allowed to dry overnight then counted in a WALLAC 1205 BETA PLATE counter after addition of WALLAC BETA SCINT scintillation fluid.

For saturation binding the concentration of $^{125}$I-Tyr MCH is varied from 7–1,000 pM. Typically 11 concentration points are collected per saturation binding curve. Equilibrium binding parameters are determined by fitting the allosteric Hill equation to the measured values with the aid of the computer program FitP™ (BIOSOFT, Ferguson, Mo.).

Example 5

MCH1R Calcium Mobilization Assay

This Example illustrates the use of MCH1R-expressing cells within functional assays to monitor the response of cells expressing MCH receptors to MCH or to screen for MCH1R agonists and antagonists.

CHO or HEK 293 cells stably transfected with an MCH1R receptor expression vector as described above are grown to a density of 30,000 cells/well in FALCON black-walled, clear-bottomed 96-well plates (#3904, BECTON-DICKINSON, Franklin Lakes, N.J.). Prior to running the assay the culture medium is emptied from the 96 well plates. Fluo-3 calcium sensitive dye (Molecular Probes, Eugene, Oreg.) is added to each well (dye solution: 1 mg FLUO-3 AM, 440 μl DMSO and 440 μl 20% pluronic acid in DMSO; diluted 8.8 μl/ml with KRH; 50 μl diluted solution added per well). Plates are covered with aluminum foil and incubated at 37° C. for 1–2 hours. After the incubation the dye solution is emptied from the plates, cells are washed once in 100 μl KRH buffer (0.05 mM KCl, 0.115 M NaCl, 9.6 mM $NaH_2PO_4$, 0.01 mM $MgSO_4$, 1 mM probenecid (Sigma), 25 mM HEPES, pH 7.4) to remove excess dye; after washing 80 μl KRH buffer is added to each well.

In order to measure the ability of a test compound to antagonize the response of cells expressing MCH1R to MCH, the $EC_{50}$ of MCH is first determined. An additional 20 μl of KRH buffer and 1 μl DMSO is added to each well of cells, prepared as described immediately above. 100 μl human MCH in KRH buffer is automatically transferred by a FLIPR™ plate reader (Molecular Devices, Sunnyvale, Calif.) to each well, and fluorescence response is monitored by excitation at 480 nM and emission at 530 nM. An 8-point concentration response curve, with final MCH concentrations of 1 nM to 3 μM, is used to determine MCH $EC_{50}$.

Test compounds are dissolved in DMSO, diluted in 20 μl KRH buffer, and added to cells prepared as described above. The 96 well plates containing prepared cells and test compounds are incubated in the dark, at room temperature for 0.5 to 6 hours. It is important that the incubation not continue beyond 6 hours. Just prior to determining the fluorescence response, 100 μl human MCH diluted in KRH buffer to $2\times EC_{50}$ is automatically added by the FLIPR instrument to each well of the 96 well plate for a final sample volume of 200 μl and a final MCH concentration of $EC_{50}$. The final concentration of test compounds in the assay wells is between 1 μM and 5 μM. Typically cells exposed to one $EC_{50}$ of MCH exhibit a fluorescence response of about 10,000 Relative Fluorescence Units. Antagonists of the MCH receptor exhibit a response that is significantly less than that of the control cells to the $p \leqq 0.05$ level, as measured using a parametric test of statistical significance. Typically, antagonists of the MCH receptor decrease the fluorescence response relative to control cells by about 20%, preferably by about 50%, and most preferably by at least 80% as compared to matched control.

What is claimed is:

1. An MCH1R chimeric polypeptide, comprising a MCH1R sequence recited in SEQ ID NO:2 or 56 in which one or more domains chosen from the third intracellular loop and C-terminal domain is replaced with a corresponding domain of MCH2R, $NPY_1$ receptor or beta-2-adrenergic receptor, and wherein the polypeptide detectably binds melanin concentrating hormone in a MCH1R ligand binding assay.

2. The MCH1R chimeric polypeptide according to claim 1, wherein the third intracellular loop is replaced with the corresponding domain of human $NPY_1$.

3. The MCH1R chimeric polypeptide according to claim 1, wherein the third intracellular loop is replaced with the corresponding domain of macaque MCH2R.

4. The MCH1R chimeric polypeptide according to claim 1, wherein the C-terminal domain is replaced with the corresponding domain of human NPY1.

5. The MCH1R chimeric polypeptide according to claim 1, wherein the C-terminal domain is replaced with the corresponding domain of macaque MCH2R.

6. The MCH1R chimeric polypeptide according to claim 1, wherein the chimeric polypeptide has a sequence recited in any one of SEQ ID NOs:42, 44, 46, 50, or 52.

7. An isolated polypeptide, wherein the polypeptide comprises at least amino acid residues 2 to 230 of SEQ ID NO:2.

8. The isolated polypeptide according to claim 7, wherein the polypeptide comprises at least amino acid residues 2 to 353 of SEQ ID NO:2.

* * * * *